(12) United States Patent
Burton et al.

(10) Patent No.: US 11,723,975 B2
(45) Date of Patent: Aug. 15, 2023

(54) COMPOSITIONS COMPRISING AN ANTI-LAG-3 ANTIBODY OR AN ANTI-LAG-3 ANTIBODY AND AN ANTI-PD-1 OR ANTI-PD-L1 ANTIBODY

(71) Applicant: Bristol-Myers Squibb Company, Princeton, NJ (US)

(72) Inventors: Lori S. Burton, Robbinsville, NJ (US); William Ying, Martinsville, NJ (US); Nils Lonberg, Woodside, CA (US); Sudhir Chakravarthi, Manalapan, NJ (US); Pedro Smith, Crane Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/616,583

(22) PCT Filed: May 30, 2018

(86) PCT No.: PCT/US2018/035142
§ 371 (c)(1),
(2) Date: Nov. 25, 2019

(87) PCT Pub. No.: WO2018/222722
PCT Pub. Date: Dec. 6, 2018

(65) Prior Publication Data
US 2021/0283251 A1    Sep. 16, 2021

Related U.S. Application Data

(60) Provisional application No. 62/513,816, filed on Jun. 1, 2017, provisional application No. 62/512,644, filed on May 30, 2017.

(51) Int. Cl.
| | | |
|---|---|---|
| A61K 39/395 | (2006.01) | |
| A61K 9/00 | (2006.01) | |
| A61K 45/06 | (2006.01) | |
| A61K 47/02 | (2006.01) | |
| A61K 47/12 | (2006.01) | |
| A61K 47/18 | (2017.01) | |
| A61K 47/22 | (2006.01) | |
| A61K 47/26 | (2006.01) | |
| A61K 47/34 | (2017.01) | |
| C07K 16/28 | (2006.01) | |
| A61J 1/14 | (2023.01) | |
| A61K 39/00 | (2006.01) | |

(52) U.S. Cl.
CPC ...... *A61K 39/39591* (2013.01); *A61K 9/0019* (2013.01); *A61K 39/3955* (2013.01); *A61K 45/06* (2013.01); *A61K 47/02* (2013.01); *A61K 47/12* (2013.01); *A61K 47/183* (2013.01); *A61K 47/22* (2013.01); *A61K 47/26* (2013.01); *A61K 47/34* (2013.01); *C07K 16/2803* (2013.01); *C07K 16/2818* (2013.01); *C07K 16/2827* (2013.01); *A61J 1/1412* (2013.01); *A61K 2039/54* (2013.01); *A61K 2039/545* (2013.01); *C07K 2317/21* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 5,545,806 | A | 8/1996 | Lonberg et al. |
| 5,773,578 | A | 6/1998 | Hercend et al. |
| 5,811,097 | A | 9/1998 | Allison et al. |
| 5,874,250 | A | 2/1999 | Hercend et al. |
| 5,976,877 | A | 11/1999 | Hercend et al. |
| 6,143,273 | A | 11/2000 | Faure et al. |
| 6,197,524 | B1 | 3/2001 | Romagnani |
| 6,207,156 | B1 | 3/2001 | Kuchroo et al. |
| 6,482,925 | B1 | 11/2002 | El Tayar et al. |
| 6,500,422 | B2 | 12/2002 | Biffoni |
| RE38,313 | E | 11/2003 | Faure et al. |

(Continued)

FOREIGN PATENT DOCUMENTS

| | | |
|---|---|---|
| CN | 101490085 A | 7/2009 |
| JP | 2006340714 A | 12/2006 |

(Continued)

OTHER PUBLICATIONS

Agrawal, S., et al., "Clinical Pharmacokinetics (PK) of BMS-936558, a Fully Human Anti-pd-1 Monoclonal Antibody," Journal of Clinical Oncology 30(15):1 (2012), ASCO Annual Meeting Website, [retrieved on Jan. 13, 2015]. Retrieved from the Internet: URL:http://www.meetinglibrary.asco.org/content/98623-114.

Anonymous: "A Phase 1 Dose Escalation and Cohort Expansion Study of the Safety, Tolerability, and Efficacy of Anti-LAG-3 (BMS-986016) in Relapsed or Refractory Chronic Lymphocytic Leukemia and Lymphomas and Multiple Myeloma," ClinicaiTrials. gov Archive Identifier NCT02061761, accessed at https://clinicaltrials.gov/archive/NCT02061761/2014_11_20, accessed on Jun. 16, 2015, 5 pages.

(Continued)

*Primary Examiner* — Yunsoo Kim
(74) *Attorney, Agent, or Firm* — Sterne, Kessler, Goldstein & Fox P.L.L.C.

(57) ABSTRACT

This provides pharmaceutical compositions that comprise (i) an anti-LAG-3 antibody or antigen binding fragment thereof or (ii) an anti-LAG-3 antibody or antigen binding fragment thereof and an anti-PD-1 antibody, anti-PD-L1 antibody, or antigen binding fragment thereof. Also provided are pharmaceutical compositions that comprise a buffering agent, stabilizing or bulking agent, and a surfactant. The disclosure also provides a vial, syringe, intravenous bag, or kit that comprises the compositions, and methods for using the compositions.

24 Claims, 13 Drawing Sheets
Specification includes a Sequence Listing.

(56) References Cited

U.S. PATENT DOCUMENTS

| | | |
|---|---|---|
| 6,808,710 B1 | 10/2004 | Wood et al. |
| 7,138,501 B2 | 11/2006 | Ruben et al. |
| 7,306,906 B2 | 12/2007 | Maruyama et al. |
| 7,329,737 B2 | 2/2008 | Sexton et al. |
| 7,488,802 B2 | 2/2009 | Collins et al. |
| 7,563,441 B2 | 7/2009 | Graus et al. |
| 7,595,048 B2 | 9/2009 | Honjo et al. |
| 7,605,238 B2 | 10/2009 | Korman et al. |
| 7,635,757 B2 | 12/2009 | Freeman et al. |
| 7,790,160 B2 | 9/2010 | Von Strandmann et al. |
| 7,850,965 B2 | 12/2010 | Jensen et al. |
| 7,943,743 B2 | 5/2011 | Korman et al. |
| 8,008,449 B2 | 8/2011 | Korman et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,354,509 B2 | 1/2013 | Carven et al. |
| 8,383,796 B2 | 2/2013 | Korman et al. |
| 8,409,577 B2 | 4/2013 | Thompson et al. |
| 8,476,419 B2 | 7/2013 | Thielemans |
| 8,551,481 B2 | 10/2013 | Pardoll et al. |
| 8,609,089 B2 | 12/2013 | Langermann et al. |
| 8,686,119 B2 | 4/2014 | Rotem-Yehudar et al. |
| 8,728,474 B2 | 5/2014 | Honjo et al. |
| 8,779,105 B2 | 7/2014 | Korman et al. |
| 8,900,587 B2 | 12/2014 | Carven et al. |
| 9,005,614 B2 | 4/2015 | Damiano et al. |
| 9,005,629 B2 | 4/2015 | Pardoll et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,725 B2 | 8/2015 | Korman et al. |
| 9,212,224 B2 | 12/2015 | Cogswell et al. |
| 9,273,135 B2 | 3/2016 | Korman et al. |
| 9,358,289 B2 | 6/2016 | Korman et al. |
| 9,387,247 B2 | 7/2016 | Korman et al. |
| 9,393,301 B2 | 7/2016 | Honjo et al. |
| 9,402,899 B2 | 8/2016 | Honjo et al. |
| 9,439,962 B2 | 9/2016 | Honjo et al. |
| 9,492,539 B2 | 11/2016 | Korman et al. |
| 9,492,540 B2 | 11/2016 | Korman et al. |
| 9,505,839 B2 | 11/2016 | Lonberg et al. |
| 9,683,048 B2 | 1/2017 | Freeman et al. |
| 9,580,505 B2 | 2/2017 | Korman et al. |
| 9,580,507 B2 | 2/2017 | Korman et al. |
| 9,856,320 B2 | 1/2018 | Cogswell |
| 10,072,082 B2 | 9/2018 | Cogswell |
| 10,081,681 B2 | 9/2018 | Korman et al. |
| 10,138,299 B2 | 11/2018 | Cogswell |
| 10,266,591 B2 | 4/2019 | Lonberg |
| 10,266,594 B1 | 4/2019 | Cogswell |
| 10,266,595 B2 | 4/2019 | Cogswell |
| 10,266,596 B1 | 4/2019 | Cogswell |
| 10,308,714 B2 | 6/2019 | Cogswell |
| 10,316,090 B2 | 6/2019 | Cogswell |
| 10,316,091 B2 | 6/2019 | Cogswell |
| 10,323,092 B2 | 6/2019 | Cogswell |
| 10,323,093 B2 | 6/2019 | Cogswell |
| 10,344,089 B2 | 7/2019 | Thudium |
| 10,358,495 B2 | 7/2019 | Ullman et al. |
| 10,377,824 B2 | 8/2019 | Lonberg et al. |
| 10,441,655 B2 | 10/2019 | Korman et al. |
| 10,577,423 B2 | 3/2020 | Cogswell et al. |
| 10,584,170 B2 | 3/2020 | Cogswell et al. |
| 10,604,575 B2 | 3/2020 | Cogswell et al. |
| 10,988,535 B2 | 4/2021 | Thudium |
| 10,988,536 B2 | 4/2021 | Thudium |
| 11,001,630 B2 | 5/2021 | Thudium |
| 11,236,163 B2 | 2/2022 | Thudium |
| 11,236,164 B2 | 2/2022 | Thudium |
| 11,236,165 B2 | 2/2022 | Thudium |
| 11,274,152 B2 | 3/2022 | Korman et al. |
| 11,345,752 B2 | 5/2022 | Lonberg et al. |
| 2002/0086014 A1 | 7/2002 | Korman et al. |
| 2002/0146753 A1 | 10/2002 | Ditzel et al. |
| 2003/0059937 A1 | 3/2003 | Ruben et al. |
| 2003/0129601 A1 | 7/2003 | Cole |
| 2004/0072164 A1 | 4/2004 | Maruyama et al. |
| 2004/0171551 A1 | 9/2004 | Triebel |
| 2005/0009136 A1 | 1/2005 | Nixon et al. |
| 2005/0226876 A1 | 10/2005 | Graus et al. |
| 2005/0276823 A1* | 12/2005 | Cini ............... A61K 47/183 424/400 |
| 2006/0083744 A1 | 4/2006 | Chen et al. |
| 2006/0088523 A1* | 4/2006 | Andya ............ A61K 39/39541 424/133.1 |
| 2006/0110383 A1 | 5/2006 | Honjo et al. |
| 2006/0177442 A1 | 8/2006 | Von Strandmann et al. |
| 2006/0240024 A1 | 10/2006 | Pardoll et al. |
| 2007/0004910 A1 | 1/2007 | Sexton et al. |
| 2007/0160598 A1 | 7/2007 | Dennis et al. |
| 2008/0038264 A1 | 2/2008 | Bodary et al. |
| 2008/0069822 A1 | 3/2008 | Jensen et al. |
| 2008/0260641 A1 | 10/2008 | Teeling et al. |
| 2008/0279865 A1 | 11/2008 | Gomez-Navarro |
| 2009/0055944 A1 | 2/2009 | Korman et al. |
| 2009/0203538 A1 | 8/2009 | Sugioka et al. |
| 2009/0217401 A1 | 8/2009 | Korman et al. |
| 2009/0252741 A1 | 10/2009 | Liu |
| 2009/0297518 A1 | 12/2009 | Honjo et al. |
| 2009/0317368 A1 | 12/2009 | Chen |
| 2010/0055102 A1 | 3/2010 | Langermann et al. |
| 2010/0196394 A1 | 8/2010 | Pardoll et al. |
| 2010/0233183 A1 | 9/2010 | Triebel et al. |
| 2011/0007023 A1 | 1/2011 | Abrahamsson et al. |
| 2011/0081341 A1 | 4/2011 | Honjo et al. |
| 2011/0150892 A1 | 6/2011 | Thudium et al. |
| 2011/0209230 A1 | 8/2011 | Korman et al. |
| 2013/0122014 A1 | 5/2013 | Korman et al. |
| 2013/0133091 A1 | 5/2013 | Korman et al. |
| 2013/0309250 A1 | 11/2013 | Cogswell et al. |
| 2014/0093511 A1 | 4/2014 | Lonberg et al. |
| 2014/0212422 A1 | 7/2014 | Korman et al. |
| 2014/0271684 A1 | 9/2014 | Li |
| 2014/0294852 A1 | 10/2014 | Korman et al. |
| 2014/0314714 A1 | 10/2014 | Honjo et al. |
| 2014/0328833 A1 | 11/2014 | Korman et al. |
| 2014/0341917 A1 | 11/2014 | Nastri et al. |
| 2014/0348743 A1 | 11/2014 | Korman et al. |
| 2015/0079109 A1 | 3/2015 | Li et al. |
| 2015/0093380 A1 | 4/2015 | Honjo et al. |
| 2015/0125463 A1 | 5/2015 | Cogswell et al. |
| 2015/0165025 A1 | 6/2015 | Korman et al. |
| 2015/0197572 A1 | 7/2015 | Honjo et al. |
| 2015/0259420 A1 | 9/2015 | Triebel et al. |
| 2015/0307609 A1 | 10/2015 | Lonberg et al. |
| 2015/0337038 A1 | 11/2015 | Korman et al. |
| 2016/0024593 A1 | 1/2016 | Zheng et al. |
| 2016/0075782 A1 | 3/2016 | Korman et al. |
| 2016/0090417 A1 | 3/2016 | Cogswell et al. |
| 2016/0108121 A1 | 4/2016 | Pardoll et al. |
| 2016/0152720 A1 | 6/2016 | Kim et al. |
| 2016/0158355 A1 | 6/2016 | Honjo et al. |
| 2016/0158356 A1 | 6/2016 | Honjo et al. |
| 2016/0222116 A1 | 8/2016 | Korman et al. |
| 2016/0272708 A1 | 9/2016 | Chen |
| 2016/0326248 A1 | 11/2016 | Gutierrez et al. |
| 2016/0362495 A1 | 12/2016 | Korman et al. |
| 2017/0051060 A1 | 2/2017 | Honjo et al. |
| 2017/0088615 A1 | 3/2017 | Korman et al. |
| 2017/0101472 A1 | 4/2017 | Ullman et al. |
| 2017/0137514 A1 | 5/2017 | Lonberg et al. |
| 2017/0143827 A1 | 5/2017 | Vikram et al. |
| 2017/0158767 A1 | 6/2017 | Korman et al. |
| 2017/0168054 A1 | 6/2017 | Balko et al. |
| 2017/0260271 A1 | 9/2017 | Igawa et al. |
| 2018/0066154 A1 | 3/2018 | Thudium |
| 2018/0086830 A1 | 3/2018 | Triebel et al. |
| 2018/0282414 A1 | 6/2018 | Cogswell |
| 2018/0244773 A1 | 8/2018 | Gutierrez et al. |
| 2018/0273624 A1 | 9/2018 | Cogswell |
| 2018/0282413 A1 | 10/2018 | Cogswell |
| 2018/0312590 A1 | 11/2018 | Cogswell |
| 2018/0319887 A1 | 11/2018 | Cogswell |

(56) References Cited

U.S. PATENT DOCUMENTS

| | | |
|---|---|---|
| 2018/0371087 A1 | 12/2018 | Lonberg |
| 2019/0092863 A1 | 3/2019 | Cogswell |
| 2019/0100589 A1 | 4/2019 | Cogswell |
| 2019/0100590 A1 | 4/2019 | Cogswell |
| 2019/0112376 A1 | 4/2019 | Cogswell |
| 2019/0112377 A1 | 4/2019 | Cogswell |
| 2019/0135920 A1 | 5/2019 | Cogswell |
| 2019/0153099 A1 | 5/2019 | Cogswell |
| 2019/0256594 A1 | 8/2019 | Lonberg et al. |
| 2019/0276538 A1 | 9/2019 | Thudium |
| 2019/0276539 A1 | 9/2019 | Thudium |
| 2020/0062846 A1 | 2/2020 | Honjo et al. |
| 2020/0062848 A1 | 2/2020 | Korman et al. |
| 2020/0138945 A1 | 5/2020 | Korman et al. |
| 2020/0231671 A1 | 7/2020 | Thudium |
| 2020/0308282 A1 | 10/2020 | Cogswell et al. |
| 2020/0385466 A1 | 12/2020 | Thudium |
| 2020/0385467 A1 | 12/2020 | Thudium |
| 2021/0009692 A1 | 1/2021 | Korman et al. |
| 2021/0122820 A1 | 4/2021 | Gutierrez et al. |
| 2021/0238287 A1 | 8/2021 | Srivastava et al. |
| 2021/0261666 A1 | 8/2021 | Novotny, Jr. et al. |
| 2021/0338813 A1 | 11/2021 | Maurer et al. |
| 2021/0340250 A1 | 11/2021 | Korman et al. |
| 2022/0185892 A1 | 6/2022 | Korman et al. |
| 2022/0195040 A1 | 6/2022 | Thudium et al. |
| 2022/0204612 A1 | 6/2022 | Thudium et al. |

FOREIGN PATENT DOCUMENTS

| | | |
|---|---|---|
| WO | WO-9110682 A1 | 7/1991 |
| WO | WO-9530750 A2 | 11/1995 |
| WO | WO-9703695 A1 | 2/1997 |
| WO | WO-9713852 A1 | 4/1997 |
| WO | WO-9732733 A1 | 9/1997 |
| WO | WO-9842752 A1 | 10/1998 |
| WO | WO-9858059 A1 | 12/1998 |
| WO | WO-0037504 A2 | 6/2000 |
| WO | WO-0069914 A2 | 11/2000 |
| WO | WO-0114424 A2 | 3/2001 |
| WO | WO-200243478 A2 | 6/2002 |
| WO | WO-03088808 A2 | 10/2003 |
| WO | WO-03099196 A2 | 12/2003 |
| WO | WO-2004004771 A1 | 1/2004 |
| WO | WO-2004039956 A2 | 5/2004 |
| WO | WO-2004078928 A2 | 9/2004 |
| WO | WO-2005034733 A2 | 4/2005 |
| WO | WO-2005059106 A2 | 6/2005 |
| WO | WO-2005067620 A2 | 7/2005 |
| WO | WO-2006007850 A1 | 1/2006 |
| WO | WO-2006121168 A1 | 11/2006 |
| WO | WO-2006133396 A2 | 12/2006 |
| WO | WO-2007005874 A2 | 1/2007 |
| WO | WO-2008007648 A1 | 1/2008 |
| WO | WO-2008073160 A2 | 6/2008 |
| WO | WO-2008121615 A2 | 10/2008 |
| WO | WO-2008121616 A2 | 10/2008 |
| WO | WO-2008132601 A1 | 11/2008 |
| WO | WO-2008156712 A1 | 12/2008 |
| WO | WO-2009014708 A2 | 1/2009 |
| WO | WO-2009044273 A2 | 4/2009 |
| WO | WO-2009114335 A2 | 9/2009 |
| WO | WO-2010019570 A2 | 2/2010 |
| WO | WO-2011008092 A2 | 1/2011 |
| WO | WO-2011066389 A1 | 6/2011 |
| WO | WO-2011161699 A2 | 12/2011 |
| WO | WO-2012009442 A2 | 1/2012 |
| WO | WO-2012054438 A1 | 4/2012 |
| WO | WO-2012059858 A1 | 5/2012 |
| WO | WO-2012145493 A1 | 10/2012 |
| WO | WO-2013014668 A1 | 1/2013 |
| WO | WO-2013063186 A2 | 5/2013 |
| WO | WO-2013079174 A1 | 6/2013 |
| WO | WO-2013173223 A1 | 11/2013 |
| WO | WO-2016168716 A1 | 11/2013 |
| WO | WO-2013181634 A2 | 12/2013 |
| WO | WO-2014008218 A1 | 1/2014 |
| WO | WO-2014140180 A1 | 9/2014 |
| WO | WO-2014179664 A2 | 11/2014 |
| WO | WO-2014194302 A2 | 12/2014 |
| WO | WO-2014206107 A1 | 12/2014 |
| WO | WO-2015016718 A1 | 2/2015 |
| WO | WO-2015035606 A1 | 3/2015 |
| WO | WO-2015042246 A1 | 3/2015 |
| WO | WO-2015085847 A1 | 6/2015 |
| WO | WO-2015094995 A2 | 6/2015 |
| WO | WO-2015094996 A2 | 6/2015 |
| WO | WO-2015095404 A2 | 6/2015 |
| WO | WO-2015112800 A1 | 7/2015 |
| WO | WO-2015112900 A1 | 7/2015 |
| WO | WO-2015116539 A1 | 8/2015 |
| WO | WO-2015138920 A1 | 9/2015 |
| WO | WO-2015200119 A1 | 12/2015 |
| WO | WO-2016028672 A1 | 2/2016 |
| WO | WO-2016106159 A1 | 6/2016 |
| WO | WO-2016110593 A1 | 7/2016 |
| WO | WO-2016126858 A2 | 8/2016 |
| WO | WO-2016127220 A1 | 8/2016 |
| WO | WO-2016149201 A2 | 9/2016 |
| WO | WO-2016176504 A1 | 11/2016 |
| WO | WO-2016197367 A1 | 12/2016 |
| WO | WO-2016200782 A1 | 12/2016 |
| WO | WO-2017004153 A1 | 1/2017 |
| WO | WO-2017004532 A1 | 1/2017 |
| WO | WO-2017013436 A1 | 1/2017 |
| WO | WO-2017015560 A2 | 1/2017 |
| WO | WO-2017019846 A1 | 2/2017 |
| WO | WO-2017019894 A1 | 2/2017 |
| WO | WO-2017020291 A1 | 2/2017 |
| WO | WO-2017020858 A1 | 2/2017 |
| WO | WO-2017024465 A1 | 2/2017 |
| WO | WO-2017024515 A1 | 2/2017 |
| WO | WO-2017025016 A1 | 2/2017 |
| WO | WO-2017025051 A1 | 2/2017 |
| WO | WO-2017025498 A1 | 2/2017 |
| WO | WO-2017034916 A1 | 3/2017 |
| WO | WO-2017037203 A1 | 3/2017 |
| WO | WO-2017040790 A1 | 3/2017 |
| WO | WO-2007045996 A1 | 4/2017 |
| WO | WO-2017062888 A1 | 4/2017 |
| WO | WO-2017070585 A1 | 4/2017 |
| WO | WO-2017079150 A1 | 5/2017 |
| WO | WO-2017086367 A1 | 5/2017 |
| WO | WO-2017086419 A1 | 5/2017 |
| WO | WO-2017087589 A2 | 5/2017 |
| WO | WO-2017087599 A1 | 5/2017 |
| WO | WO-2017087678 A2 | 5/2017 |
| WO | WO-2017087901 A2 | 5/2017 |
| WO | WO-2017106061 A1 | 6/2017 |
| WO | WO-2017106129 A1 | 6/2017 |
| WO | WO-2017123557 A1 | 7/2017 |
| WO | WO-2017132827 A1 | 8/2017 |
| WO | WO-2017133540 A1 | 8/2017 |
| WO | WO-2017149143 A1 | 9/2017 |
| WO | WO-2017198741 A1 | 11/2017 |
| WO | WO-2017219995 A1 | 12/2017 |
| WO | WO-2017220555 A1 | 12/2017 |
| WO | WO-2017220569 A1 | 12/2017 |
| WO | WO-2018034227 A1 | 2/2018 |
| WO | WO-2018057506 A1 | 3/2018 |
| WO | WO-2018069500 A2 | 4/2018 |
| WO | WO-2018071500 A1 | 4/2018 |
| WO | WO-2018071824 A1 | 4/2018 |
| WO | WO-2018083087 A2 | 5/2018 |
| WO | WO-2018201096 A1 | 11/2018 |
| WO | WO-2018204374 A1 | 11/2018 |
| WO | WO-2018208868 A1 | 11/2018 |
| WO | WO-2018218215 A1 | 11/2018 |
| WO | WO-2018222711 A2 | 12/2018 |

(56) References Cited

FOREIGN PATENT DOCUMENTS

WO  WO-2018222718 A1  12/2018
WO  WO-2018222722 A2  12/2018

OTHER PUBLICATIONS

Anonymous: "A Phase 1 Dose Escalation and Cohort Expansion Study of the Safety, Tolerability, and Efficacy of Anti-LAG-3 Monoclonal Antibody (BMS-986016) Administered Alone and in Combination With Anti-PD-1 Monoclonal Antibody (Nivolumab, BMS-936558) in Advanced Solid Tumors," ClinicaiTrials.gov Archive Identifier NCT01968109, accessed at https://clinicaltrials.gov/archive/NCT01968109/2014_01_23, last accessed on Jun. 12, 2015, 5 pages.
ATCC Product Data Sheet,"A3.4H2 (ATCC® HB-12319™)," American Type Culture Collections, 2013. 2 pages.
ATCC Product Data Sheet,"A3.6B10 (ATCC® HB-12318™)," American Type Culture Collections, 2013. 2 pages.
Baixeras, E., et al., "Characterization of the Lymphocyte Activation Gene 3-encoded Protein. A New Ligand for Human Leukocyte Antigen Class II Antigens," The Journal of Experimental Medicine 176(2):327-337, Rockefeller University Press, United States (Aug. 1992).
Blackburn, S.D., et al., "Coregulation of CD8+ T cell exhaustion by multiple inhibitory receptors during chronic viral infection," Nature immunology 10(1):29-37, Nature America Inc., United States (Jan. 2009).
Casati, C., et al., "Soluble Human LAG-3 Molecule Amplifies the in Vitro Generation of Type 1 Tumor-specific Immunity," Cancer Research 66(8):4450-4460, American Association for Cancer Research, United States (Apr. 2006).
Cashion, M.P. and Long, T.E., "Biomimetic Design and Performance of Polymerizable Lipids," Accounts of Chemical Research 42(8):1016-1025, American Chemical Society, United States (Aug. 2009).
Chelius, D., et al., "Identification and Characterization of Deamidation Sites in the Conserved Regions of Human Immunoglobulin Gamma Antibodies," Analytical Chemistry 77(18):6004-6011, American Chemical Society, United States (2005).
Cleland, J,L., et al., "The Development of Stable Protein Formulations: A Close Look at Protein Aggregation, Deamidation, and Oxidation," Critical Reviews in Therapeutic Drug Carrier Systems 10(4):307-377, CRC Press, United States (1993).
Correia, I,R., et al., "Stability of IgG Isotypes in Serum," mAbs 2(3):221-232, Taylor & Francis, United States (May-Jun. 2010).
De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).
Drake, C.G., et al., "Blocking the Regulatory T Cell Molecule LAG-3 Augments in Vivo Anti-tumor Immunity in an Autochthonous Model of Prostate Cancer," Journal of Clinical Oncology 24(18):2573 (Jun. 2006).
El Mir, S. and Triebel, F., "A Soluble Lymphocyte Activation Gene-3 Molecule Used as a Vaccine Adjuvant Elicits Greater Humoral and Cellular Immune Responses to Both Particulate and Soluble Antigens," Journal of Immunology 164(11):5583-5589, American Association of Immunologists, United States (Jun. 2000).
Extended European Search Report for EP Application No. 17177885, Hague, Netherlands, dated Nov. 17, 2017.
Extended European Search Report dated Feb. 23, 2017 in EP Patent Application No. 16197459.7, European Patent Office, Munich, Germany, 15 pages.
Fishwild, D.M., et al., "High-Avidity Human IgG Kappa Monoclonal Antibodies from a Novel Strain of Minilocus Transgenic Mice," Nature Biotechnology 14(7):845-851, Nature America Publishing, United States (1996).
Goding, S,R., et al., "Combination of Adoptive Cell Transfer, Anti-PD-L1 and Anti-LAG-3 Antibodies for the Treatment of Recurrent Tumors," Oncolmmunology 2(8), 4 pages (May 2013).
Grosso, J.F., et al., "LAG-3 Regulates CD8+ T Cell Accumulation and Effector Function in Murine Self- and Tumor-tolerance Systems," The Journal of Clinical Investigation 117(11):3383-3392, American Society for Clinical Investigation, United States (Nov. 2007).
Harris, R.J., et al., "Identification of Multiple Sources of Charge Heterogeneity in a Recombinant Antibody," Journal of chromatography. B, Biomedical Sciences and Applications 752(2):233-245, Elsevier, Netherlands (2001).
Huang, C,T., et al., "Role of LAG-3 in Regulatory T Cells," Immunity 21(4):503-513, Cell Press, United States (Oct. 2004).
Huard, B., et al., "Characterization of the Major Histocompatibility Complex Class II Binding Site on LAG-3 Protein," Proceedings of the National Academy of Sciences of the United States of America 94(11):5744-5749, National Academy of Sciences, United States (May 1997).
Huard, B., et al., "Cellular expression and tissue distribution of the humanLAG-3-encoded protein, an MHC class II ligand," Immunogenetics 39:213-217, Springer-Verlag, Germany (1994).
Huard, B., et al., "Lymphocyte-activation Gene 3/major Histocompatibility Complex Class II Interaction Modulates the Antigenic Response of CD4+ T Lymphocytes," European Journal of Immunology 24(12):3216-3221, Wiley-VCH, Germany (Dec. 1994).
Huard, B., et al., "T Cell Major Histocompatibility Complex Class II Molecules Down-regulate CD4+ T Cell Clone Responses Following LAG-3 Binding," European Journal of Immunology 26(5):1180-1186, Wiley-VCH, Germany (May 1996).
International Preliminary Report on Patentability and Written Opinion for Application Serial No. PCT/US2013/48999, dated Jan. 6, 2015, 7 pages.
International Preliminary Report on Patentability for Application No. PCT/US2009/053405, dated Feb. 15, 2011, 10 pages.
International Preliminary Report on Patentability for Application Serial No. PCT/US2014/056277, dated Mar. 22, 2016, 10 pages.
International Search Report and written opinion for International Application No. PCT/US2009/053405, ISA/US Alexandria, Virginia, dated Mar. 31, 2010, 15 pages.
International Search Report and Written Opinion for International Application No. PCT/US2013/48999, European patent office, Rijswijk, dated Sep. 23, 2013, 11 pages.
International Search Report and Written Opinion for International Application No. PCT/US2014/056277, European patent office, Rijswijk, dated Feb. 4, 2015, 15 pages.
International Search Report and Written Opinion for International Application No. PCT/US2015/012916, European patent office, Rijswijk, dated Jun. 23, 2015, 12 pages.
Iouzalen, N., et al., "LAP, A Lymphocyte Activation Gene-3 (LAG-3)-associated Protein That Binds to a Repeated EP Motif in the Intracellular Region of LAG-3, May Participate in the Downregulation of the CD3/TCR Activation Pathway," European Journal of Immunology 31(10):2885-2891, Wiley-VCH, Germany (Oct. 2001).
Kocak, E., et al., "Combination Therapy with Anti-CTL Antigen-4 and Anti-4-1BB Antibodies Enhances Cancer Immunity and Reduces Autoimmunity," Cancer Research 66(14):7276-7284, American Association for Cancer Research, United States (Jul. 2006).
Kosky, A,A., et al., "Multivariate Analysis of the Sequence Dependence of Asparagine Deamidation Rates in Peptides," Pharmaceutical Research 26(11):2417-2428, Kluwer Academic/Plenum Publishers, United states (Nov. 2009).
Kroon, D,J., et al., "Identification of Sites of Degradation in a Therapeutic Monoclonal Antibody by Peptide Mapping," Pharmaceutical Research 9(11):1386-1393, Kluwer Academic/Plenum Publishers, United states (Nov. 1992).
Lonberg, N., et al., "Antigen-specific Human Antibodies from Mice Comprising Four Distinct Genetic Modifications," Nature 368(6474):856-859, Nature Publishing Group, United States (Apr. 1994).

(56) References Cited

OTHER PUBLICATIONS

MacCallum, R.M., et al., "Antibody-antigen Interactions: Contact Analysis and Binding Site Topography," Journal of Molecular Biology 262(5):732-745, Academic Press, England (Oct. 1996).

Macon-Lemaitre, L. and Triebel, F., "The Negative Regulatory Function of the Lymphocyte-activation Gene-3 Co-receptor (CD223) on Human T Cells," Immunology 115(2):170-178, Blackwell Scientific Publications, England (Jun. 2005).

Pardoll, D., "Chapter 14-Dendritic Cells and Coregulatory Signals: Immune Checkpoint Blockade to Stimulate Immunotherapy," Cancer Immunotherapy Immune Suppression and Tumor Growth, pp. 257-275, Elsevier Inc., United States (2007).

Prigent, P., et al., "Lymphocyte Activation Gene-3 Induces Tumor Regression and Antitumor Immune Responses," European Journal of Immunology 29(12):3867-3876, Wiley-VCH, Germany (Dec. 1999).

Reply to Communication from the Examining Division dated Nov. 25, 2016 in European Application No. 13737946.7 filed on Jul. 2, 2013, pp. 115-119.

Robinson, N,E. and Robinson, A,B., "Molecular Clocks," Proceedings of the National Academy of Sciences of the United States of America 98(3):944-949, National Academy of Sciences, United states (Jan. 2001).

Subramanyam, M., et al., "Soluble Human Lymphocyte Activation Gene-3 Modulates Allospecific T Cell Responses," International Immunology 10(5):679-689, University Press, England (May 1998).

Supplementary European Search Report for EP Application No. 09807162.4, European Patent Office, Munich, Germany, dated Dec. 21, 2012, 9 pages.

Third Party Observation dated Oct. 7, 2016 for European Application No. 13737946.7 filed on Jul. 2, 2013, 17 pages.

Triebel, F., et al., "LAG-3, A Novel Lymphocyte Activation Gene Closely Related to CD4," The Journal of Experimental Medicine 171(5):1393-1405, Rockefeller University Press, United States (May 1990).

Triebel, F., "LAG-3: A Regulator of T-cell and DC Responses and its Use in Therapeutic Vaccination," Trends in Immunology 24(12):619-622, Elsevier Science Ltd., England (Dec. 2003).

Tsai, P,K., et al., "Origin of the Isoelectric Heterogeneity of Monoclonal Immunoglobulin h1B4," Pharmaceutical Research 10(11):1580-1586, Kluwer Academic/Plenum Publishers, United states (Nov. 1993).

Turnis, M,E., et al., "Combinatorial Immunotherapy: PD-1 May Not Be LAG-ing Behind Any More.," Oncoimmunology 1(7):1172-1174, Taylor & Francis, United States (Oct. 2012).

Vlasak, J., et al., "Identification and Characterization of Asparagine Deamidation in the Light Chain CDR1of a Humanized IgG1 Antibody," Analytical Biochemistry 392(2):145-154, Academic Press, United states (Sep. 2009).

Woo, S,R., et al., "Immune Inhibitory Molecules LAG-3 and PD-1 Synergistically Regulate T-cell Function to Promote Tumoral Immune Escape," Cancer Research 72(4):917-927, American Association for Cancer Research, United states (Feb. 2012).

Workman, C.J. and Vignali, D.A., "Negative Regulation of T Cell Homeostasis by Lymphocyte Activation Gene-3 (CD223)," Journal of Immunology 174(2):688-695, American Association of Immunologists, United States (Jan. 2005).

Workman, C.J., et al., "Phenotypic Analysis of the Murine Cd4-related Glycoprotein, CD223 (LAG-3)," European Journal of Immunology 32(8):2255-2263, Wiley-VCH, Germany (Aug. 2002).

Nivolumab, "Guide to Pharmacology," accessed at http://www.guidetopharmacology.org/GRAC/liganddisplayforward?ligandId=7335, last accessed Sep. 28, 2018, 1 page.

Burova, E., et al., "A novel anti-human LAG-3 antibody in combination with anti-human PD-1 (REGN2810) shows enhanced antitumor activity in PD-1 × LAG-3 dual-dehumanized mice and favorable pharmacokinetic and safety profiles in cynomolgus monkeys," Journal for Immunotherapy of Cancer 4(1):P195, BMJ Journals, United Kingdom (2016).

Liu, S-Y., et al., "Ongoing clinical trials of PD-1 and PD-L1 inhibitors for lung cancer in China," J Hematol 10:136, BMC, United Kingdom (2017).

Adib-Conquy, M., et al., "Effect of Amino Acid Substitutions in the Heavy Chain CDR3 of an Autoantibody on Its Reactivity," International Immunology 10(3):341-346, Oxford University Press, England (1998).

Beers, R., et al., "Immunotoxins With Increased Activity Against Epidermal Growth Factor Receptor vIII-expressing Cells Produced by Antibody Phage Display," Clinical Cancer Research 6(7):2835-2843, The Association, United States (2000).

Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (1993).

Camacho, L.H., et al., "Phase I clinical trial of anti-CTLA4 human monoclonal antibody CP-675,206 in patients (pts) with advanced solid malignancies," Journal of Clinical Oncology 22(14S):Abstract 2505, 2004 ASCO Annual Meeting Proceedings (Post-Meeting Edition), $40^{th}$ Annual Meeting, Jun. 5-8, New Orleans, LA, American Society of Clinical Oncology, United States (2004).

De Wildt, R.M.T., et al., "Heavy Chain CDR3 Optimization of a Germline Encoded Recombinant Antibody Fragment Predisposed to Bind the U1A Protein," Protein Engineering 10(7):835-841, Oxford University Press, England (1997).

Extended European Search Report for EP Application No. 09807162.4, European Patent Office, Netherlands, dated Dec. 21, 2012, 9 pages.

Greenberg, P.D. and Riddell, S.R., "Deficient Cellular Immunity-Finding and Fixing the Defects," Science 285(5427):546-551, American Association for the Advancement of Science, United States (1999).

Grosso, J.F., et al., "Functionally Distinct LAG-3 and PD-1 Subsets on Activated and Chronically Stimulated CD8 T Cells," The Journal of Immunology 182(11):6659-6669, The American Association of Immunologists, Inc., United States (Jun. 2009).

Hahne, M., et al., "Melanoma Cell Expression of Fas(Apo-1/CD95) Ligand: Implications for Tumor Immune Escape," Science 274(5291):1363-1366, American Association for the Advancement of Science, United States (1996).

Hall, B.L., et al., "A Single Amino Acid Mutation in CDR3 of the 3-14-9 L Chain Abolished Expression of the IDA 10-defined Idiotope and Antigen Binding," Journal of Immunology 149(5):1605-1612, American Association of Immunologists, United States (1992).

He, Y-F., et al., "Blocking Programmed Death-1 Ligand-PD-1 Interactions by Local Gene Therapy Results in Enhancement of Antitumor Effect of Secondary Lymphoid Tissue Chemokine," The Journal of Immunology 173(8):4919-4928, The American Association of Immunologists, United States (2004).

Holliger, P., et al., "'Diabodies': Small Bivalent and Bispecific Antibody Fragments," Proceedings of the National Academy of Sciences USA 90(14):6444-6448, National Academy of Sciences, United States (1993).

Howard, M. and Ogarra, A., "Biological Properties of Interleukin 10," Immunology Today 13(6):198-200, Elsevier Science Publishers, England (1992).

Hurwitz, A.A., et al., "CTLA-4 Blockade Synergizes With Tumor-derived Granulocytemacrophage Colony-stimulating Factor for Treatment of an Experimental Mammary Carcinoma," Proceedings of the National Academy of Sciences of the United States of America 95(17):10067-10071, National Academy of Sciences, United States (1998).

Hutloff, A., et al., "ICOS is an Inducible T-cell Co-stimulator Structurally and Functionally Related to CD28," Nature 397(6716):263-266, Nature Publishing Group, England (1999).

Ito, D., et al., "Effective Priming of Cytotoxic T Lymphocyte Precursors by Subcutaneous Administration of Peptide Antigens in Liposomes Accompanied by Anti-CD40 and Anti-CTLA-4 Antibodies," Immunobiology 201 (5):527-540, Elsevier, Netherlands (2000).

Kehrl, J.H., et al., "Production of Transforming Growth Factor β by Human T Lymphocytes and Its Potential Role in the Regulation of

(56) References Cited

OTHER PUBLICATIONS

T Cell Growth," The Journal of Experimental Medicine 163(5):1037-1050, Rockefeller University Press, United States (1986).
Kelley, R.F. and O'Connell, M.P., "Thermodynamic Analysis of an Antibody Functional Epitope," Biochemistry 32(27):6828-6835, American Chemical Society, United States (1993).
Komissarov, A.A., et al., "Site-specific Mutagenesis of a Recombinant Anti-single-stranded DNA Fab. Role of Heavy Chain Complementarity-determining Region 3 Residues in Antigen Interaction," 272(43):26864-26870, American Society for Biochemistry and Molecular Biology, United States (1997).
Melero, I., et al., "Monoclonal Antibodies Against the 4-1BB T-cell Activation Molecule Eradicate Established Tumors," Nature Medicine 3(6):682-685, Nature Publishing Company, United States (1997).
Mokyr, M.B., et al., "Realization of the Therapeutic Potential of CTLA-4 Blockade in Low-dose Chemotherapy-treated Tumor-bearing Mice," Cancer Research 58(23):5301-5304, American Association for Cancer Research, United States (1998).
Poljak, R.J., "Production and Structure of Diabodies," Structure 2(12):1121-1123, Cell Press, United States (1994).
Ridge J.P., et al., "A Conditioned Dendritic Cell Can Be a Temporal Bridge Between a CD4+ T-helper and a T-killer Cell," Nature 393(6684):474-478, Nature Publishing Group, England (1998).
Weinberg, A.D., et al., "Engagement of the OX-40 Receptor in Vivo Enhances Antitumor Immunity," Journal of Immunology 164(4):2160-2169, American Association of Immunologists, United States (2000).
Poirier, N., et al., "Antibody-mediated depletion of lymphocyte-activation gene-3 (LAG-3+)-activated T lymphocytes prevents delayed-type hypersensitivity in non-human primates" Clinical and Experimental Immunology 164(2):265-274, British Society for Immunology (2011).
Kallewaard, N.L., et al., "Functional Maturation of the Human Antibody Response to Rotavirus," Journal of Immunology 180(6):3980-3989, American Association of Immunologists, United States (Mar. 2008).
Wiens, G.D., et al., "Somatic Mutation in VH complementarity-determining Region 2 and Framework Region 2: Differential Effects on Antigen Binding and Ig selection," Journal of Immunology 159(3):1293-1302, American Association of Immunologists, United States (1997).
Khan, T., et al., "Adjustable locks and flexible Keys: Plasticity of Epitope-Paratope Interactions in Germline Antibodies," J Immunol 192:5398-5405, American Association of Immunologists, United States (2014).
Torres, Marcela, et al., "The Immunoglobulin constant region contributes to affinity and specificity," Trends in Immunology 29(2):91-97, Elsevier, Netherlands (2007).
Poosarla, V.G., et al., "Computational De Novo Design of Antibodies Binding to a Peptide With High Affinity," Biotechnology and Bioengineering 114(6):1331-1342, Wiley Online Library, United States (2017).
Edwards, B.M., et al., "The Remarkable Flexibility of the Human Antibody Repertoire; Isolation of Over One Thousand Different Antibodies to a Single Protein," J. Mol. Biol. 334:103-118, Elsevier, Netherlands (2003).
Barber, D.L., et al., "Restoring function in exhausted CD8 T cells during chronic viral infection," Nature 439:682-687, Nature Publishing Group, United Kingdom (2006).
Declaration of Jeanette L. Fairhurst in Grounds of Opposition mailed Aug. 20, 2020 in EP Application No. 1516647.8, European Patent Office, Germany, 12 pages.
Dyrberg, T., et al., "Peptides as antigens. Importance of orientation," The Journal of Experimental Medicine 164(4):1344-1349, Rockefeller University Press, United States (1986).
Exhibit 1 in Grounds of Opposition mailed Aug. 20, 2020, in EP Application No. 15156647.8, European Patent Office, Germany, 1 page.
Extended European Search Report dated Jul. 13, 2015, in EP Application No. 15156647.8, European Patent Office, Germany, 9 pages.

Goldberg, M.V., et al., "LAG-3 in Cancer Immunotherapy," Curr Top Microbiol Immunology 344:269-278, Springer, United States (2011).
Grounds of Opposition mailed Aug. 20, 2020, in EP Application No. 1516647.8, European Patent Office, Germany, 86 pages.
Hong, S., et al., "Progress and Application of Humanization of Monoclonal Antibodies," Chinese Journal of Biologicals 21(1):70-73, Changchun Institute of Biological Products, China (2008).
Hoogenboom, H.R., et al., "Designing and optimizing library selection strategies for generating high-affinity antibodies," TibTech Library 15:62-70, Elsevier, Netherlands (1997).
Huard, B., et al., "CD4/major histocompatibility complex class II interaction analyzed with CD4- and lymphocyte activation gene-3 (LAG-3)-Ig fusion proteins," Eur. J. Immunol.25:2718-2721, Wiley-VCH, Germany (1995).
Huard, B., et al., "LAG-3 does not define a specific mode of natural killing in human," Immunology Letters 61:109-112, Elsevier, Netherlands (1998).
Imakiire, T., et al., "Generation, immunologic characterization and antitumor effects of human monoclonal antibodies for carcinoembryonic antigen," Int J Cancer 108(4):564-570, Wiley Online Publishing, United States (2004).
Jespers, L.S., et al., "Guiding the Selection of Human Antibodies from Phage Display Reperotires to a Single Epitope of an Antigen," Biotechnology 12:899-903, Nature Publishing Group, United Kingdom (1994).
Kaufmann, D.E., et al., "Upregulation of CTLA-4 by HIV-specific CD4+ T cells correlates with disease progression and defines a reversible immune dysfunction," Nature Immunology 8(11): 1246-1254, Nature Publishing Group, United Kingdom (2007).
Response to communication in European Patent Application No. 15156647.8, dated Mar. 29, 2018, European Patent Office, Germany, 3 pages.
Response to communication in European Patent Application No. 15156647.8, dated Feb. 9, 2016, European Patent Office, Germany, 3 pages.
Perez De La Lastra, J.M., et al., "Epitope mapping of 10 monoclonal antibodies against the pig analogue of human membrane cofactor protein (MCP)," Immunology 96:663-670, Blackwell Science Ltd., United States (1999).
Shapira, M., et al., "Immunity and protection against influenza virus by synthetic peptide corresponding to antigenic sites of hemag-glutinin," PNAS 81(8): 2461-2465, United States National Academy of Sciences, United States (1984).
Office Action dated Apr. 28, 2020 in CN 201710463804.9, State Intellectual Property Office of People's Republic of China, China, 8 pages.
Tanaka, T., et al., "Efficient generation of antibodies to oncoproteins by using synthetic peptide antigens," PNAS 82(10):3400-3404, United States National Academy of Sciences, United States (1985).
Workman, C.J., et al., "The CD4-related molecule, LAG-3 (CD223), regulates the expansion of activated T cells," Eur J. Immunol. 33(4):970-979, Wiley Online Library, United States (2003).
Agata, Y., et al., "Expression of the PD-1 Antigen on the Surface of Stimulated Mouse T and B lymphocytes," International Immunology 8(5):765-772, Oxford University Press, England (May 1996).
Bennett, F., et al., "Program Death-1 Engagement Upon TCR Activation has Distinct Effects on Costimulation and Cytokine-driven Proliferation: Attenuation of ICOS, IL-4, and IL-21, but not CD28, IL-7, and IL-15 responses," The Journal of Immunology 170(2):711-718, The American Association of Immunologists, United States (Jan. 2003).
Bird, R.E., et al., "Single-chain Antigen-binding Proteins," Science 242(4877):423-426, Association for the Advancement of Science, United States (Oct. 1988).
Blank, C., et al., "Interaction of PD-L1 on Tumor Cells with PD-1 on Tumor-specific T Cells as a Mechanism of Immune Evasion: Implications for Tumor Immunotherapy," Cancer Immunology Immunotherapy 54(4):307-314, Springer-Verlag, Germany (Apr. 2005).
Brown, J.A., et al., "Blockade of Programmed Death-1 Ligands on Dendritic Cells Enhances T Cell Activation and Cytokine Produc-

(56) References Cited

OTHER PUBLICATIONS tion," The Journal of Immunology 170(3):1257-1266, The American Association of Immunologists, United States (Feb. 2003).
Camisaschi, C., et al., "LAG-3 Expression Defines a Subset of CD4(+)CD25(High)Foxp3(+) Regulatory T Cells That Are Expanded at Tumor Sites," Journal of Immunology 184(11):6545-6551, American Association of Immunologists, United states (Jun. 2010).
Carter, L.L., et al., "PD-1:PD-L Inhibitory Pathway Affects both CD4(+) and CD8(+) T Cells and is Overcome by IL-2," European Journal of Immunology 32(3):634-643, WILEY-VCH Verlag GmbH, German (Mar. 2002).
Daugherty, A.L. and Mrsny, R.J., "Formulation and Delivery Issues for Monoclonal Antibody Therapeutics," Advanced Drug Delivery Reviews 58(5-6):686-706, Elsevier Science Publishers, Netherlands (2006).
Dong, H. and Chen, L., "B7-H1 Pathway and its Role in the Evasion of Tumor Immunity," Journal of Molecular Medicine 81(5):281-287, Springer, Germany (May 2003).
Dong, H., et al., "B7-H1, a Third Member of the B7 Family, Co-stimulates T-cell Proliferation and Interleukin-10 Secretion," Nature Medicine 5(12):1365-1369, Nature America, United States (Dec. 1999).
Dong, H., et al., "Tumor-associated B7-H1 Promotes T-cell Apoptosis: A Potential Mechanism of Immune Evasion," Nature Medicine 8(8):793-800, Nature Publishing Company, United States (Aug. 2002).
Freeman, G.J., et al., "Engagement of the PD-1 Immunoinhibitory Receptor by a Novel B7 Family Member Leads to Negative Regulation of Lymphocyte Activation," The Journal of Experimental Medicine 192(7):1027-1034, The Rockefeller University Press, United States (Oct. 2000).
Freeman, G.J., et al., "Protect the Killer: CTLs Need Defenses against the Tumor," Nature Medicine 8(8):787-789, Nature Publishing Company, United States (Aug. 2002).
GenBank, "Human hPD-1 (hPD-1) mRNA, complete cds," Accession No. U64863.1, accessed on https://www.ncbi.nlm.nih.gov/nuccore/U64863, Oct. 12, 2005.
GenBank, "lymphocyte activation gene 3 protein precursor [*Homo sapiens*]," Accession No. NP_002277.4, accessed on https://www.ncbi.nlm.nih.gov/protein/NP_002277, Oct. 6, 2016.
GenBank, "lymphocyte activation gene 3 protein precursor [Mus musculus]," Accession No. NP 032505.1, accessed on https://www.ncbi.nlm.nih.gov/protein/NP032505, Feb. 15, 2015.
GenBank, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Accession No. Q9NZQ7.1, accessed on https://www.ncbi.nlm.nih.gov/protein/Q9NZQ7, Nov. 2, 2016.
GenBank, "RecName: Full=Programmed cell death 1 ligand 2; Short=PD-1 ligand 2; Short=PD-L2; Short=PDCD1 ligand 2; Short=Programmed death ligand 2; AltName: Full=Butyrophilin B7-DC; Short=B7-DC; AltName: CD_antigen=CD273; Flags: Precursor," Accession No. Q9BQ51.2, accessed on https://www.ncbi.nlm.nih.gov/protein/Q9BQ51, Feb. 10, 2021.
Gorelik, L., et al., Preclinical Characterization of a Novel Fully Human IgG1 anti-PD-L1 mAb CK-301, American Association for Cancer Research Annual Meeting (AACR), Abstract 4606 (Apr. 2016).
Hamid, O., et al., "Safety and Tumor Responses with Lambrolizumab (Anti-Pd-1) in Melanoma," The New England Journal of Medicine 369(2):134-144, Massachusetts Medical Society, United States of America (Jul. 2013).
Hansen, J.A., et al., "Monoclonal Antibodies Identifying a Novel T-cell Antigen and Ia Antigens of Human Lymphocytes," Immunogenetics 10:247-260, Springer-Verlag (Feb. 1980).
Herbst, R.S., et al., "A Study of MPDL3280A, an Engineered PD-L1 Antibody in Patients with Locally Advanced or Metastatic Tumors," Journal of Clinical Oncology 31(Suppl):Abstract 3000, American Society of Clinical Oncology, United States (2013).

Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences USA 85(16):5879-5883, National Academy of Sciences, United States (Aug. 1988).
International Search Report and Written Opinion for International Application No. PCT/US2018/035142, European Patent Office, Netherlands, dated Jan. 22, 2019.
Ishida, Y., et al., "Induced Expression of PD-1, a Novel Member of the Immunoglobulin Gene Superfamily, Upon Programmed Cell Death," The EMBO Journal 11 (11):3887-3895, Oxford University Press, England (Nov. 1992).
Iwai, Y., et al., "Involvement of PD-L1 on Tumor Cells in the Escape from Host Immune System and Tumor Immunotherapy by PD-L1 Blockade," Proceedings of the National Academy of Sciences 99(19):12293-12297, The National Academy of Sciences of the United States (Sep. 2002).
Keir, M,E., et al., "PD-1 and Its Ligands in Tolerance and Immunity," Annual Review of Immunology 26:677-704, Annual Reviews Inc, United states (2008).
Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).
Konishi, J., et al., "B7-H1 Expression on Non-small Cell Lung Cancer Cells and its Relationship with Tumor-infiltrating Lymphocytes and their PD-1 Expression," Clinical Cancer Research 10(15):5094-5100, American Association for Cancer Research, United States (Aug. 2004).
Latchman, Y., et al., "PD-L2 is a Second Ligand for PD-1 and Inhibits T Cell Activation," Nature Immunology 2(3):261 -268, Nature Publishing Group, United States (Mar. 2001).
NCI Drug Dictionary, anti-PD-1 monoclonal antibody MEDI0680, accessed on Dec. 1, 2016, retrieved from the Internet URL: https://www.cancer.gov/publications/dictionaries/cancer-drug?cdrid=756047.
NCI Drug Dictionary, pembrolizumab, accessed on Dec. 1, 2016, retrieved from the Internet URL: https://www.cancer.gov/drugdictionary?cancer-drug?cdrid=695789, 3 pages.
Nielsen, C., et al., "A putative regulatory polymorphism in PD-1 is associated with nephropathy in a population-based cohort of systemic lupus erythematosus patients," Lupus 13(7):510-516, SAGE, England (2004).
Nishimura, H., et al., "Autoimmune Dilated Cardiomyopathy in PD-1 Receptor-deficient Mice," Science 291 (5502):319-322, American Association for the Advancement of Science, United States (Jan. 2001).
Nishimura, H., et al., "Development of Lupus-like Autoimmune Diseases by Disruption of the PD-1 Gene Encoding an ITIM Motif-carrying Immunoreceptor," Immunity 11(2):141-151, Cell Press, United States (Aug. 1999).
Okazaki, T., et al., "New Regulatory Co-receptors: Inducible co-stimulator and PD-1," Current Opinion in Immunology 14(6):779-782, Elsevier, England (Dec. 2002).
Okazaki, T., et al., "PD-1 immunoreceptor Inhibits B Cell Receptor-mediated Signaling by Recruiting src Homology 2-domain-containing Tyrosine Phosphatase 2 to Phosphotyrosine," Proceedings of the National Academy of Sciences 98(24):13866-13871, National Academy of Sciences, United States (Nov. 2001).
Pardoll, D.M., "The Blockade of Immune Checkpoints in Cancer Immunotherapy," Nature Reviews Cancer 12(4):252-264, Nature Publishing Group, England (Mar. 2012).
Prokunina, L. and Alarcon-Riquelme, M., "The Genetic Basis of Systemic Lupus Erythematosus-knowledge of Today and Thoughts for Tomorrow," Human Molecular Genetics 13(1):R143-R148, Oxford University Press, England (Apr. 2004).
Salama, A.D., et al., "Critical Role of the Programmed Death-1 (PD-1) Pathway in Regulation of Experimental Autoimmune Encephalomyelitis," The Journal of Experimental Medicine 198(1):71-78, The Rockefeller University Press, United States (Jul. 2003).

(56) References Cited

OTHER PUBLICATIONS

Terme, M., et al., "IL-18 Induces PD-1-dependent Immunosuppression in Cancer," Cancer Research 71(16):5393-5399, American Association for Cancer Research, United States (Aug. 2011).
Thomas, M.L., "Of ITAMs and ITIMs: Turning on and off the B Cell Antigen Receptor," The Journal of Experimental Medicine 181 (6):1953-1956, The Rockefeller University Press, United States (Jun. 1995).
Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).
Vivier, E. and Daeron, M., "Immunoreceptor Tyrosine-based Inhibition Motifs," Immunology Today 18(6):286-291, Elsevier, England (Jun. 1997).
Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).
Workman, C,J., et al., "LAG-3 Regulates Plasmacytoid Dendritic Cell Homeostasis," Journal of Immunology 182(4):1885-1891, American Association of Immunologists, United states (Feb. 2009).
Brahmer, J.R., et al., "Safety and Activity of Anti-PD-L1 Antibody in Patients with Advanced Cancer," The New England Journal of Medicine 366(26):2455-2465, Massachusetts Medical Society, United States (2012).
Brahmer., J.R., et al., "Phase I Study of Single-agent Anti-programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (2010).
ClinicalTrials.gov, "Safety Study of Anti-LAG-3 in CLL, HL and NHL," Identifier NCT02061761, accessed at https://clinicaltrials.gov/archive/NCT02061761/2014_08_28, last accessed on Jan. 13, 2015, 4 pages.
ClinicalTrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_06_20, last accessed on Jan. 13, 2015, 4 pages.
Drake, C.G., et al., "Breathing New Life into Immunotherapy: Review of Melanoma, Lung and Kidney Cancer," Nature Reviews Clinical Oncology 11(1):24-37, Nature Pub. Group, England (2014).
Gillam, W.A., et al., "A phase I study of IMP321 and Gemcitabine as the Front-Line Therapy in Patients with Advanced Pancreatic Adenocarcinoma," Investigational New Drugs 31(3):707-713, Springer, United States (2013).
Haycock,G,B., et al., "Geometric Method for Measuring Body Surface Area: a Height-weight Formula Validated in Infants, Children, and Adults," The Journal of Pediatrics 93(1):62-66, Mosby, United states (1978).
Hemon, P., et al., "MHC Class II Engagement by its Ligand LAG-3 (CD223) Contributes to Melanoma Resistance to Apoptosis," Journal of Immunology 86(9):5173-5183, American Association of Immunologists, United States (2011).
Lipson, E.J., et al., "Durable Cancer Regression Off-treatment and Effective Reinduction Therapy with an Anti-PD-1 Antibody," Clinical Cancer Research 19(2):462-468, The Association, United States (2013).
ONO Pharmaceutical Co., Ltd, A fully human anti-PD-1 antibody "ONO-4538/BMS-936558", Results from Phase 1 Study in Cancer Patients Published in New England Journal of Medicine (NEJM) and Presented at Annual Meeting of the American Society of Clinical Oncology (ASCO), Jun. 4, 2012, [retrieved on May 24, 2018], Retrieved from the Internet: (URL:https://www.ono.co.jp/jpnw/PDF/n12_0604.pdf), Jun. 12, 2018, with translator certification statement, 8 pages.
Rosenberg, S.A., et al., "Cancer Immunotherapy in Cancer: Principles & Practice of Oncology", 332-344, Lippincott Williams & Wilkins (2011).

Sierro et al., "The CD4-Like Molecule LAG-3, Biology and Therapeutic Applications," Expert Opinion on Therapeutic Targets, 15(1):91-101, Taylor & Francis, United States (2010).
Wolchok, J.D., et al., "Guidelines for the Evaluation of Immune Therapy Activity in Solid Tumors: Immune-related Response Criteria," Clinical Cancer Research 15(23)7412-7420, The Association, United States (2009).
Wolchok, J.D., et al., "Nivolumab Plus Ipilimumab in Advanced Melanoma," The New England Journal of Medicine 369(2):122-133, Massachusetts Medical Society, United States (2013).
ClinicalTrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_01_23, 5 pages.
Co-Pending U.S. Appl. No. 16/108,973, inventor Korman; Alan. J., filed Aug. 22, 2018 (Unpublished).
ClinicalTrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_05_07, last accessed on Feb. 10, 2021, 4 pages.
Anonymous: "History of Changes for Study: NCT00730639, A Phase 1b Study of MDX-1106 in Subjects With Advanced or Recurrent Malignancies (MDX1106-03)," ClinicalTrials.gov Archive, accessed at https://clinicaltrials.gov/ct2/history/NCT00730639?V_8=View, accessed on Feb. 5, 2021, 10 pages.
Ansell, S.M., et al., "Epstein-Barr Virus Infection in Richter's Transformation," American Journal of Hematology 60(2):99-104, Wiley-Blackwell, United States (1999).
Berrien-Elliott, M.M., et al., "Durable Adoptive Immunotherapy for Leukemia Produced by Manipulation of Multiple Regulatory Pathways of CD8+ T-cell Tolerance," Cancer Research 73(2):605-616, American Association for Cancer Research, United States (2013).
Cheson, B.D., et al., "Revised Response Criteria for Malignant Lymphoma," Journal of Clinical Oncology 25(5):579-586, American Society of Clinical Oncology, United States (2007).
Dickinson, J.D., et al., "11q22.3 Deletion in B-chronic Lymphocytic Leukemia is Specifically Associated with Bulky Lymphadenopathy and ZAP-70 Expression but Not Reduced Expression of Adhesion/cell Surface Receptor Molecules," Leukemia & Lymphoma 47(2):231-244, Informa Healthcare, England (2006).
Dolcetti, R. and Carbone, A., "Epstein-barr Virus Infection and Chronic Lymphocytic Leukemia: A Possible Progression Factor," Infectious Agents and Cancer 5:22, BioMed Central, England (2010).
Fujimoto, S., et al., "Studies on the Physical Surface Area of Japanese. 18. Calculation Formulas in Three Stages Over All Ages," Nihon Eiseigaku Zasshi 23(5):443-450, Nippon Eisei Gakkai,Japan (1968).
Genbank, "Predicted: Macaca mulatta lymphocyte-activation gene 3 (LAG3), transcript variant X1, mRNA," accessed at https://www.ncbi.nlm.nih.gov/nuccore/XM_001108923/, accessed on May 21, 2018.
Green, M.R., et al., "Constitutive AP-1 Activity and EBV Infection Induce PD-L1 in Hodgkin Lymphomas and Posttransplant Lymphoproliferative Disorders: Implications for Targeted Therapy," Clinical Cancer Research 18(6):1611-1618, The Association, United States (2012).
Hallek, M., et al., "Guidelines for the Diagnosis and Treatment of Chronic Lymphocytic Leukemia: a Report From the International Workshop on Chronic Lymphocytic Leukemia Updating the National Cancer Institute-working Group 1996 Guidelines," Blood 111(12):5446-5456, American Society of Hematology, United States (2008).
Kanakry, J.A., et al., "Plasma Epstein-barr Virus Dna Predicts Outcome in Advanced Hodgkin Lymphoma: Correlative Analysis From a Large North American Cooperative Group Trial," Blood 121(18):3547-3553, American Society of Hematology, United States (2013).
Kotaskova, J., et al., "High Expression of Lymphocyte-activation Gene 3 (LAG3) in Chronic Lymphocytic Leukemia Cells Is Associated With Unmutated Immunoglobulin Variable Heavy Chain Region (IGHV) Gene and Reduced Treatment-free Survival," The

(56) References Cited

OTHER PUBLICATIONS

Journal of Molecular Diagnostics 12(3):328-334, American Society for Investigative Pathology and the Association for Molecular, United States (2010).
Manuel, M., et al., "Lymphopenia Combined With Low TCR Diversity (Divpenia) Predicts Poor Overall Survival in Metastatic Breast Cancer Patients," Oncoimmunology 1(4):432-440, Taylor & Francis, United States (2012).
Monti, S., et al., "Molecular Profiling of Diffuse Large B-cell Lymphoma Identifies Robust Subtypes Including One Characterized by Host Inflammatory Response," Blood 105(5):1851-1861, American Society of Hematology, United States (2005).
Tsimberidou, A.M., et al., "Epstein-barr Virus in Patients With Chronic Lymphocytic Leukemia: a Pilot Study," Leukemia & Lymphoma 47(5):827-836, Informa Healthcare, England (2006).
Zhang, J., et al., "Using Gene Co-expression Network Analysis to Predict Biomarkers for Chronic Lymphocytic Leukemia," BMC Bioinformatics 11(9):S5, BioMed Central, England (Oct. 2010).
Lipson, E., et al., "Initial experience administering BMS-986016, a monoclonal antibody that targets lymphocyte activation gene (LAG)-3, alone and in combination with nivolumab to patients with hematologic and solid malignancies", Journal for ImmunoTherapy of Cancer, 4(Suppl 1):P232 (Nov. 2016).
Mathijssen, R.H., et al., "Flat-Fixed Dosing Versus Body Surface Area Based Dosing of Anticancer Drugs in Adults: Does It Make a Difference??," Oncologist, 12(8):913-923, AlphaMed Press, United States (2007).
Huang, R.-Y., et al., "LAG3 and PD1 Co-Inhibitory Molecules Collaborate to Limit CD8+ T Cell Signaling and Dampen Antitumor Immunity in a Murine Ovarian Cancer Model," Oncotarget, 6(29):27359-27377 (2015).
Xiao Y and Freeman G.J., "The Microsatellite Instable Subset of Colorectal Cancer Is a Particularly Good Candidate for Checkpoint Blockade Immunotherapy," Cancer Discovery 5(1):16-18, American Association for Cancer Research, United States (Jan. 2015).
Zhang, F., et al., "Structural Basis of a Novel PD-L1 Nanobody for Immune Checkpoint Blockade," Cell Discovery, 3:17004, Nature Publishing Group, England (Mar. 2017).
Ascierto, P.A., et al., "Initial Efficacy of Anti-lymphocyte Activation Gene-3 (Anti-LAG-3; BMS-986016) in Combination With Nivolumab (Nivo) in Pts With Melanoma (MEL) Previously Treated With Anti-PD-1/PD-L1 Therapy," Journal of Clinical Oncology 35(15_suppl):[abstract 9520], American Society of Clinical Oncology, United States (May 2017).
Bettini, M., et al., "Cutting Edge: Accelerated Autoimmune Diabetes in the Absence of LAG-3," Journal of Immunology 187(7):3493-3498, American Association of Immunologists, United States (Oct. 2011).
Condeelis, J. and Weissleder, R., "In Vivo Imaging in Cancer," Cold Spring Harbor Perspectives in Biology 2(12):a003848, Cold Spring Harbor Laboratory Press, United States (Dec. 2010).
Gandhi, M,K., et al., "Expression of LAG-3 by Tumor-infiltrating Lymphocytes Is Coincident With the Suppression of Latent Membrane Antigen-specific CD8+ T-cell Function in Hodgkin Lymphoma Patients," Blood 108(7):2280-2289, American Society of Hematology, United States (Oct. 2006).
Goding, S,R., et al., "Restoring Immune Function of Tumor-specific CD4+ T Cells During Recurrence of Melanoma," Journal of Immunology 190(9):4899-4909, American Association of Immunologists, United states (May 2013).
Liu, S.Y., et al., "Ongoing Clinical Trials of PD-1 and PD-L1 Inhibitors for Lung Cancer inChina," Journal of Hematology & Oncology, 10(1):136, Biomed Central, England (Jul. 2017).
Llosa, N.J., et al., "The Vigorous Immune Microenvironment of Microsatellite Instable Colon Cancer Is Balanced by Multiple Counter-inhibitory Checkpoints," Cancer Discovery 5(1):43-51, American Association for Cancer Research, United States (Jan. 2015).
Lyford-Pike, S., et al., "Evidence for a Role of the PD-1:PD-L1 Pathway in Immune Resistance of HPV-associated Head and Neck Squamous Cell Carcinoma," Cancer Research 73(6):1733-1741, American Association for Cancer Research, United States (Mar. 2013).
Matsuzaki, J., et al., "Tumor-infiltrating NY-ESO-1-specific CD8+ T Cells Are Negatively Regulated by LAG-3 and PD-1 in Human Ovarian Cancer," Proceedings of the National Academy of Sciences of the United States of America 107(17):7875-7880, National Academy of Sciences, United states (Apr. 2010).
McCabe, K.E. and Wu, A.M., "Positive Progress in ImmunoPET—not Just a Coincidence," Cancer Biotherapy & Radiopharmaceuticals 25(3):253-261, Mary Ann Liebert, Inc, United States (Jun. 2010).
Monette, A., et al., "Immune-enriched NSCLC biopsy tissue microarrays demonstrate that proliferating and checkpoint expressing TIL correlate with positive outcome," Journal for immunotherapy of Cancer 4(1): 58, BMJ Journals, United Kingdom (Nov. 2016).
NCI Drug Dictionary, anti-PD-1 Fusion Protein AMP-224, accessed on Dec. 1, 2016, retrieved from the Internet URL: https://www.cancer.gov/publications/dictionaries/cancer-drug?cdrid=700595.
Okazaki, T., et al., "PD-1 and LAG-3 Inhibitory Co-receptors Act Synergistically to Prevent Autoimmunity in Mice," The Journal of Experimental Medicine 208(2):395-407, Rockefeller University Press, United states (Feb. 2011).
Olafsen, T., et al., "ImmunoPET Imaging of B-Cell Lymphoma Using 124I-Anti-CD20 scFv Dimers (Diabodies)," Protein Engineering, Design & Selection 23(4):243-249, Oxford University Press, England (Apr. 2010).
Orchard G.E and Calonje E., "The Effect of Melanin Bleaching on Immunohistochemical Staining in Heavily Pigmented Melanocytic Neoplasms," The American Journal of Dermatopathology 20(4):357-361, Lippincott Williams & Wilkins, United States (Aug. 1998).
Shen W and Wu W., "Study of Melanin Bleaching After Immunohistochemistry of Melanincontaining Tissues," Applied immunohistochemistry & molecular morphology: AIMM 23(4):303-307, Lippincott Williams & Wilkins, United States (Apr. 2015).
Sierro, S., et al., "The CD4-like Molecule LAG-3, Biology and Therapeutic Applications," Expert Opinion on Therapeutic Targets 15(1):91-101, Informa Healthcare, England (Jan. 2011).
Sweis R., et al., "Molecular Drivers of the Non-T Cell-Inflamed Tumor Microenvironment in Urothelial Bladder Cancer," Cancer Immunology Research 4(7): 563-568, American Association for Cancer Research, United States (Jul. 2016).
Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).
Wherry, E.J., "T Cell Exhaustion," Nature Immunology 12(6):492-499, Nature America Inc, United States (2011).
Patel, S.P., et al., "PD-L1 Expression as a Predictive Biomarker in Cancer Immunotherapy," Molecular Cancer Therapeutics 14(4): 847-856 (2015).
Capelle, M.A.H., et al., "High Throughput Screening of Protein Formulation Stability: Practical Considerations," European J. of Pharm. & Biopharm. 65: 131-148 (2006).
Dudgeon, K., et al., "General strategy for the generation of human antibody variable domains with increased aggregation resistance," PNAS 109: 10879-10884 (2012).
Kayser, V., et al., "A screening tool for therapeutic monoclonal antibodies: Identifying the most stable protein and its best formulation based on thioflavin T binding," Biotechnology Journal 7: 127-132 (2012).
Wang, X., et al., "Potential aggregation prone regions in biotherapeutics," mAb 1:3, 254-67 (2009).
U.S. Food Drug Administration, "Highlights of Prescribing Information, OPDIVO (nivolumab) injection, for intravenous use," Reference ID: 3710966, U.S. FDA, 27 pages (2015).
Anonymous, "Relatlimab/Nivolumab Combo Active in Melanoma After PD-1/PD-L1 Therapy," Jan. 1, 2017, accessed at https://www.onclive.com/printer?url=/web-exclusives/relatlimabnivolumab-combo-active-in-melanoma-after-pd1dl1-therapy, accessed on Oct. 12, 2019, 2 pages.
Camisachi, C., et al., "Alternative activation of human plasmacytoid DCs in vitro and in melanoma lesions: involvement of LAG-3,"

(56) References Cited

OTHER PUBLICATIONS

Journal of Investigative Dermatology 134:1893-1902, Society of Investigative Dermatology, United States (2014).

Huang, R.Y., et al., "Compensatory upregulation of PD-1, LAG-3, and CTLA-4 limits the efficacy of single-agent checkpoint blockade in metastatic ovarian cancer," Oncoimmunology 6(1):e1249561, Taylor & Francis, United Kingdom (2016).

Lambert, J., "2017 ASCO Annual Meeting Preview and Education Program Highlights," Connection.ASCO.org, accessed at https://connection.asco.org/magazine/features/2017-asco-annual-meeting-preview-and-education-program-highlights, published Mar. 2, 2017, accessed on Aug. 31, 2021, 10 pages.

Lunter, P. and Champ, T., email, "RE: Publication date of J. Clin. Oncol. 35, No. 15 (supplement)," Aug. 2021, 2 pages.

Xu-Monette, Z.Y., et al., "PD-1 expression and clinical PD-1 blockade in B-cell lymphomas," Blood 131(1):68-83, American Society of Hematology, United States (2018).

Zhang, Y., et al., "[Novel immunotherapeutic anti-Hugh for anti-cancer targets]," BIT's 1st Annual International Congress of Genetics, China (2016).

English Machine Translation of Zhang, Y., et al., "[Novel immunotherapeutic anti-Hugh for anti-cancer targets]," BIT's $1^{st}$ Annual International Congress of Genetics, China (2016).

Ascierto, P.A., et al., "Efficacy of BMS-986016, a monoclonal antibody that targets lymphocyte activation gene 3 (LAG-3), in combination with nivolumab in pts with melanoma who progressed during prior anti-PD-1/PD-L1 therapy (mel prior IO) in all-comer and biomarker-enriched populations," Annals of Oncology 28(S5):LBA18, Elsevier, Netherlands (Sep. 2017).

Kang, Y.K., et al., "Nivolumab in patients with advanced gastric or gastro-oesophageal junction cancer refractory to, or intolerant of, at least two previous chemotherapy regimens (ONO-4538-12, Attraction-2): a randomised, double-blind, placebo-controlled, phase 3 trial," Lancet 390: 2461-2471, Elsevier, Netherlands (Oct. 2017).

Taieb, J., et al., "Evolution of checkpoint inhibitors for the treatment of metastatic gastric cancers: Current status and future perspectives," Cancer Treatment Reviews 66:104-113, Elsevier, Netherlands (May 2018).

Turnis, M.E., et al., "Inhibitory receptors as targets for cancer immunotherapy," Eur. J. Immunol. 45:1892-1905, Wiley, United States (2015).

* cited by examiner

SEQUENCE LISTING

```
<160> NUMBER OF SEQ ID NOS: 32

<210> SEQ ID NO 1
<211> LENGTH: 447
<212> TYPE: PRT
<213> ORGANISM: artificial sequence
<220> FEATURE:
<223> OTHER INFORMATION: Heavy Chain Amino Acid Sequence; Anti-LAG-3 mAb
      (BMS-986016)

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                    165                 170                 175
Leu Gln Ser Ser Gly Leu Tyr Ser Leu Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 2
<211> LENGTH: 214
<212> TYPE: PRT
<213> ORGANISM: artificial sequence
<220> FEATURE:
<223> OTHER INFORMATION: Light Chain Amino Acid Sequence; Anti-LAG-3 mAb
      (BMS-986016)

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Arg Ser Asn Trp Pro Leu
                 85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 3
<211> LENGTH: 120
<212> TYPE: PRT
<213> ORGANISM: artificial sequence
<220> FEATURE:
<223> OTHER INFORMATION: Heavy Chain Variable Region (VH) Amino Acid
      Sequence; Anti-LAG-3 mAb (BMS-986016)

<400> SEQUENCE: 3

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120
```

<210> SEQ ID NO 4
<211> LENGTH: 360
<212> TYPE: DNA
<213> ORGANISM: artificial sequence
<220> FEATURE:
<223> OTHER INFORMATION: Heavy Chain Variable Region (VH) Nucleotide
      Sequence; Anti-LAG-3 mAb (BMS-986016)

<400> SEQUENCE: 4

```
caggtgcagc tacagcagtg gggcgcagga ctgttgaagc cttcggagac cctgtccctc      60
acctgcgctg tctatggtgg gtccttcagt gattactact ggaactggat ccgccagccc     120
ccagggaagg ggctggagtg gattggggaa atcaatcatc gtggaagcac caactccaac     180
```

```
ccgtccctca agagtcgagt caccctatca ctagacacgt ccaagaacca gttctccctg    240
aagctgaggt ctgtgaccgc cgcggacacg gctgtgtatt actgtgcgtt tggatatagt    300
gactacgagt acaactggtt cgaccccctgg ggccagggaa ccctggtcac cgtctcctca    360
```

<210> SEQ ID NO 5
<211> LENGTH: 107
<212> TYPE: PRT
<213> ORGANISM: artificial sequence
<220> FEATURE:
<223> OTHER INFORMATION: Light Chain Variable Region (VL) Amino Acid
      Sequence; Anti-LAG-3 mAb (BMS-986016)

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys
            100                 105

<210> SEQ ID NO 6
<211> LENGTH: 321
<212> TYPE: DNA
<213> ORGANISM: artificial sequence
<220> FEATURE:
<223> OTHER INFORMATION: Light Chain Variable Region (VL) Nucleotide
      Sequence; Anti-LAG-3 mAb (BMS-986016)

<400> SEQUENCE: 6

```
gaaattgtgt tgacacagtc tccagccacc ctgtctttgt ctccagggga aagagccacc    60
ctctcctgca gggccagtca gagtattagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctctcac ttttggccag    300
gggaccaacc tggagatcaa a                                              321
```

<210> SEQ ID NO 7
<211> LENGTH: 5
<212> TYPE: PRT
<213> ORGANISM: artificial sequence
<220> FEATURE:
<223> OTHER INFORMATION: Heavy Chain CDR1 Amino Acid Sequence; Anti-LAG-
      3 mAb (BMS-986016)

<400> SEQUENCE: 7

Asp Tyr Tyr Trp Asn
1               5

<210> SEQ ID NO 8
<211> LENGTH: 16
<212> TYPE: PRT

```
<213> ORGANISM: artificial sequence
<220> FEATURE:
<223> OTHER INFORMATION: Heavy Chain CDR2 Amino Acid Sequence; Anti-LAG-
      3 mAb (BMS-986016)

<400> SEQUENCE: 8

Glu Ile Asn His Arg Gly Ser Thr Asn Ser Asn Pro Ser Leu Lys Ser
1               5                   10                  15

<210> SEQ ID NO 9
<211> LENGTH: 12
<212> TYPE: PRT
<213> ORGANISM: artificial sequence
<220> FEATURE:
<223> OTHER INFORMATION: Heavy Chain CDR3 Amino Acid Sequence; Anti-LAG-
      3 mAb (BMS-986016)

<400> SEQUENCE: 9

Gly Tyr Ser Asp Tyr Glu Tyr Asn Trp Phe Asp Pro
1               5                   10

<210> SEQ ID NO 10
<211> LENGTH: 11
<212> TYPE: PRT
<213> ORGANISM: artificial sequence
<220> FEATURE:
<223> OTHER INFORMATION: Light Chain CDR1 Amino Acid Sequence; Anti-LAG-
      3 mAb (BMS-986016)

<400> SEQUENCE: 10

Arg Ala Ser Gln Ser Ile Ser Ser Tyr Leu Ala
1               5                   10

<210> SEQ ID NO 11
<211> LENGTH: 7
<212> TYPE: PRT
<213> ORGANISM: artificial sequence
<220> FEATURE:
<223> OTHER INFORMATION: Light Chain CDR2 Amino Acid Sequence; Anti-LAG-
      3 mAb (BMS-986016)

<400> SEQUENCE: 11

Asp Ala Ser Asn Arg Ala Thr
1               5

<210> SEQ ID NO 12
<211> LENGTH: 9
<212> TYPE: PRT
<213> ORGANISM: artificial sequence
<220> FEATURE:
<223> OTHER INFORMATION: Light Chain CDR3 Amino Acid Sequence; Anti-LAG-
      3 mAb (BMS-986016)

<400> SEQUENCE: 12

Gln Gln Arg Ser Asn Trp Pro Leu Thr
1               5

<210> SEQ ID NO 13
<211> LENGTH: 525
<212> TYPE: PRT
<213> ORGANISM: artificial sequence
<220> FEATURE:
<223> OTHER INFORMATION: Human LAG-3 Amino Acid Sequence

<400> SEQUENCE: 13

Met Trp Glu Ala Gln Phe Leu Gly Leu Leu Phe Leu Gln Pro Leu Trp
1               5                   10                  15
```

```
Val Ala Pro Val Lys Pro Leu Gln Pro Gly Ala Glu Val Pro Val Val
             20                  25                  30
Trp Ala Gln Glu Gly Ala Pro Ala Gln Leu Pro Cys Ser Pro Thr Ile
         35                  40                  45
Pro Leu Gln Asp Leu Ser Leu Leu Arg Arg Ala Gly Val Thr Trp Gln
     50                  55                  60
His Gln Pro Asp Ser Gly Pro Pro Ala Ala Ala Pro Gly His Pro Leu
 65                  70                  75                  80
Ala Pro Gly Pro His Pro Ala Ala Pro Ser Ser Trp Gly Pro Arg Pro
                 85                  90                  95
Arg Arg Tyr Thr Val Leu Ser Val Gly Pro Gly Gly Leu Arg Ser Gly
            100                 105                 110
Arg Leu Pro Leu Gln Pro Arg Val Gln Leu Asp Glu Arg Gly Arg Gln
        115                 120                 125
Arg Gly Asp Phe Ser Leu Trp Leu Arg Pro Ala Arg Arg Ala Asp Ala
    130                 135                 140
Gly Glu Tyr Arg Ala Ala Val His Leu Arg Asp Arg Ala Leu Ser Cys
145                 150                 155                 160
Arg Leu Arg Leu Arg Leu Gly Gln Ala Ser Met Thr Ala Ser Pro Pro
                165                 170                 175
Gly Ser Leu Arg Ala Ser Asp Trp Val Ile Leu Asn Cys Ser Phe Ser
            180                 185                 190
Arg Pro Asp Arg Pro Ala Ser Val His Trp Phe Arg Asn Arg Gly Gln
        195                 200                 205
Gly Arg Val Pro Val Arg Glu Ser Pro His His Leu Ala Glu Ser
    210                 215                 220
Phe Leu Phe Leu Pro Gln Val Ser Pro Met Asp Ser Gly Pro Trp Gly
225                 230                 235                 240
Cys Ile Leu Thr Tyr Arg Asp Gly Phe Asn Val Ser Ile Met Tyr Asn
                245                 250                 255
Leu Thr Val Leu Gly Leu Glu Pro Pro Thr Pro Leu Thr Val Tyr Ala
            260                 265                 270
Gly Ala Gly Ser Arg Val Gly Leu Pro Cys Arg Leu Pro Ala Gly Val
        275                 280                 285
Gly Thr Arg Ser Phe Leu Thr Ala Lys Trp Thr Pro Pro Gly Gly Gly
    290                 295                 300
Pro Asp Leu Leu Val Thr Gly Asp Asn Gly Asp Phe Thr Leu Arg Leu
305                 310                 315                 320
Glu Asp Val Ser Gln Ala Gln Ala Gly Thr Tyr Thr Cys His Ile His
                325                 330                 335
Leu Gln Glu Gln Gln Leu Asn Ala Thr Val Thr Leu Ala Ile Ile Thr
            340                 345                 350
Val Thr Pro Lys Ser Phe Gly Ser Pro Gly Ser Leu Gly Lys Leu Leu
        355                 360                 365
Cys Glu Val Thr Pro Val Ser Gly Gln Glu Arg Phe Val Trp Ser Ser
    370                 375                 380
Leu Asp Thr Pro Ser Gln Arg Ser Phe Ser Gly Pro Trp Leu Glu Ala
385                 390                 395                 400
Gln Glu Ala Gln Leu Leu Ser Gln Pro Trp Gln Cys Gln Leu Tyr Gln
                405                 410                 415
Gly Glu Arg Leu Leu Gly Ala Ala Val Tyr Phe Thr Glu Leu Ser Ser
            420                 425                 430
Pro Gly Ala Gln Arg Ser Gly Arg Ala Pro Gly Ala Leu Pro Ala Gly
```

```
                435                 440                 445
His Leu Leu Leu Phe Leu Thr Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525

<210> SEQ ID NO 14
<211> LENGTH: 8
<212> TYPE: PRT
<213> ORGANISM: artificial sequence
<220> FEATURE:
<223> OTHER INFORMATION: LAG-3 Epitope

<400> SEQUENCE: 14

Pro Gly His Pro Leu Ala Pro Gly
1               5

<210> SEQ ID NO 15
<211> LENGTH: 8
<212> TYPE: PRT
<213> ORGANISM: artificial sequence
<220> FEATURE:
<223> OTHER INFORMATION: LAG-3 Epitope

<400> SEQUENCE: 15

His Pro Ala Ala Pro Ser Ser Trp
1               5

<210> SEQ ID NO 16
<211> LENGTH: 8
<212> TYPE: PRT
<213> ORGANISM: artificial sequence
<220> FEATURE:
<223> OTHER INFORMATION: LAG-3 Epitope

<400> SEQUENCE: 16

Pro Ala Ala Pro Ser Ser Trp Gly
1               5

<210> SEQ ID NO 17
<211> LENGTH: 440
<212> TYPE: PRT
<213> ORGANISM: artificial sequence
<220> FEATURE:
<223> OTHER INFORMATION: Heavy Chain Amino Acid Sequence; Anti-PD-1 mAb
      (BMS936558)

<400> SEQUENCE: 17

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60
```

```
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
             85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 18
<211> LENGTH: 213
<212> TYPE: PRT
<213> ORGANISM: artificial sequence
<220> FEATURE:
<223> OTHER INFORMATION: Light Chain Amino Acid Sequence; Anti-PD-1 mAb
```

(BMS936558)

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 19
<211> LENGTH: 113
<212> TYPE: PRT
<213> ORGANISM: artificial sequence
<220> FEATURE:
<223> OTHER INFORMATION: Heavy Chain Variable Region (VH) Amino Acid
      Sequence; Anti-PD-1 mAb (BMS936558)

<400> SEQUENCE: 19

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 20
<211> LENGTH: 339
<212> TYPE: DNA
<213> ORGANISM: artificial sequence
<220> FEATURE:
<223> OTHER INFORMATION: Heavy Chain Variable Region (VH) Nucleotide
      Sequence; Anti-PD-1 mAb (BMS936558)

<400> SEQUENCE: 20
caggtgcagc tggtggagtc tgggggaggc gtggtccagc ctggggaggtc cctgagactc     60 gactgtaaag cgtctggaat caccttcagt aactctggca tgcactgggt ccgccaggct    120
ccaggcaagg ggctggagtg ggtggcagtt atttggtatg atggaagtaa agatactat     180 gcagactccg tgaagggccg attcaccatc tccagagaca attccaagaa cacgctgttt    240
ctgcaaatga acagcctgag agccgaggac acggctgtgt attactgtgc gacaaacgac    300
gactactggg gccagggaac cctggtcacc gtctcctca                           339

<210> SEQ ID NO 21
<211> LENGTH: 107
<212> TYPE: PRT
<213> ORGANISM: artificial sequence
<220> FEATURE:
<223> OTHER INFORMATION: Light Chain Variable Region (VL) Amino Acid
      Sequence; Anti-PD-1mAb (BMS936558)

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 22
<211> LENGTH: 321
<212> TYPE: DNA
<213> ORGANISM: artificial sequence
<220> FEATURE:
<223> OTHER INFORMATION: Synthetic: Light Chain Variable Region (VL)
      Nucleotide Sequence; Anti-PD-1 mAb (BMS936558)

<400> SEQUENCE: 22
gaaattgtgt tgacacagtc tccagccacc ctgtctttgt ctccagggga aagagccacc     60
ctctcctgca gggccagtca gagtgttagt agttacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag agtagcaact ggcctcggac gttcggccaa    300
gggaccaagg tggaaatcaa a                                              321

<210> SEQ ID NO 23
<211> LENGTH: 5
<212> TYPE: PRT
<213> ORGANISM: artificial sequence
<220> FEATURE:
<223> OTHER INFORMATION: Heavy Chain CDR1 Amino Acid Sequence; Anti-PD-1
      mAb (BMS936558)

<400> SEQUENCE: 23

Asn Ser Gly Met His
1               5

<210> SEQ ID NO 24
<211> LENGTH: 17
<212> TYPE: PRT
<213> ORGANISM: artificial sequence
<220> FEATURE:
<223> OTHER INFORMATION: Heavy Chain CDR2 Amino Acid Sequence; Anti-PD-1
      mAb (BMS936558)

<400> SEQUENCE: 24

Val Ile Trp Tyr Asp Gly Ser Lys Arg Tyr Tyr Ala Asp Ser Val Lys
1               5                   10                  15

Gly

<210> SEQ ID NO 25
<211> LENGTH: 4
<212> TYPE: PRT
<213> ORGANISM: artificial sequence
<220> FEATURE:
<223> OTHER INFORMATION: Heavy Chain CDR3 Amino Acid Sequence; Anti-PD-1
      mAb (BMS936558)

<400> SEQUENCE: 25

Asn Asp Asp Tyr
1

<210> SEQ ID NO 26
<211> LENGTH: 11
<212> TYPE: PRT
<213> ORGANISM: artificial sequence
<220> FEATURE:
<223> OTHER INFORMATION: Light Chain CDR1 Amino Acid Sequence; Anti-PD-1
      mAb (BMS936558)

<400> SEQUENCE: 26

Arg Ala Ser Gln Ser Val Ser Ser Tyr Leu Ala
1               5                   10

<210> SEQ ID NO 27
<211> LENGTH: 7
<212> TYPE: PRT
<213> ORGANISM: artificial sequence
<220> FEATURE:
<223> OTHER INFORMATION: Light Chain CDR2 Amino Acid Sequence; Anti-PD-1
      mAb (BMS936558)

<400> SEQUENCE: 27

Asp Ala Ser Asn Arg Ala Thr
1               5

<210> SEQ ID NO 28
<211> LENGTH: 9
<212> TYPE: PRT
<213> ORGANISM: artificial sequence
<220> FEATURE:
<223> OTHER INFORMATION: Light Chain CDR3 Amino Acid Sequence; Anti-PD-1 mAb (BMS936558)

<400> SEQUENCE: 28

Gln Gln Ser Ser Asn Trp Pro Arg Thr
1               5

<210> SEQ ID NO 29
<211> LENGTH: 2106
<212> TYPE: DNA
<213> ORGANISM: artificial sequence
<220> FEATURE:
<223> OTHER INFORMATION: Complete PD-1 sequence

<400> SEQUENCE: 29

| | | | | | |
|---|---|---|---|---|---|
| agtttccctt | ccgctcacct | ccgcctgagc | agtggagaag | gcggcactct | ggtggggctg | 60 |
| ctccaggcat | gcagatccca | caggcgccct | ggccagtcgt | ctgggcggtg | ctacaactgg | 120 |
| gctggcggcc | aggatggttc | ttagactccc | cagacaggcc | ctggaacccc | ccaccttct | 180 |
| tcccagccct | gctcgtggtg | accgaagggg | acaacgccac | cttcacctgc | agcttctcca | 240 |
| acacatcgga | gagcttcgtg | ctaaactggt | accgcatgag | ccccagcaac | cagacggaca | 300 |
| agctggccgc | cttccccgag | gaccgcagcc | agcccggcca | ggactgccgc | ttccgtgtca | 360 |
| cacaactgcc | caacgggcgt | gacttccaca | tgagcgtggt | cagggcccgg | cgcaatgaca | 420 |
| gcggcaccta | cctctgtggg | gccatctccc | tggcccccaa | ggcgcagatc | aaagagagcc | 480 |
| tgcgggcaga | gctcagggtg | acagagagaa | gggcagaagt | gcccacagcc | caccccagcc | 540 |
| cctcacccag | gccagccggc | cagttccaaa | ccctggtggt | tggtgtcgtg | gcggcctgc | 600 |
| tgggcagcct | ggtgctgcta | gtctgggtcc | tggccgtcat | ctgctcccgg | gccgcacgag | 660 |
| ggacaatagg | agccaggcgc | accggccagc | cctgaagga | ggacccctca | gccgtgcctg | 720 |
| tgttctctgt | ggactatggg | gagctggatt | tccagtggcg | agagaagacc | ccggagcccc | 780 |
| ccgtgccctg | tgtccctgag | cagacggagt | atgccaccat | tgtctttcct | agcggaatgg | 840 |
| gcacctcatc | ccccgcccgc | aggggctcag | ccgacggccc | tcggagtgcc | cagccactga | 900 |
| ggcctgagga | tggacactgc | tcttggcccc | tctgaccggc | ttccttggcc | accagtgttc | 960 |
| tgcagaccct | ccaccatgag | cccgggtcag | cgcatttcct | caggagaagc | aggcagggtg | 1020 |
| caggccattg | caggccgtcc | aggggctgag | ctgcctgggg | gcgaccgggg | ctccagcctg | 1080 |
| cacctgcacc | aggcacagcc | ccaccacagg | actcatgtct | caatgccac | agtgagccca | 1140 |
| ggcagcaggt | gtcaccgtcc | cctacaggga | gggccagatg | cagtcactgc | ttcaggtcct | 1200 |
| gccagcacag | agctgcctgc | gtccagctcc | ctgaatctct | gctgctgctg | ctgctgctgc | 1260 |
| tgctgctgcc | tgcggcccgg | ggctgaaggc | gccgtggccc | tgcctgacgc | cccggagcct | 1320 |
| cctgcctgaa | cttgggggct | ggttggagat | ggccttggag | cagccaaggt | gcccctggca | 1380 |
| gtggcatccc | gaaacgccct | ggacgcaggg | cccaagactg | gcacaggag | tgggaggtac | 1440 |
| atggggctgg | ggactcccca | ggagttatct | gctccctgca | ggcctagaga | agtttcaggg | 1500 |
| aaggtcagaa | gagctcctgg | ctgtggtggg | cagggcagga | aacccctccc | acctttacac | 1560 |
| atgcccaggc | agcacctcag | gccctttgtg | gggcagggaa | gctgaggcag | taagcgggca | 1620 |
| ggcagagctg | gaggcctttc | aggccagcca | gcactctggc | ctcctgccgc | cgcattccac | 1680 |
| cccagcccct | cacaccactc | gggagaggga | catcctacgg | tcccaaggtc | aggagggcag | 1740 |
| ggctggggtt | gactcaggcc | cctcccagct | gtggccacct | gggtgttggg | agggcagaag | 1800 |
| tgcaggcacc | tagggccccc | catgtgccca | ccctgggagc | tctccttgga | acccattcct | 1860 |

```
gaaattattt aaaggggttg gccgggctcc caccagggcc tgggtgggaa ggtacaggcg    1920
ttccccgggg gcctagtacc cccgcgtggc ctatccactc ctcacatcca cacactgcac    1980
ccccactcct ggggcagggc caccagcatc caggcggcca gcaggcacct gagtggctgg    2040
gacaagggat cccccttccc tgtggttcta ttatattata attataatta aatatgagag    2100
catgct                                                               2106
```

<210> SEQ ID NO 30
<211> LENGTH: 1344
<212> TYPE: DNA
<213> ORGANISM: artificial sequence
<220> FEATURE:
<223> OTHER INFORMATION: Heavy Chain Nucleotide Sequence; Anti-LAG-3 mAb
      (BMS-986016)

<400> SEQUENCE: 30

```
caggtgcagc tacagcagtg gggcgcagga ctgttgaagc cttcggagac cctgtccctc     60
acctgcgctg tctatggtgg gtccttcagt gattactact ggaactggat ccgccagccc    120
ccagggaagg ggctggagtg gattgggaa atcaatcatc gtggaagcac caactccaac     180
ccgtccctca agagtcgagt caccctatca ctagacacgt ccaagaacca gttctccctg    240
aagctgaggt ctgtgaccgc cgcggacacg gctgtgtatt actgtgcgtt tggatatagt    300
gactacgagt acaactggtt cgaccccgg ggccagggaa ccctggtcac cgtctcctca     360
gctagcacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc ccccatgccc accatgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctccctgt ctctgggtaa atga                                           1344
```

<210> SEQ ID NO 31
<211> LENGTH: 645
<212> TYPE: DNA
<213> ORGANISM: artificial sequence
<220> FEATURE:
<223> OTHER INFORMATION: Light Chain Nucleotide Sequence; Anti-LAG-3 mAb
      (BMS-986016)

<400> SEQUENCE: 31

```
gaaattgtgt tgacacagtc tccagccacc ctgtctttgt ctccagggga aagagccacc     60
```

```
ctctcctgca gggccagtca gagtattagc agctacttag cctggtacca acagaaacct        120
ggccaggctc ccaggctcct catctatgat gcatccaaca gggccactgg catcccagcc        180
aggttcagtg gcagtgggtc tgggacagac ttcactctca ccatcagcag cctagagcct        240
gaagattttg cagtttatta ctgtcagcag cgtagcaact ggcctctcac ttttggccag        300
gggaccaacc tggagatcaa acgtacggtg gctgcaccat ctgtcttcat cttcccgcca        360
tctgatgagc agttgaaatc tggaactgcc tctgttgtgt gcctgctgaa taacttctat        420
cccagagagg ccaaagtaca gtggaaggtg gataacgccc tccaatcggg taactcccag        480
gagagtgtca cagagcagga cagcaaggac agcacctaca gcctcagcag cacccctgacg       540 ctgagcaaag cagactacga gaaacacaaa gtctacgcct gcgaagtcac ccatcagggc        600
ctgagctcgc ccgtcacaaa gagcttcaac aggggagagt gttag                        645
```

<210> SEQ ID NO 32
<211> LENGTH: 6
<212> TYPE: PRT
<213> ORGANISM: artificial sequence
<220> FEATURE:
<223> OTHER INFORMATION: Motif

<400> SEQUENCE: 32

Met Tyr Pro Pro Pro Tyr
1               5

COMPOSITIONS COMPRISING AN ANTI-LAG-3 ANTIBODY OR AN ANTI-LAG-3 ANTIBODY AND AN ANTI-PD-1 OR ANTI-PD-L1 ANTIBODY

CROSS-REFERENCE TO RELATED APPLICATIONS

This application claims priority to U.S. Provisional Application Nos. 62/512,644, filed May 30, 2017 and 62/513,816, filed Jun. 1, 2017 which are incorporated herein by reference in their entireties.

REFERENCE TO SEQUENCE LISTING SUBMITTED ELECTRONICALLY

The content of the electronically submitted sequence listing (Name 3338_0710002_Seqlisting_ST25; Size: 33,616 bytes; and Date of Creation: Nov. 21, 2019) is incorporated herein by reference in its entirety.

FIELD OF THE INVENTION

This invention relates to pharmaceutical compositions that comprise (i) an anti-LAG-3 antibody or antigen binding fragment thereof, or (ii) an anti-LAG-3 antibody or antigen binding fragment thereof and an anti-PD-1 antibody, anti-PD-L1 antibody, or antigen binding fragments thereof. The invention also relates to pharmaceutical compositions that comprise a buffering agent, a stabilizing or bulking agent, and a surfactant.

BACKGROUND OF THE INVENTION

Lymphocyte activation gene-3 (LAG-3, LAG3, or CD223) is a type I transmembrane protein that is expressed on the cell surface of activated CD4+ and CD8+ T cells and subsets of NK and dendritic cells (Triebel F., et al., *J. Exp. Med.* 1990; 171:1393-1405; Workman C. J., et al., *J. Immunol.* 2009; 182(4):1885-91). LAG-3 is closely related to CD4, which is a co-receptor for T helper cell activation. Both molecules have four extracellular Ig-like domains and require binding to their ligand, major histocompatibility complex (MHC) class II, for their functional activity. In contrast to CD4, LAG-3 is only expressed on the cell surface of activated T cells and its cleavage from the cell surface terminates LAG-3 signaling. LAG-3 is also found as a soluble protein but it does not bind to MHC class II and its function is unknown.

It has been reported that LAG-3 plays an important role in promoting regulatory T cell (Treg) activity and in negatively regulating T cell activation and proliferation (Workman C. J., et al., *J. Immunol.* 2005; 174:688-695). Both natural and induced Treg express increased LAG-3, which is required for their maximal suppressive function (Camisaschi C., et al., *J. Immunol.* 2010; 184:6545-6551 and Huang C. T., et al., *Immunity.* 2004; 21:503-513). Furthermore, ectopic expression of LAG-3 on CD4+ effector T cells reduced their proliferative capacity and conferred on them regulatory potential against third party T cells (Huang C. T., et al., *Immunity.* 2004; 21:503-513). Recent studies have also shown that high LAG-3 expression on exhausted lymphocytic choriomeningitis virus (LCMV)-specific CD8+ T cells contributes to their unresponsive state and limits CD8+ T cell antitumor responses (Blackburn S. D., et al., *Nat. Immunol.* 2009; 10:29-37 and Grosso J. F., et al., *J. Clin. Invest.* 2007; 117:3383-3392). In fact, LAG-3 maintained tolerance to self and tumor antigens via direct effects on CD8+ T cells in 2 murine models (Grosso J. F., et al., *J. Clin. Invest.* 2007; 117:3383-3392).

Programmed Cell Death 1 (PD-1) is a cell surface signaling receptor that plays a critical role in the regulation of T cell activation and tolerance (Keir M. E., et al., *Annu. Rev. Immunol.* 2008; 26:677-704). It is a type I transmembrane protein and together with BTLA, CTLA-4, ICOS and CD28, comprise the CD28 family of T cell co-stimulatory receptors. PD-1 is primarily expressed on activated T cells, B cells, and myeloid cells (Dong H., et al., *Nat. Med.* 1999; 5:1365-1369). It is also expressed on natural killer (NK) cells (Terme M., et al., *Cancer Res.* 2011; 71:5393-5399). Binding of PD-1 by its ligands, PD-L1 and PD-L2, results in phosphorylation of the tyrosine residue in the proximal intracellular immune receptor tyrosine inhibitory domain, followed by recruitment of the phosphatase SHP-2, eventually resulting in down-regulation of T cell activation. One important role of PD-1 is to limit the activity of T cells in peripheral tissues at the time of an inflammatory response to infection, thus limiting the development of autoimmunity (Pardoll D. M., *Nat. Rev. Cancer* 2012; 12:252-264). Evidence of this negative regulatory role comes from the finding that PD-1-deficient mice develop lupus-like autoimmune diseases including arthritis and nephritis, along with cardiomyopathy (Nishimura H., et al., *Immunity,* 1999; 11:141-151; and Nishimura H., et al., *Science,* 2001; 291: 319-322). In the tumor setting, the consequence is the development of immune resistance within the tumor microenvironment. PD-1 is highly expressed on tumor-infiltrating lymphocytes, and its ligands are up-regulated on the cell surface of many different tumors (Dong H., et al., *Nat. Med.* 2002; 8:793-800). Multiple murine cancer models have demonstrated that binding of ligand to PD-1 results in immune evasion. In addition, blockade of this interaction results in anti-tumor activity (Topalian S. L., et al. *NEJM* 2012; 366(26):2443-2454; Hamid O., et al., *NEJM* 2013; 369:134-144). Moreover, it has been shown that inhibition of the PD-1/PD-L1 interaction mediates potent antitumor activity in preclinical models (U.S. Pat. Nos. 8,008,449 and 7,943,743).

Patients with metastatic or refractory solid tumors have very poor prognosis (Rosenberg S. A., et al., Cancer immunotherapy in Cancer: Principles & Practice of Oncology (Eds DeVita V. T., Lawrence T. S. and Rosenberg S. A.) 2011; 332-344 (Lippincott Williams & Wilkins, Philadelphia Pa.)). Despite advances in multimodal therapy, increases in overall survival in this patient population have been limited. Accordingly, it is an object of the present invention to provide improved methods for treating subjects with such tumors (e.g., advanced refractory solid tumors).

SUMMARY OF THE INVENTION

The present invention relates to pharmaceutical compositions that comprise (i) an anti-LAG-3 antibody or antigen binding fragment thereof, or (ii) an anti-LAG-3 antibody or antigen binding fragment thereof and an anti-PD-1 antibody, or anti-PD-L1 antibody, or antigen binding fragments thereof. In some embodiments, the pharmaceutical composition comprises (i) from about 1 mg/ml to about 300 mg/ml of an anti-LAG-3 antibody or antigen binding fragment thereof; (ii) from about 5 mM to about 50 mM of a buffering agent; (iii) from about 50 mM to about 300 mM of a stabilizing agent or bulking agent; and (iv) from about 0.001% to about 1% (w/v) of a surfactant. In some embodiments, the pharmaceutical composition further comprises (v) a chelating agent. In some embodiments, the pharmaceutical composition comprises from about 80 mg to about 240 mg of the anti-LAG-3 antibody or antigen binding fragment thereof. In some embodiments, the pharmaceutical composition comprises about 80 mg, about 120 mg, about 160 mg, or about 240 mg of the anti-LAG-3 antibody or antigen binding fragment thereof. In some embodiments, the pharmaceutical composition comprises from about 4 mg/ml to about 12 mg/ml of the anti-LAG-3 antibody or antigen binding fragment thereof. In other embodiments, the pharmaceutical composition comprises from about 4 mg/ml, about 8 mg/ml, about 10 mg/ml, or about 12 mg/ml of the anti-LAG-3 antibody or antigen binding fragment thereof.

In other embodiments, the anti-LAG-3 antibody or antigen binding fragment thereof of such compositions comprises CDR1, CDR2, and CDR3 domains of the heavy chain variable region having the sequence set forth in SEQ ID NO:3, and/or CDR1, CDR2, and CDR3 domains of the light chain variable region having the sequence set forth in SEQ ID NO:5. In some embodiments, the anti-LAG-3 antibody or antigen binding fragment thereof of such compositions comprises a CDR1, CDR2, and CDR3 domains of the heavy chain variable region at least 90% identical to the sequence set forth in SEQ ID NO:3, and/or CDR1, CDR2, and CDR3 domains of the light chain variable region at least 90% identical to the sequence set forth in SEQ ID NO:5. In other embodiments, the anti-LAG-3 antibody or antigen binding fragment thereof comprises (a) a heavy chain variable region CDR1 comprising the sequence set forth in SEQ ID NO:7; (b) a heavy chain variable region CDR2 comprising the sequence set forth in SEQ ID NO:8; (c) a heavy chain variable region CDR3 comprising the sequence set forth in SEQ ID NO:9; (d) a light chain variable region CDR1 comprising the sequence set forth in SEQ ID NO:10; (e) a light chain variable region CDR2 comprising the sequence set forth in SEQ ID NO:11; and/or (f) a light chain variable region CDR3 comprising the sequence set forth in SEQ ID NO:12. In other embodiments, the anti-LAG-3 antibody or antigen binding fragment thereof comprises heavy and/or light chain variable regions comprising the sequences set forth in SEQ ID NOs:3 and 5, respectively. In other embodiments, the anti-LAG-3 antibody or antigen binding fragment thereof comprises heavy and/or light chains comprising the sequences set forth in SEQ ID NOs:1 and 2, respectively. In other embodiments, the anti-LAG-3 antibody is BMS-986016, IMP731 (H5L7BW), MK-4280 (28G-10), REGN3767, GSK2831781, humanized BAP050, IMP-701 (LAG-5250), or FS-118.

In other embodiments, the buffering agent of such pharmaceutical compositions is histidine, Tris-Cl, citrate, Tris-citrate, phosphate (e.g., sodium phosphate), or any combination thereof. In some embodiments, the pharmaceutical composition comprises about 10 mM or about 20 mM of the buffering agent. In other embodiments, the stabilizing agent of such pharmaceutical compositions is sucrose, trehalose, raffinose, arginine, or any combination thereof. In some embodiments, the bulking agent of such pharmaceutical compositions is sodium chloride, mannitol, glycine, alanine, or any combination thereof. In other embodiments, the pharmaceutical composition comprises about 150 mM or about 250 mM of the stabilizing agent or bulking agent. In some embodiments, the surfactant is polysorbate, poloxamer, or any combination thereof (e.g., polysorbate 80 (PS80), polysorbate 20 (PS20), poloxamer 188 (PX188), or any combination thereof). In other embodiments, the pharmaceutical composition comprises from about 0.05% to about 1% (w/v) of the surfactant.

In other embodiments, such pharmaceutical compositions further comprise (v) from about 5 µM to about 1 mM of a chelating agent. In some embodiments, the chelating agent is diethylenetriaminepentaacetic acid (DTPA), ethylenediaminetetraacetic acid (EDTA), nitrilotriacetic acid, or any combination thereof. In some embodiments, the pharmaceutical composition comprises about 20 µM of the chelating agent.

In another aspect, the invention is directed to a pharmaceutical composition comprising (i) from about 1 mg/ml to about 100 mg/ml of an anti-LAG-3 antibody or antigen binding fragment thereof; (ii) from about 5 mM to about 50 mM of citrate; (iii) from about 50 mM to about 300 mM of sodium chloride; and (iv) from about 0.001% to about 1% (w/v) of polysorbate or poloxamer. In another aspect, the pharmaceutical composition comprises (i) about 11 mg/ml of an anti-LAG-3 antibody or antigen binding fragment thereof; (ii) about 10 mM of citrate and about 10 mM phosphate; (iii) about 150 mM of sodium chloride; and (iv) about 0.05% (w/v) of polysorbate 80. In another aspect, the pharmaceutical composition comprises (i) about 11 mg/ml of an anti-LAG-3 antibody or antigen binding fragment thereof; (ii) about 10 mM of sodium citrate and about 10 mM sodium phosphate; (iii) about 150 mM of sodium chloride; and (iv) about 0.05% (w/v) of polysorbate 80. In another aspect, the pharmaceutical composition comprises (i) from about 1 mg/ml to about 100 mg/ml of an anti-LAG-3 antibody or antigen binding fragment thereof; (ii) from about 5 mM to about 50 mM of histidine; (iii) from about 50 mM to about 300 mM of sucrose; and (iv) from about 0.001% to about 1% (w/v) of polysorbate or poloxamer. In another aspect, the invention comprises a pharmaceutical composition comprising (i) about 10 mg/ml of an anti-LAG-3 antibody or antigen binding fragment thereof; (ii) about 20 mM of histidine; (iii) about 250 mM of sucrose; and (iv) about 0.05% (w/v) of polysorbate 80. In another aspect, the pharmaceutical composition comprises (i) from about 1 mg/ml to about 100 mg/ml of an anti-LAG-3 antibody or antigen binding fragment thereof; (ii) from about 5 mM to about 50 mM of histidine; (iii) from about 50 mM to about 300 mM of sucrose; (iv) from about 5 µM to about 1 mM of one or more chelating agents; and (v) from about 0.001% to about 1% (w/v) of polysorbate or poloxamer.

In yet another aspect, the invention is directed to a pharmaceutical composition comprising (i) about 10 mg/ml of an anti-LAG-3 antibody or antigen binding fragment thereof; (ii) about 20 mM of histidine; (iii) about 250 mM of sucrose; (iv) about 20 µM to about 50 µM of DTPA or EDTA; and (v) about 0.05% (w/v) of polysorbate 80. In another aspect, the pharmaceutical composition comprises (i) 11 mg/ml of an anti-LAG-3 antibody or antigen binding fragment thereof; (ii) 10 mM of citrate and 10 mM phosphate; (iii) 150 mM of sodium chloride; and (iv) 0.05% (w/v) of polysorbate 80. In another aspect, the pharmaceutical composition comprises (i) 11 mg/ml of an anti-LAG-3 antibody or antigen binding fragment thereof (ii) 10 mM of sodium citrate and 10 mM sodium phosphate; (iii) 150 mM of sodium chloride; and (iv) 0.05% (w/v) of polysorbate 80. In another aspect, the pharmaceutical composition comprises (i) 110 mg of an anti-LAG-3 antibody or antigen binding fragment thereof; (ii) 10 mM of citrate; (iii) 150 mM of sodium chloride; and (iv) 0.05% (w/v) of polysorbate 80. In another aspect, the pharmaceutical composition comprises (i) 10 mg/ml of an anti-LAG-3 antibody or antigen binding fragment thereof; (ii) 20 mM of histidine; (iii) 250 mM of sucrose; and (iv) 0.05% (w/v) of polysorbate 80. In another aspect, the pharmaceutical composition comprises (i) 100 mg of an anti-LAG-3 antibody or antigen binding fragment thereof; (ii) 20 mM of histidine; (iii) 250 mM of sucrose; and (iv) 0.05% (w/v) of polysorbate 80. In another aspect, the pharmaceutical composition comprises (i) 80 mg of an anti-LAG-3 antibody or antigen binding fragment thereof; (ii) 20 mM of histidine; (iii) 250 mM of sucrose; and (iv) 0.05% (w/v) of polysorbate 80. In another aspect, the pharmaceutical composition comprises (i) 10 mg/ml of an anti-LAG-3 antibody or antigen binding fragment thereof (ii) 20 mM of histidine; (iii) 250 mM of sucrose; (iv) from 20 µM to 50 µM of DTPA or EDTA; and (v) 0.05% (w/v) of polysorbate 80. In another aspect, the pharmaceutical composition comprises (i) 100 mg of an anti-LAG-3 antibody or antigen binding fragment thereof (ii) 20 mM of histidine; (iii) 250 mM of sucrose; (iv) from 20 µM to 50 µM of DTPA or EDTA; and (v) 0.05% (w/v) of polysorbate 80. In another aspect, the pharmaceutical composition comprises (i) 80 mg of an anti-LAG-3 antibody or antigen binding fragment thereof (ii) 20 mM of histidine; (iii) 250 mM of sucrose; (iv) from 20 µM to 50 µM of DTPA or EDTA; and (v) 0.05% (w/v) of polysorbate 80.

In some embodiments, such pharmaceutical compositions can have a pH of from about 5 to about 6. In one embodiment, the pH is about 5.5 or about 5.6.

In another aspect, the invention is directed to a pharmaceutical composition comprising (i) from about 1 mg/ml to about 100 mg/ml of an anti-LAG-3 antibody or antigen binding fragment thereof; (ii) from about 1 mg/ml to about 100 mg/ml of an anti-PD-1 antibody, or anti-PD-L1 antibody, or antigen binding fragments thereof; (iii) from about 5 mM to about 50 mM of a buffering agent; (iv) from about 50 mM to about 300 mM of a stabilizing agent; (v) from about 5 µM to about 1 mM of a chelating agent; and (vi) from about 0.001% to about 1% (w/v) of a surfactant. In some embodiments, the pharmaceutical composition comprises from about 4 mg/ml to about 12 mg/ml, or from about 80 mg to about 240 mg of the anti-LAG-3 antibody or antigen binding fragment thereof. In other embodiments, the pharmaceutical composition comprises about 4 mg/ml, about 8 mg/ml, about 10 mg/ml, about 12 mg/ml, about 80 mg, about 120 mg, about 160 mg, or about 240 mg of the anti-LAG-3 antibody or antigen binding fragment thereof.

In one aspect of such compositions, the anti-LAG-3 antibody or antigen binding fragment thereof comprises CDR1, CDR2, and CDR3 domains of the heavy chain variable region having the sequence set forth in SEQ ID NO:3, and/or CDR1, CDR2, and CDR3 domains of the light chain variable region having the sequence set forth in SEQ ID NO:5. In another aspect, the anti-LAG-3 antibody or antigen binding fragment thereof comprises (a) a heavy chain variable region CDR1 comprising the sequence set forth in SEQ ID NO:7; (b) a heavy chain variable region CDR2 comprising the sequence set forth in SEQ ID NO:8; (c) a heavy chain variable region CDR3 comprising the sequence set forth in SEQ ID NO:9; (d) a light chain variable region CDR1 comprising the sequence set forth in SEQ ID NO:10; (e) a light chain variable region CDR2 comprising the sequence set forth in SEQ ID NO:11; and/or (f) a light chain variable region CDR3 comprising the sequence set forth in SEQ ID NO:12. In another aspect of such compositions, the anti-LAG-3 antibody is BMS-986016, IMP731 (H5L7BW), MK-4280 (28G-10), REGN3767, GSK2831781, humanized BAP050, IMP-701 (LAG-5250), FS-118. In another aspect of such compositions, the anti-LAG-3 antibody or antigen binding fragment thereof comprises heavy and/or light chain variable regions comprising the sequences set forth in SEQ ID NOs:3 and 5, respectively. In another aspect of such compositions, the anti-LAG-3 antibody or antigen binding fragment thereof comprises heavy and/or light chains comprising the sequences set forth in SEQ ID NOs:1 and 2, respectively.

In another aspect, such compositions comprise from about 60 mg to about 300 mg of the anti-PD-1 antibody, or anti-PD-L1 antibody, or antigen binding fragments thereof. In some embodiments, the anti-PD-1 antibody, anti-PD-L1 antibody, or antigen binding fragments thereof comprises CDR1, CDR2, and CDR3 domains of the heavy chain variable region having the sequence set forth in SEQ ID NO:19, and/or CDR1, CDR2, and CDR3 domains of the light chain variable region having the sequence set forth in SEQ ID NO:21. In some embodiments, the anti-PD-1 antibody, or anti-PD-L1 antibody, or antigen binding fragments thereof comprises (a) a heavy chain variable region CDR1 comprising the sequence set forth in SEQ ID NO:23; (b) a heavy chain variable region CDR2 comprising the sequence set forth in SEQ ID NO:24; (c) a heavy chain variable region CDR3 comprising the sequence set forth in SEQ ID NO:25; (d) a light chain variable region CDR1 comprising the sequence set forth in SEQ ID NO:26; (e) a light chain variable region CDR2 comprising the sequence set forth in SEQ ID NO:27; and/or (f) a light chain variable region CDR3 comprising the sequence set forth in SEQ ID NO:28. In other embodiments, the anti-PD-1 antibody, or anti-PD-L1 antibody, or antigen binding fragments thereof comprises heavy and/or light chain variable regions comprising the sequences set forth in SEQ ID NOs:19 and 21, respectively. In other embodiments, the anti-PD-1 antibody, or anti-PD-L1 antibody, or antigen binding fragments thereof comprises heavy and/or light chains comprising the sequences as set forth in SEQ ID NOs:17 and 18, respectively. In other embodiments, the anti-PD-1 antibody thereof is pembrolizumab (KEYTRUDA; MK-3475), pidilizumab (CT-011), or nivolumab (OPDIVO; BMS-936558). In other embodiments, the anti-PD-L1 antibody is atezolizumab (TECENTRIQ; RG7446), durvalumab (IMFINZI; MEDI4736), or BMS-936559. In other embodiments, the anti-LAG-3 antibody is BMS-986016 and the anti-PD-1 antibody is nivolumab, the anti-LAG-3 antibody is MK-4280 and the anti-PD-1 antibody is pembrolizumab, the anti-LAG-3 antibody is REGN3767 and the anti-PD-1 antibody is REGN2810, the anti-LAG-3 antibody is LAG525 and the anti-PD-1 is REGN2810, or the anti-LAG-3 antibody is LAG525 and the anti-PD-1 antibody is PDR001.

In other aspects of such compositions, the ratio of the amount of the anti-LAG-3 antibody or antigen binding fragment thereof, to the anti-PD-1 antibody, anti-PD-L1 antibody, or antigen binding fragments thereof is about 1:3, about 1:1, about 2:3, or about 1:1. In some embodiments, such compositions can comprise about 240 mg of the anti-PD-1 antibody, or anti-PD-L1 antibody, or antigen binding fragments thereof and about 80 mg of the anti-LAG-3 antibody or antigen binding fragment thereof. In some embodiments, such compositions can comprise about 240 mg of the anti-PD-1 antibody, or anti-PD-L1 antibody, or antigen binding fragments thereof and about 160 mg of the anti-LAG-3 antibody or antigen binding fragment thereof. In other embodiments, such compositions can comprise about 240 mg of the anti-PD-1 antibody, or anti-PD-L1 antibody, or antigen binding fragments thereof and about 240 mg of the anti-LAG-3 antibody or antigen binding fragment thereof. In other embodiments, the compositions can comprise about 12 mg/ml of the anti-PD-1 antibody, or anti-PD-L1 antibody, or antigen binding fragments thereof and about 4 mg/ml of the anti-LAG-3 antibody or antigen binding fragment thereof. In other embodiments, such compositions can comprise about 12 mg/ml of the anti-PD-1 antibody, or anti-PD-L1 antibody, or antigen binding fragments thereof and about 8 mg/ml of the anti-LAG-3 antibody or antigen binding fragment thereof. In other embodiments, such compositions can comprise about 12 mg/ml of the anti-PD-1 antibody, or anti-PD-L1 antibody, or antigen binding fragments thereof and about 12 mg/ml of the anti-LAG-3 antibody or antigen binding fragment thereof.

In another aspect, the invention is directed to a pharmaceutical composition comprising (i) from about 5 mM to about 50 mM of a buffering agent; (ii) from about 50 mM to about 300 mM of a stabilizing agent or bulking agent; and (iii) from about 0.001% to about 1% (w/v) of a surfactant. In another aspect, the invention is directed to a pharmaceutical composition comprising (i) from about 5 mM to about 50 mM of a buffering agent; (ii) from about 50 mM to about 300 mM of a stabilizing agent; (iii) from about 5 μM to about 1 mM of a chelating agent; and (iv) from about 0.001% to about 1% (w/v) of a surfactant. In some embodiments, such compositions are used in antibody formulation.

In certain aspects of the invention, the compositions of the invention comprise a buffering agent. In some embodiments, the buffering agent is histidine, Tris-Cl, citrate, Tris-citrate, phosphate (e.g., sodium phosphate), or any combination thereof. In other embodiments, the composition comprises about 20 mM of the buffering agent. In other aspects, the compositions comprise a stabilizing agent. In some embodiments, the stabilizing agent is sucrose, trehalose, raffinose, arginine, sodium chloride, or any combination thereof. In some embodiments, the composition comprises about 250 mM of the stabilizing agent. In other aspects, the composition comprises a chelating agent. In some embodiments, the chelating agent is DTPA, EDTA, nitrilotriacetic acid, or any combination thereof. In some embodiments, the composition comprises from about 20 μM to about 50 μM of the chelating agent. In other aspects, the composition comprises a surfactant. In some embodiments, the surfactant is polysorbate, poloxamer, or any combination thereof (e.g., PS80, PS20, PX188, or any combination thereof. In other embodiments, the composition comprises from about 0.05% to about 1% (w/v) of the surfactant.

Still other aspects of the invention are directed to a pharmaceutical composition comprising (i) from about 1 mg/ml to about 100 mg/ml of an anti-LAG-3 antibody or antigen binding fragment thereof; (ii) from about 1 mg/ml to about 100 mg/ml of an anti-PD-1 antibody, or anti-PD-L1 antibody, or antigen binding fragments thereof; (iii) from about 5 mM to about 50 mM of histidine; (iv) from about 50 mM to about 300 mM of sucrose; (v) from about 5 μM to about 1 mM of DTPA or EDTA; and (vi) from about 0.001% to about 1% (w/v) of polysorbate or poloxamer. In other embodiments, the pharmaceutical composition comprises (i) from about 80 mg to about 240 mg of an anti-LAG-3 antibody or antigen binding fragment thereof; (ii) from about 60 mg to about 300 mg of an anti-PD-1 antibody, or anti-PD-L1 antibody, or antigen binding fragments thereof; (iii) from about 5 mM to about 50 mM of histidine; (iv) from about 50 mM to about 300 mM of sucrose; (v) from about 5 μM to about 1 mM of DTPA or EDTA; and (vi) from about 0.001% to about 1% (w/v) of polysorbate or poloxamer. In other embodiments, the pharmaceutical composition comprises (i) about 4 mg/ml, about 8 mg/ml, about 10 mg/ml, or about 12 mg/ml of an anti-LAG-3 antibody or antigen binding fragment thereof; (ii) about 12 mg/ml of an anti-PD-1 antibody, or anti-PD-L1 antibody, or antigen binding fragments thereof; (iii) about 20 mM of histidine; (iv) about 250 mM of sucrose; (v) from about 20 μM to about 50 μM of DTPA or EDTA; and (vi) about 0.05% (w/v) of polysorbate 80.

In still other aspects, the pharmaceutical composition comprises (i) about 80 mg, about 160 mg, about 200 mg or about 240 mg of an anti-LAG-3 antibody or antigen binding fragment thereof; (ii) about 240 mg of an anti-PD-1 antibody, or anti-PD-L1 antibody, or antigen binding fragments thereof; (iii) about 20 mM of histidine; (iv) about 250 mM of sucrose; (v) from about 20 μM to about 50 μM of DTPA or EDTA; and (vi) about 0.05% (w/v) of polysorbate 80. In other embodiments, the pharmaceutical composition comprises (i) 4 mg/ml, 8 mg/ml, 10 mg/ml, or 12 mg/ml of an anti-LAG-3 antibody or antigen binding fragment thereof; (ii) 12 mg/ml of an anti-PD-1 antibody, or anti-PD-L1 antibody, or antigen binding fragments thereof; (iii) 20 mM of histidine; (iv) 250 mM of sucrose; (v) from 20 μM to 50 μM of DTPA or EDTA; and (vi) 0.05% (w/v) of polysorbate 80. In other embodiments, the pharmaceutical composition comprises (i) 80 mg, 160 mg, 200 mg, or 240 mg of an anti-LAG-3 antibody, or antigen binding fragment thereof; (ii) 240 mg of an anti-PD-1 antibody, or anti-PD-L1 antibody, or antigen binding fragments thereof; (iii) 20 mM of histidine; (iv) 250 mM of sucrose; (v) from 20 μM to 50 μM of DTPA or EDTA; and (vi) 0.05% (w/v) of polysorbate 80.

In some embodiments of such compositions, the pH of the composition is from about 5 to about 6.5. In other embodiments, the pH is about 5.3 to about 6.3. In other embodiments, the pH is 5.8. In still other embodiments, the pH is determined using a pH meter.

In other aspects, the pharmaceutical compositions of the invention are for intravenous administration. In other aspects, the pharmaceutical compositions of the invention are diluted prior to use. In some embodiments, the compositions are diluted with 0.9% Sodium Chloride Injection, USP or 5% Dextrose Injection, USP prior to use. In other embodiments, the composition is diluted to obtain a desired antibody concentration.

Other aspects of the invention are directed to a vial, syringe, intravenous bag, or kit comprising a pharmaceutical composition of the invention. In some embodiments, the vial further comprises a stopper and a seal. In some embodiments, the total volume in the vial is 8 mls or 10 mls.

In yet other aspects of the invention, the pharmaceutical composition further comprises a third therapeutic agent. In some embodiments, the third therapeutic agent is an antibody or immune-oncology agent.

In other aspects of the invention, the composition is stable at about −60° C., about 5° C., about 25° C., and/or about 40° C. for at least about 1 month, at least about 2 months, at least about 3 months, at least about 6 months, at least about 9 months, at least about 1 year, at least about 2 years, at least about 3 years, at least about 4 years, or at least about 5 years. In other aspects, the pharmaceutical composition has no significant change in pH for at least about 1 month, at least about 2 months, at least about 3 months, at least about 6 months, at least about 9 months, at least about 1 year, at least about 2 years, at least about 3 years, at least about 4 years, or at least about 5 years. In some embodiments, the pH of the pharmaceutical composition changes by no more than 0.2 for at least about 1 month, at least about 2 months, at least about 3 months, at least about 6 months, at least about 9 months, at least about 1 year, at least about 2 years, at least about 3 years, at least about 4 years, or at least about 5 years. In other aspects, the pharmaceutical composition has no significant change in protein concentration for at least about 1 month, at least about 2 months, at least about 3 months, at least about 6 months, at least about 9 months, at least about 1 year, at least about 2 years, at least about 3 years, at least about 4 years, or at least about 5 years. In some embodiments, the protein concentration of the composition increases by no more than about 0.7 mg/ml for at least about 1 month, at least about 2 months, at least about 3 months, at least about 6 months, at least about 9 months, at least about 1 year, at least about 2 years, at least about 3 years, at least about 4 years, or at least about 5 years.

In other aspects, the pharmaceutical composition has a low particulate count for at least about 1 month, at least about 2 months, at least about 3 months, at least about 6 months, at least about 9 months, at least about 1 year, at least about 2 years, at least about 3 years, at least about 4 years, or at least about 5 years. In other aspects, the pharmaceutical composition has no significant decrease in the concentration of antibody monomer species for at least about 1 month, at least about 2 months, at least about 3 months, at least about 6 months, at least about 9 months, at least about 1 year, at least about 2 years, at least about 3 years, at least about 4 years, or at least about 5 years. In some embodiments, the concentration of antibody monomer species decreases by no more than about 10% for at least about 1 month, at least about 2 months, at least about 3 months, at least about 6 months, at least about 9 months, at least about 1 year, at least about 2 years, at least about 3 years, at least about 4 years, or at least about 5 years.

In other aspects, the pharmaceutical composition has no significant increase in the concentration of high molecular weight (HMW) antibody species for at least about 1 month, at least about 2 months, at least about 3 months, at least about 6 months, at least about 9 months, at least about 1 year, at least about 2 years, at least about 3 years, at least about 4 years, or at least about 5 years. In some embodiments, the concentration of HMW antibody species increases by no more than about 10% for at least about 1 month, at least about 2 months, at least about 3 months, at least about 6 months, at least about 9 months, at least about 1 year, at least about 2 years, at least about 3 years, at least about 4 years, or at least about 5 years. In other aspects, the pharmaceutical composition has no significant increase in the concentration of low molecular weight (LMW) antibody species for at least about 1 month, at least about 2 months, at least about 3 months, at least about 6 months, at least about 9 months, at least about 1 year, at least about 2 years, at least about 3 years, at least about 4 years, or at least about 5 years. In some embodiments, the concentration of LMW antibody increases by no more than about 3% for at least about 1 month, at least about 2 months, at least about 3 months, at least about 6 months, at least about 9 months, at least about 1 year, at least about 2 years, at least about 3 years, at least about 4 years, or at least about 5 years.

In yet other aspects, the pharmaceutical composition has no significant change in purity for at least about 1 month, at least about 2 months, at least about 3 months, at least about 6 months, at least about 9 months, at least about 1 year, at least about 2 years, at least about 3 years, at least about 4 years, or at least about 5 years. In some embodiments, the purity of the antibody decreases by no more than about 5%, about 4%, about 3%, about 2%, or about 1% for at least about 1 month, at least about 2 months, at least about 3 months, at least about 6 months, at least about 9 months, at least about 1 year, at least about 2 years, at least about 3 years, at least about 4 years, at least about 5 years. In other aspects, the pharmaceutical composition exhibits a change of an acidic peak that is less than about 15%, about 14%, about 13%, about 12%, about 11%, about 10%, about 9%, about 8%, about 7%, about 6%, about 5%, about 4%, about 3%, about 2%, or about 1%, for at least about 1 month, at least about 2 months, at least about 3 months, at least about 6 months, at least about 9 months, at least about 1 year, at least about 2 years, at least about 3 years, at least about 4 years, or at least about 5 years. In other aspects, the pharmaceutical composition exhibits no significant change in charge distribution for at least about 1 month, at least about 2 months, at least about 3 months, at least about 6 months, at least about 9 months, at least about 1 year, at least about 2 years, at least about 3 years, at least about 4 years, or at least about 5 years. In some embodiments, the change in charge distribution is no more than about 5%, about 4%, about 3%, about 2%, or about 1%.

Other aspects of the invention are directed to a method of making a pharmaceutical composition of the invention. In other aspects, the invention is directed to a method of modulating an immune response in a patient in need thereof comprising administering a pharmaceutical composition of the invention to the patient. In other aspects, the invention is directed to a method of treating a disease or condition comprising administering a pharmaceutical composition of the invention to a patient. In some embodiments, the disease or condition is an infectious disease. In some embodiments, the disease is cancer. In other embodiments, the cancer is melanoma cancer, renal cancer, prostate cancer, breast cancer, colon cancer, oral cancer, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and any combination thereof. In other embodiments, the lung cancer is small cell lung cancer or non-small cell lung cancer.

In other aspects of such methods, the cancer is refractory to treatment. In some embodiments, the cancer is refractory to treatment with an anti-PD1 antibody or anti-PD-L1 antibody. In other embodiments, the cancer is refractory to treatment with an immune-oncology agent.

In another aspect, methods of the invention are directed to a pharmaceutical composition comprising an anti-LAG-3 antibody or antigen binding fragment thereof, further comprise administering a pharmaceutical composition comprising an anti-PD-1 antibody, or anti-PD-L1 antibody, or antigen binding fragments thereof. In some embodiments, the pharmaceutical composition comprising the anti-LAG-3 antibody or antigen binding fragment thereof and the pharmaceutical composition comprising the anti-PD-1 antibody, or anti-PD-L1 antibody, or antigen binding fragments thereof are co-administered. In other embodiments, the pharmaceutical composition comprising the anti-LAG-3 antibody or antigen binding fragment thereof and the pharmaceutical composition comprising the anti-PD-1 antibody, or anti-PD-L1 antibody, or antigen binding fragments thereof are sequentially administered. In other embodiments, the pharmaceutical composition comprising the anti-LAG-3 antibody or antigen binding fragment thereof is administered prior to the pharmaceutical composition comprising the anti-PD-1 antibody, or anti-PD-L1 antibody, or antigen binding fragments thereof. In other embodiments, the anti-LAG-3 antibody or antigen-binding fragment thereof and the anti-PD-1 antibody, or anti-PD-L1 antibody, or antigen binding fragments thereof are administered as a first line of treatment. In other embodiments, the anti-LAG-3 antibody or antigen-binding fragment thereof and the anti-PD-1 antibody, or anti-PD-L1 antibody, or antigen binding fragments thereof are administered as a second line of treatment.

BRIEF DESCRIPTION OF THE FIGURES

(FIGS. 10B and 10C).

DETAILED DESCRIPTION OF THE INVENTION

Figure 1:
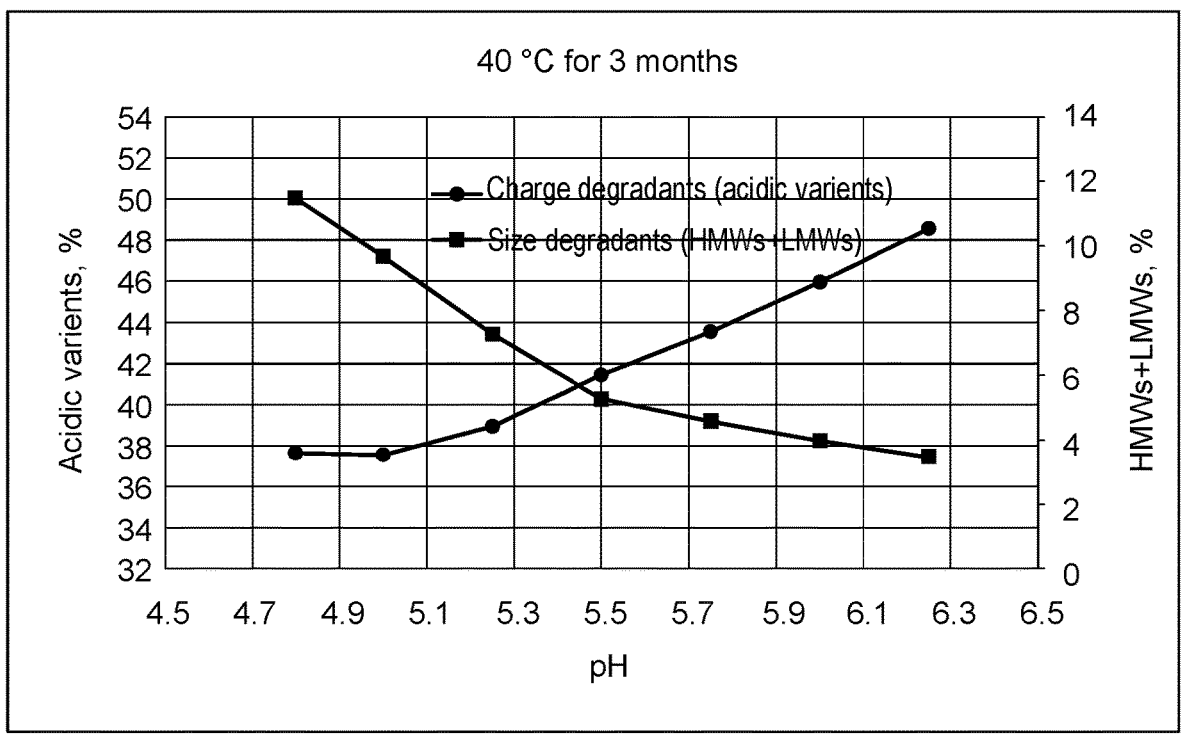
FIG. 1 shows the relationship of charge-related and size-related degradants with pH for an anti-LAG-3 antibody composition of the invention stored at 40° C. for 3 months.

The present invention relates pharmaceutical compositions comprising (i) an anti-LAG-3 antibody or an antigen binding fragment thereof, or (ii) an anti-LAG-3 antibody or an antigen binding fragment thereof and an anti-PD-1 antibody, or anti-PD-L1 antibody, or an antigen binding fragments thereof. The advantages of such formulations include greater stability.

Terms

In order that the present disclosure may be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of a composition comprising a therapeutic agent to a subject, using any of the various methods and delivery systems known to those skilled in the art. Preferred routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, preferably orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. A heavy chain may have the C-terminal lysine or not. Unless specified otherwise herein, the amino acids in the variable regions are numbered using the Kabat numbering system and those in the constant regions are numbered using the EU system.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man. Where not expressly stated, and unless the context indicates otherwise, the term "antibody" includes monospecific, bispecific, or multi-specific antibodies, as well as a single chain antibody. In embodiments, the antibody is a bispecific antibody. In other embodiments, the antibody is a monospecific antibody.

As used herein, an "IgG antibody" has the structure of a naturally occurring IgG antibody, i.e., it has the same number of heavy and light chains and disulfide bonds as a naturally occurring IgG antibody of the same subclass. For example, an anti-ICOS IgG1, IgG2, IgG3 or IgG4 antibody consists of two heavy chains (HCs) and two light chains (LCs), wherein the two heavy chains and light chains are linked by the same number and location of disulfide bridges that occur in naturally occurring IgG1, IgG2, IgG3 and IgG4 antibodies, respectively (unless the antibody has been mutated to modify the disulfide bonds).

The antibody may be an antibody that has been altered (e.g., by mutation, deletion, substitution, conjugation to a non-antibody moiety). For example, an antibody may include one or more variant amino acids (compared to a naturally occurring antibody) which change a property (e.g., a functional property) of the antibody. For example, numerous such alterations are known in the art which affect, e.g., half-life, effector function, and/or immune responses to the antibody in a patient. The term antibody also includes artificial polypeptide constructs which comprise at least one antibody-derived antigen binding site.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 may, however, have cross-reactivity to other antigens, such as PD-1 molecules from different species. Moreover, an isolated antibody may be substantially free of other cellular material and/or chemicals.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. MAbs may be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1 and an anti-CTLA-4 antibody binds specifically to CTLA-4.

An "antigen-binding portion" of an antibody (also called an "antigen-binding fragment") refers to one or more fragments of an antibody that retain the ability to bind specifically to the antigen bound by the whole antibody. It has been shown that the antigen-binding function of an antibody can be performed by fragments or portions of a full-length antibody. Examples of binding fragments encompassed within the term "antigen-binding portion" or "antigen-binding fragment" of an antibody, e.g., an anti-LAG-3 antibody described herein, include:

(1) a Fab fragment (fragment from papain cleavage) or a similar monovalent fragment consisting of the VL, VH, LC and CH1 domains;
(2) a F(ab')2 fragment (fragment from pepsin cleavage) or a similar bivalent fragment comprising two Fab fragments linked by a disulfide bridge at the hinge region;
(3) a Fd fragment consisting of the VH and CH1 domains;
(4) a Fv fragment consisting of the VL and VH domains of a single arm of an antibody,
(5) a single domain antibody (dAb) fragment (Ward et al., (1989) Nature 341:544-46), which consists of a VH domain;
(6) a bi-single domain antibody which consists of two VH domains linked by a hinge (dual-affinity re-targeting antibodies (DARTs));
(7) a dual variable domain immunoglobulin;
(8) an isolated complementarity determining region (CDR); and
(9) a combination of two or more isolated CDRs, which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" or "antigen-binding fragment" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream. A "cancer" or "cancer tissue" can include a tumor.

The term "tumor" as used herein refers to any mass of tissue that results from excessive cell growth or proliferation, either benign (non-cancerous) or malignant (cancerous), including pre-cancerous lesions A "disease" refers to any disorder of structure or function in an organism, for example a human that is not the direct result of a physical injury. An "infectious disease" is a disease that is caused by an organism such as a bacterium, fungus, parasite virus or other pathogen.

The use of the term "fixed dose" with regard to a composition of the invention means that two or more different antibodies in a single composition are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg anti-LAG-3 antibody or antigen binding fragment thereof, to anti-PD-1 antibody, anti-PD-L1 antibody, or antigen binding fragment thereof. For example, the 1:3 ratio of an anti-LAG-3 antibody or an antigen binding fragment thereof, to an anti-PD-1 antibody, anti-PD-L1 antibody, or antigen binding fragment thereof can mean that a vial can contain about 240 mg of anti-PD-1 antibody, anti-PD-L1 antibody, or antigen binding fragment thereof and 80 mg of anti-LAG-3 antibody or antigen binding fragment thereof; or about 3 mg/ml of anti-PD-1 antibody, anti-PD-L1 antibody, or antigen binding fragment thereof and 1 mg/ml of anti-LAG-3 antibody or antigen binding fragment thereof.

The use of the term "flat dose" with regard to the composition of the invention means a dose that is administered to a patient without regard for the weight or body surface area (BSA) of the patient. The flat dose is therefore not provided as a mg/kg dose, but rather as an absolute amount of the agent (e.g., the anti-LAG-3 antibody or antigen binding fragment thereof and/or anti-PD-1 antibody, anti-PD-L1 antibody, or antigen binding fragment thereof). For example, a 60 kg person and a 100 kg person would receive the same dose of the composition (e.g., 240 mg of an anti-PD-1 antibody, anti-PD-L1 antibody, or antigen binding fragment thereof and 80 mg of an anti-LAG-3 antibody or antigen binding fragment thereof in a single fixed dosing formulation vial containing both 240 mg of an anti-PD-1 antibody, anti-PD-L1 antibody, or antigen binding fragment thereof and 80 mg of an anti-LAG-3 antibody or antigen binding fragment thereof (or two fixed dosing formulation vials containing 120 mg of an anti-PD-1 antibody, anti-PD-L1 antibody, or antigen binding fragment thereof, and 40 mg of an anti-LAG-3 antibody or antigen binding fragment thereof, etc.)).

The term "weight based dose" as referred to herein means that a dose that is administered to a patient is calculated based on the weight of the patient. For example, when a patient with 60 kg body weight requires 4 mg/kg of an anti-PD-1 antibody in combination with 1.33 mg/kg of an anti-LAG-3 antibody, one can draw the appropriate amounts of the anti-PD-1 antibody (e.g., 240 mg) and the anti-LAG-3 antibody (e.g., 80 mg) at once from a 1:3 ratio fixed dosing formulation of an anti-LAG-3 antibody and an anti-PD-1 antibody.

The term "reference composition" as used herein refers to a composition comprising an anti-LAG-3 antibody (or, in antibody combination embodiments, an anti-PD-1 antibody, but not both). The reference composition can comprise the same components of the composition except the antibody (or, in antibody combination embodiments, the reference composition can comprise the same components of the composition except one of the antibodies). In other embodiments, the reference composition is a commercially available, corresponding composition, e.g., OPDIVO® or KEYTRUDA® for an anti-PD-1 antibody.

The term "LAG-3", "LAG3", or "Lymphocyte Activation Gene-3" refers to Lymphocyte Activation Gene-3. The term LAG-3 as used herein includes human LAG-3 (hLAG-3), variants, isoforms, orthologs, paralogs and species homologs of hLAG-3, and analogs having at least one common epitope with hLAG-3. The term LAG-3 as used herein includes variants, isoforms, homologs, orthologs and paralogs. For example, antibodies specific for a human LAG-3 protein may, in certain cases, cross-react with a LAG-3 protein from a species other than human. In other embodiments, the antibodies specific for a human LAG-3 protein may be completely specific for the human LAG-3 protein and may not exhibit species or other types of cross-reactivity, or may cross-react with LAG-3 from certain other species, but not all other species (e.g., cross-react with monkey LAG-3 but not mouse LAG-3). The term "human LAG-3" refers to human sequence LAG-3, such as the complete amino acid sequence of human LAG-3 having Genbank Accession No. NP 002277. The term "mouse LAG-3" refers to mouse sequence LAG-3, such as the complete amino acid sequence of mouse LAG-3 having Genbank Accession No. NP_032505. LAG-3 is also known in the art as, for example, CD223. The human LAG-3 sequence may differ from human LAG-3 of Genbank Accession No. NP_002277 by having, e.g., conserved mutations or mutations in non-conserved regions and the LAG-3 has substantially the same biological function as the human LAG-3 of Genbank Accession No. NP_002277. For example, a biological function of human LAG-3 is having an epitope in the extracellular domain of LAG-3 that is specifically bound by an antibody of the instant disclosure or a biological function of human LAG-3 is binding to WIC Class II molecules.

A particular human LAG-3 sequence will generally be at least 90% identical in amino acid sequence to human LAG-3 of GenBank Accession No. NP_002277 and contains amino acid residues that identify the amino acid sequence as being human when compared to LAG-3 amino acid sequences of other species (e.g., murine). In certain cases, a human LAG-3 can be at least 95%, or even at least 96%, 97%, 98%, or 99% identical in amino acid sequence to LAG-3 of GenBank Accession No. NP_002277. In certain embodiments, a human LAG-3 sequence will display no more than 10 amino acid differences from the LAG-3 sequence of GenBank Accession No. NP_002277. In certain embodiments, the human LAG-3 can display no more than 5, or even no more than 4, 3, 2, or 1 amino acid difference from the LAG-3 sequence of GenBank Accession No. NP_002277. Percent identity can be determined as described herein.

As used herein, the terms "Programmed Death 1," "Programmed Cell Death 1," "Protein PD-1," "PD-1," "PD1," "PDCD1," "hPD-1" and "hPD-I" are used interchangeably, and include variants, isoforms, species homologs of human PD-1, and analogs having at least one common epitope with PD-1. The complete PD-1 sequence can be found under GenBank Accession No. U64863 (SEQ ID NO:29).

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al. (2002) Curr. Opin. Immunol. 14: 391779-82; Bennett et al. (2003) J Immunol 170:711-8). The initial members of the family, CD28 and ICOS, were discovered by functional effects on augmenting T cell proliferation following the addition of monoclonal antibodies (Hutloff et al. Nature (1999); 397:263-266; Hansen et al. Immunogenics (1980); 10:247-260). PD-1 was discovered through screening for differential expression in apoptotic cells (Ishida et al. EMBO J (1992); 11:3887-95). The other members of the family, CTLA-4 and BTLA, were discovered through screening for differential expression in cytotoxic T lymphocytes and TH1 cells, respectively. CD28, ICOS and CTLA-4 all have an unpaired cysteine residue allowing for homodimerization. In contrast, PD-1 is suggested to exist as a monomer, lacking the unpaired cysteine residue characteristic in other CD28 family members.

The PD-1 gene is a 55 kDa type I transmembrane protein that is part of the Ig gene superfamily (Agata et al. (1996) Int Immunol 8:765-72). PD-1 contains a membrane proximal immunoreceptor tyrosine inhibitory motif (ITIM) and a membrane distal tyrosine-based switch motif (ITSM) (Thomas, M. L. (1995) J Exp Med 181:1953-6; Vivier, E and Daeron, M (1997) Immunol Today 18:286-91). Although structurally similar to CTLA-4, PD-1 lacks the MYPPPY motif (SEQ ID NO: 32) that is critical for B7-1 and B7-2 binding. Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other CD28 family members. PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

Consistent with PD-1 being an inhibitory member of the CD28 family, PD-1 deficient animals develop various autoimmune phenotypes, including autoimmune cardiomyopathy and a lupus-like syndrome with arthritis and nephritis (Nishimura et al. (1999) Immunity 11:141-51; Nishimura et al. (2001) Science 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al. (2003) J Exp Med 198:71-78; Prokunina and Alarcon-Riquelme (2004) Hum Mol Genet 13:R143; Nielsen et al.

(2004) Lupus 13:510). In a murine B cell tumor line, the ITSM of PD-1 was shown to be essential to block BCR-mediated $Ca^{2+}$-flux and tyrosine phosphorylation of downstream effector molecules (Okazaki et al. (2001) PNAS 98:13866-71).

"Programmed Death Ligand-1 (PD-L1)" is one of two cell surface glycoprotein ligands for PD-1 (the other being PD-L2) that down-regulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

The terms "Programmed Death Ligand-2" and "PD-L2" as used herein include human PD-L2 (hPD-L2), variants, isoforms, and species homologs of hPD-L2, and analogs having at least one common epitope with hPD-L2. The complete hPD-L2 sequence can be found under GenBank Accession No. Q9BQ51.

A "patient" as used herein includes any patient who is afflicted with a cancer (e.g., melanoma). The terms "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

The use of the alternative (e.g., "or") should be understood to mean either one, both, or any combination thereof of the alternatives. As used herein, the indefinite articles "a" or "an" should be understood to refer to "one or more" of any recited or enumerated component.

It is understood that wherever aspects are described herein with the language "comprising," otherwise analogous aspects described in terms of "consisting of" and/or "consisting essentially of" are also provided.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the invention are described in further detail in the following subsections.

Anti-LAG-3 Antibodies

Compositions of the invention include an anti-LAG-3 antibody or an antigen binding fragment thereof. Anti-LAG-3 antibodies or antigen binding fragments thereof of the invention bind to human LAG-3. Anti-LAG-3 antibodies (or VH/VL and CDR domains derived therefrom) suitable for use in the invention can be generated using methods well known in the art.

Alternatively, art-recognized anti-LAG-3 antibodies can be used. Antibodies that bind to LAG-3 have been disclosed in Int'l Publ. Nos. WO2015/042246 and WO2016/168716 and U.S. Publ. Nos. 2014/0093511 and 2011/0150892, which are herein incorporated by reference An anti-LAG-3 antibody useful for the present invention is 25F7 (described in U.S. Publ. No. 2011/0150892, also known as "LAG-3.1"). Other exemplary anti-LAG-3 antibodies and proteins that are useful for the present invention include IMP731, described in U.S. Publ. No. 2011/007023; MK-4280 (28G-10), described in Int'l Publ. No. WO2016/028672, REGN3767, described in Burova E., et al., *J. Immuno-Therapy Cancer,* 2016; 4(Supp. 1):P195; GSK2831781; IMP731, described in Int'l Publ. No. WO2014/140180; humanized BAP050, described in Int'l Publ. No. WO2017/019894; IMP-701; IMP321 (a LAG-3 fusion protein); Sym022, TSR-033, MGD013, BI754111, FS118, AVA-017 and GSK2831781. These and other anti-LAG-3 antibodies useful in the claimed invention can be found in, for example: WO2016/028672, WO2017/106129, WO2017062888, WO2009/044273, WO2018/069500, WO2016/126858, WO2014/179664, WO2016/200782, WO2015/200119, WO2017/019846, WO2017/198741, WO2017/220555, WO2017/220569, WO2018/071500, WO2017/015560; WO2017/025498, WO2017/087589, WO2017/087901, WO2018/083087, WO2017/149143, WO2017/219995, US2017/0260271, WO2017/086367, WO2017/086419, WO2018/034227, and WO2014/140180. The contents of these references are incorporated by reference herein.

Antibodies that compete with any of the above-referenced art-recognized antibodies for binding to LAG-3 also can be used.

An additional exemplary anti-LAG-3 antibody useful for the present invention is BMS-986016. BMS-986016 comprises heavy and light chains comprising the sequences shown in SEQ ID NOs:1 and 2 (see Table 1), respectively, or antigen binding fragments and variants thereof, as described in Int'l Appl. No. PCT/US13/48999, which is herein incorporated by reference.

In one embodiment, an anti-LAG-3 antibody useful for the composition cross-competes with, e.g., 25F7 or BMS-986016. In another embodiment, an anti-LAG-3 antibody useful for the composition binds to the same epitope as, e.g., 25F7 or BMS-986016.

In other embodiments, the anti-LAG-3 antibody or antigen binding fragment thereof has the heavy and light chain CDRs or variable regions of BMS-986016. Accordingly, in one embodiment, the anti-LAG-3 antibody or antigen binding fragment thereof comprises CDR1, CDR2, and/or CDR3 domains of the VH region of BMS-986016 having the sequence set forth in SEQ ID NO:3, and/or CDR1, CDR2 and/or CDR3 domains of the VL region of BMS-986016 having the sequence set forth in SEQ ID NO:5 (see Table 1). In another embodiment, the anti-LAG-3 antibody or antigen binding fragment thereof comprises CDR1, CDR2 and/or CDR3 domains comprising the sequences set forth in SEQ ID NOs:7, 8, and 9, respectively, and/or CDR1, CDR2 and/or CDR3 domains comprising the sequences set forth in SEQ ID NOs:10, 11, and 12, respectively (see Table 1). In another embodiment, the anti-LAG-3 antibody or antigen binding fragment thereof comprises VH and/or VL regions comprising the amino acid sequences set forth in SEQ ID NO:3 and/or SEQ ID NO: 5, respectively. In another embodiment, the anti-LAG-3 antibody or antigen binding fragment thereof comprises heavy chain variable (VH) and/or light chain variable (VL) regions encoded by the nucleic acid sequences set forth in SEQ ID NO:4 and/or SEQ ID NO:6, respectively (see Table 1). In another embodiment, the anti-LAG-3 antibody or antigen binding fragment thereof competes for binding with and/or binds to the same epitope on LAG-3 as the above-mentioned antibodies. In another embodiment, the anti-LAG-3 antibody or antigen binding fragment thereof binds an epitope of human LAG-3 comprising the amino acid sequence SEQ ID NO:14 (see Table 1). In another embodiment, the anti-LAG-3 antibody or antigen binding fragment thereof binds an epitope of human LAG-3 comprising the amino acid sequence SEQ ID NO:15 or SEQ ID NO:16 (see Table 1). In other embodiments, the anti-LAG-3 antibody or antigen binding fragment thereof comprises heavy and/or light chains comprising the sequences set forth in SEQ ID NOs:1 and 2, respectively (see Table 1).

In another embodiment, the antibody or antigen binding fragment thereof has at least about 90% variable region amino acid sequence identity with the above-mentioned antibodies (e.g., at least about 90%, 95% or 99% variable region identity with SEQ ID NO:3 or SEQ ID NO:5).

TABLE 1

| LAG-3 and anti-LAG-3 antibody sequences | |
|---|---|
| Heavy Chain Amino Acid Sequence; Anti-LAG-3 mAb (BMS-986016) (SEQ ID NO: 1) | QVQLQQWGAGLLKPSETLSLTCAVYGGSF SDYYWNWIRQPPGKGLEWIGEINHRGSTNS NPSLKSRVTLSLDTSKNQFSLKLRSVTAAD TAVYYCAFGYSDYEYNWFDPWGQGTLVT VSSASTKGPSVFPLAPCSRSTSESTAALGCL VKDYFPEPVTVSWNSGALTSGVHTFPAVL QSSGLYSLSSVVTVPSSSLGTKTYTCNVDH KPSNTKVDKRVESKYGPPCPPCPAPEFLGG PSVFLFPPKPKDTLMISRTPEVTCVVVDVSQ EDPEVQFNWYVDGVEVHNAKTKPREEQFN STYRVVSVLTVLHQDWLNGKEYKCKVSN KGLPSSIEKTISKAKGQPREPQVYTLPPSQE EMTKNQVSLTCLVKGFYPSDIAVEWESNG QPENNYKTTPPVLDSDGSFFLYSRLTVDKS RWQEGNVFSCSVMHEALHNHYTQKSLSLS LGK |
| Light Chain Amino Acid Sequence; Anti-LAG-3 mAb (BMS-986016) (SEQ ID NO: 2) | EIVLTQSPATLSLSPGERATLSCRASQSISSY LAWYQQKPGQAPRLLIYDASNRATGIPARF SGSGSGTDFTLTISSLEPEDFAVYYCQQRSN WPLTFGQGTNLEIKRTVAAPSVFIFPPSDEQ LKSGTASVVCLLNNFYPREAKVQWKVDN ALQSGNSQESVTEQDSKDSTYSLSSTLTLSK ADYEKHKVYACEVTHQGLSSPVTKSFNRG EC |
| Heavy Chain Variable Region (VH) Amino Acid Sequence; Anti-LAG-3 mAb (BMS-986016) (SEQ ID NO: 3) | QVQLQQWGAGLLKPSETLSLTCAVYGGSF SDYYWNWIRQPPGKGLEWIGEINHRGSTNS NPSLKSRVTLSLDTSKNQFSLKLRSVTAAD TAVYYCAFGYSDYEYNWFDPWGQGTLVT VSS |
| Heavy Chain Variable Region (VH) Nucleotide Sequence; Anti-LAG-3 mAb (BMS-986016) (SEQ ID NO: 4) | caggtgcagctacagcagtggggcgcaggactgttgaagccttcg gagaccctgtccctcacctgcgctgtctatggtgggtccttcagtgat tactactggaactggatccgccagcccccagggaaggggctgga gtggattggggaaatcaatcatcgtggaagcaccaactccaacccg tccctcaagagtcgagtcaccctatcactagacacgtccaagaacc agttctccctgaagctgaggtctgtgaccgccgcggacacggctgt gtattactgtgcgtttggatatagtgactacgagtacaactggttcga cccctggggccagggaaccctggtcaccgtctcctca |
| Light Chain Variable Region (VL) Amino Acid Sequence; Anti-LAG-3 mAb (BMS-986016) (SEQ ID NO: 5) | EIVLTQSPATLSLSPGERATLSCRASQSISSY LAWYQQKPGQAPRLLIYDASNRATGIPARF SGSGSGTDFTLTISSLEPEDFAVYYCQQRSN WPLTFGQGTNLEIK |
| Light Chain Variable Region (VL) Nucleotide Sequence; Anti-LAG-3 mAb (BMS-986016) (SEQ ID NO: 6) | gaaattgtgttgacacagtctccagccaccctgtctttgtctccaggg gaaagagccaccctctcctgcagggccagtcagagtattagcagct acttagcctggtaccaacagaaacctggccaggctcccaggctcct catctatgatgcatccaacagggccactggcatcccagccaggttc agtggcagtgggtctgggacagacttcactctcaccatcagcagcc |

TABLE 1-continued

| LAG-3 and anti-LAG-3 antibody sequences | |
|---|---|
| | tagagcctgaagattttgcagtttattactgtcagcagcgtagcaact<br>ggcctctcacttttggccaggggaccaacctggagatcaaa |
| Heavy Chain CDR1 Amino Acid<br>Sequence; Anti-LAG-3 mAb<br>(BMS-986016) (SEQ ID NO: 7) | DYYWN |
| Heavy Chain CDR2 Amino Acid<br>Sequence; Anti-LAG-3 mAb<br>(BMS-986016) (SEQ ID NO: 8) | EINHRGSTNSNPSLKS |
| Heavy Chain CDR3 Amino Acid<br>Sequence; Anti-LAG-3 mAb<br>(BMS-986016) (SEQ ID NO: 9) | GYSDYEYNWFDP |
| Light Chain CDR1 Amino Acid<br>Sequence; Anti-LAG-3 mAb<br>(BMS-986016) (SEQ ID NO: 10) | RASQSISSYLA |
| Light Chain CDR2 Amino Acid<br>Sequence; Anti-LAG-3 mAb<br>(BMS-986016) (SEQ ID NO: 11) | DASNRAT |
| Light Chain CDR3 Amino Acid<br>Sequence; Anti-LAG-3 mAb<br>(BMS-986016) (SEQ ID NO: 12) | QQRSNWPLT |
| Human LAG-3 Amino Acid<br>Sequence (SEQ ID NO: 13) | MWEAQFLGLLFLQPLWVAPVKPLQPGAEV<br>PVVWAQEGAPAQLPCSPTIPLQDLSLLRRA<br>GVTWQHQPDSGPPAAAPGHPLAPGPHPAA<br>PSSWGPRPRRYTVLSVGPGGLRSGRLPLQP<br>RVQLDERGRQRGDFSLWLRPARRADAGEY<br>RAAVHLRDRALSCRLRLRLGQASMTASPP<br>GSLRASDWVILNCSFSRPDRPASVHWFRNR<br>GQGRVPVRESPHHHLAESFLFLPQVSPMDS<br>GPWGCILTYRDGFNVSIMYNLTVLGLEPPT<br>PLTVYAGAGSRVGLPCRLPAGVGTRSFLTA<br>KWTPPGGGPDLLVTGDNGDFTLRLEDVSQ<br>AQAGTYTCHIHLQEQQLNATVTLAIITVTP<br>KSFGSPGSLGKLLCEVTPVSGQERFVWSSL<br>DTPSQRSFSGPWLEAQEAQLLSQPWQCQL<br>YQGERLLGAAVYFTELSSPGAQRSGRAPG<br>ALPAGHLLLFLTLGVLSLLLLVTGAFGFHL<br>WRRQWRPRRFSALEQGIHPPQAQSKIEELE<br>QEPEPEPEPEPEPEPEPEPEQL |
| LAG-3 Epitope (SEQ ID NO: 14) | PGHPLAPG |
| LAG-3 Epitope (SEQ ID NO: 15) | HPAAPSSW |
| LAG-3 Epitope (SEQ ID NO: 16) | PAAPSSWG |
| Heavy Chain Nucleotide<br>Sequence; Anti-LAG-3 mAb<br>(BMS-986016) (SEQ ID NO: 30) | caggtgcagctacagcagtggggcgcaggactgttgaagccttcg<br>gagaccctgtccctcacctgcgctgtctatggtgggtccttcagtgat<br>tactactggaactggatccgccagcccccagggaaggggctgga<br>gtggattggggaaatcaatcatcgtggaagcaccaactccaacccg<br>tccctcaagagtcgagtcaccctatcactagacacgtccaagaacc<br>agttctccctgaagctgaggtctgtgaccgccgcggacacggctgt<br>gtattactgtgcgtttggatatagtgactacgagtacaactggttcga<br>cccctgggccagggaaccctggtcaccgtctcctcagctagcac<br>caagggcccatccgtcttccccctggcgccctgctccaggagcac<br>ctccgagagcacagccgccctgggctgcctggtcaaggactactt<br>ccccgaaccggtgacggtgtcgtggaactcaggcgccctgacca<br>gcggcgtgcacaccttcccggctgtcctacagtcctcaggactcta<br>ctccctcagcagcgtggtgaccgtgccctccagcagcttgggcac<br>gaagacctacacctgcaacgtagatcacaagcccagcaacaccaa<br>ggtggacaagagagttgagtccaaatatggtcccccatgcccacca<br>tgcccagcacctgagttcctggggggaccatcagtcttcctgttccc<br>cccaaaacccaaggacactctcatgatctcccggacccctgaggtc<br>acgtgcgtggtggtggacgtgagccaggaagaccccgaggtcca<br>gttcaactggtacgtggatggcgtggaggtgcataatgccaagaca<br>aagccgcgggaggagcagttcaacagcacgtaccgtgtggtcag<br>cgtcctcaccgtcctgcaccaggactggctgaacggcaaggagta<br>caagtgcaaggtctccaacaaaggcctcccgtcctccatcgagaaa<br>accatctccaaagccaaagggcagccccgagagccacaggtgta<br>caccctgcccccatcccaggaggagatgaccaagaaccaggtca<br>gcctgacctgcctggtcaaaggcttctaccccagcgacatcgccgt<br>ggagtgggagagcaatgggcagccggagaacaactacaagacc |

TABLE 1-continued

LAG-3 and anti-LAG-3 antibody sequences

| | |
|---|---|
| | acgcctcccgtgctggactccgacggctccttcttcctctacagcag<br>gctaaccgtggacaagagcaggtggcaggaggggaatgtcttctc<br>atgctccgtgatgcatgaggctctgcacaaccactacacacagaag<br>agcctctccctgtctctgggtaaatga |
| Light Chain Nucleotide<br>Sequence; Anti-LAG-3 mAb<br>(BMS-986016) (SEQ ID NO: 31) | gaaattgtgttgacacagtctccagccaccctgtctttgtctccaggg<br>gaaagagccaccctctcctgcaggccagtcagagtattagcagct<br>acttagcctggtaccaacagaaacctggccaggctcccaggctcct<br>catctatgatgcatccaacagggccactggcatcccagccaggttc<br>agtggcagtgggtctgggacagacttcactctcaccatcagcagc<br>tagagcctgaagattttgcagtttattactgtcagcagcgtagcaact<br>ggcctctcacttttggccaggggaccaacctggagatcaaacgtac<br>ggtggctgcaccatctgtcttcatcttcccgccatctgatgagcagtt<br>gaaatctggaactgcctctgttgtgtgcctgctgaataacttctatccc<br>agagaggccaaagtacagtggaaggtggataacgccctccaatcg<br>ggtaactcccaggagagtgtcacagagcaggacagcaaggacag<br>cacctacagcctcagcagcaccctgacgctgagcaaagcagacta<br>cgagaaacacaaagtctacgcctgcgaagtcacccatcagggcct<br>gagctcgcccgtcacaaagagcttcaacaggggagagtgttag |
| Motif (SEQ ID NO: 32) | MYPPPY |

Antibodies that compete with any of the above-referenced art-recognized antibodies for binding to LAG-3 also can be used.

In some embodiments, the anti-LAG-3 antibody is a bispecific antibody. In some embodiments, the anti-LAG-3 antibody is a bispecific antibody that binds both PD-1 and LAG-3

Anti-PD-1 and Anti-PD-L1 Antibodies

Some compositions of the invention include an anti-PD-1 antibody, or an anti-PD-L1 antibody, or antigen binding fragments thereof in combination with an anti-LAG-3 antibody or antigen binding fragment thereof. PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

Human monoclonal antibodies (HuMAbs) that bind specifically to PD-1 with high affinity have been disclosed in U.S. Pat. Nos. 8,008,449 and 8,779,105. Other anti-PD-1 mAbs have been described in, for example, U.S. Pat. Nos. 6,808,710, 7,488,802, 8,168,757 and 8,354,509, and PCT Publication Nos. WO2012/145493 and WO2016/168716. Each of the anti-PD-1 HuMAbs disclosed in U.S. Pat. No. 8,008,449 has been demonstrated to exhibit one or more of the following characteristics: (a) binds to human PD-1 with a $K_D$ of $1 \times 10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates Ab responses; and (j) inhibits tumor cell growth in vivo. Anti-PD-1 antibodies useful for the present invention include mAbs that bind specifically to human PD-1 and exhibit at least one, preferably at least five, of the preceding characteristics.

In one embodiment, the anti-PD-1 antibody is nivolumab. Nivolumab (also known as "OPDIVO®"; BMS-936558; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56). In another embodiment, the anti-PD-1 antibody or fragment thereof cross-competes with nivolumab. In other embodiments, the anti-PD-1 antibody or fragment thereof binds to the same epitope as nivolumab. In certain embodiments, the anti-PD-1 antibody has the same CDRs as nivolumab.

Anti-human-PD-1 antibodies (or VH and/or VL domains derived therefrom) suitable for use in the invention can be generated using methods well known in the art. Alternatively, art recognized anti-PD-1 antibodies can be used. For example, monoclonal antibodies 5C4 (referred to herein as Nivolumab or BMS-936558), 17D8, 2D3, 4H1, 4A11, 7D3, and 5F4, described in WO 2006/121168, the teachings of which are hereby incorporated by reference, can be used. Other known PD-1 antibodies include lambrolizumab (MK-3475) described in WO 2008/156712, and AMP-514 described in WO 2012/145493. Further known anti-PD-1 antibodies and other PD-1 inhibitors include those described in WO 2009/014708, WO 03/099196, WO 2009/114335 and WO 2011/161699. Another known anti-PD-1 antibody is pidilizumab (CT-011). Antibodies or antigen binding fragments thereof that compete with any of these antibodies or inhibitors for binding to PD-1 also can be used.

An exemplary anti-PD-1 antibody is BMS-936558 comprising heavy and light chains comprising the sequences shown in SEQ ID NOs:17 and 18, respectively, or antigen binding fragments and variants thereof (see Table 2). In other embodiments, the antibody or antigen binding fragment thereof has heavy and light chain CDRs or variable regions of BMS-936558. Accordingly, in one embodiment, the antibody or antigen binding fragment thereof comprises CDR1, CDR2, and/or CDR3 domains of the VH of BMS-936558 having the sequence set forth in SEQ ID NO:19, and/or CDR1, CDR2 and/or CDR3 domains of the VL of BMS-936558 having the sequence set forth in SEQ ID NO:21 (see Table 2). In another embodiment, the antibody or antigen binding fragment thereof comprises CDR1, CDR2 and/or CDR3 domains comprising the sequences set forth in SEQ ID NOs:23, 24, and 25, respectively, and/or CDR1, CDR2 and/or CDR3 domains comprising the sequences set forth in SEQ ID NOs:26, 27 and 28, respectively (see Table 2). In another embodiment, the antibody or antigen binding fragment thereof comprises VH and/or VL regions comprising the amino acid sequences set forth in SEQ ID NO: 19 and/or SEQ ID NO: 21, respectively. In another embodiment, the antibody or antigen binding fragment thereof comprises heavy chain variable (VH) and/or light chain variable (VL) regions encoded by the nucleic acid sequences set forth in SEQ ID NO:20 and/or SEQ ID NO:22, respectively (see Table 2). In another embodiment, the antibody or antigen binding fragment thereof competes for binding with and/or binds to the same epitope on PD-1 as the above-mentioned antibodies. In another embodiment, the antibody or antigen binding fragment thereof has at least about 90% variable region amino acid sequence identity with the above-mentioned antibodies (e.g., at least about 90%, 95% or 99% variable region identity with SEQ ID NO:19 or SEQ ID NO:21).

In another embodiment, the anti-PD-1 antibody is pembrolizumab. Pembrolizumab is a humanized monoclonal IgG4 (S228P) antibody directed against human cell surface receptor PD-1 (programmed death-1 or programmed cell death-1). Pembrolizumab is described, for example, in U.S. Pat. Nos. 8,354,509 and 8,900,587.

In another embodiment, the anti-PD-1 antibody or antigen binding fragment thereof cross-competes with pembrolizumab. In some embodiments, the anti-PD-1 antibody or antigen binding fragment thereof binds to the same epitope as pembrolizumab. In certain embodiments, the anti-PD-1 antibody or antigen binding fragment thereof has the same CDRs as pembrolizumab. In another embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also http://www.cancer.gov/drugdictionary?cdrid=695789 (last accessed: May 25, 2017). Pembrolizumab has been approved by the FDA for the treatment of relapsed or refractory melanoma.

In other embodiments, the anti-PD-1 antibody or antigen binding fragment thereof cross-competes with MEDI0608. In still other embodiments, the anti-PD-1 antibody or antigen binding fragment thereof binds to the same epitope as MEDI0608. In certain embodiments, the anti-PD-1 antibody has the same CDRs as MEDI0608. In other embodiments, the anti-PD-1 antibody is MEDI0608 (formerly AMP-514), which is a monoclonal antibody. MEDI0608 is described, for example, in U.S. Pat. No. 8,609,089 or in http://www.cancer.gov/drugdictionary?cdrid=756047 (last accessed May 25, 2017).

In other embodiments, the anti-PD-1 antibody or antigen binding fragment thereof cross-competes with BGB-A317. In some embodiments, the anti-PD-1 antibody or antigen binding fragment thereof binds the same epitope as BGB-A317. In certain embodiments, the anti-PD-1 antibody or antigen binding fragment thereof has the same CDRs as BGB-A317. In certain embodiments, the anti-PD-1 antibody or antigen binding fragment thereof is BGB-A317, which is a humanized monoclonal antibody. BGB-A317 is described in U.S. Publ. No. 2015/0079109.

Anti-PD-1 antibodies useful for the disclosed compositions also include isolated antibodies that bind specifically to human PD-1 and cross-compete for binding to human PD-1 with nivolumab (see, e.g., U.S. Pat. Nos. 8,008,449 and 8,779,105; Int'l Pub. No. WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar to those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., Int'l Pub. No. WO 2013/173223).

In certain embodiments, antibodies or antigen binding fragments thereof that cross-compete for binding to human PD-1 with, or bind to the same epitope region of human PD-1 as, nivolumab are mAbs. For administration to human subjects, these cross-competing antibodies can be chimeric antibodies, or humanized or human antibodies. Such chimeric, humanized or human mAbs can be prepared and isolated by methods well known in the art.

Anti-PD-1 antibodies useful for the compositions of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; and (iv) a Fv fragment consisting of the VL and VH domains of a single arm of an antibody.

Anti-PD-1 antibodies suitable for use in the disclosed compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-1 antibody or antigen-binding portion thereof is a chimeric, humanized or human monoclonal antibody or a portion thereof. In certain embodiments, the antibody is a humanized antibody. In other embodiments, the antibody is a human antibody. Antibodies of an IgG1, IgG2, IgG3 or IgG4 isotype can be used.

In certain embodiments, the anti-PD-1 antibody or antigen binding fragment thereof comprises a heavy chain constant region which is of a human IgG1 or IgG4 isotype. In certain other embodiments, the sequence of the IgG4 heavy chain constant region of the anti-PD-1 antibody or antigen binding fragment thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014). In yet other embodiments, the antibody comprises a light chain constant region which is a human kappa or lambda constant region. In other embodiments, the anti-PD-1 antibody or antigen binding fragment thereof is a mAb or an antigen-binding portion thereof. In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0608 (formerly AMP-514), AMP-224, or Pidilizumab (CT-011). Other known PD-1 antibodies include lambrolizumab (MK-3475) described in, for example, WO 2008/156712, and AMP-514 described in, for example, WO 2012/145493. Further known anti-PD-1 antibodies and other PD-1 inhibitors include those described in, for example, WO 2009/014708, WO 03/099196, WO 2009/114335 and WO 2011/161699. In one embodiment, the anti-PD-1 antibody is REGN2810. In one embodiment, the anti-PD-1 antibody is PDR001. Another known anti-PD-1 antibody is pidilizumab (CT-011). Each of the above references are incorporated by reference. Antibodies or antigen binding fragments thereof that compete with any of these antibodies or inhibitors for binding to PD-1 also can be used.

Other anti-PD-1 monoclonal antibodies have been described in, for example, U.S. Pat. Nos. 6,808,710, 7,488,802, 8,168,757 and 8,354,509, US Publication No. 2016/0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540, each of which are herein incorporated by reference.

In some embodiments, the anti-PD-1 antibody is selected from the group consisting of nivolumab (also known as OPDIVO®, 5C4, BMS-936558, MDX-1106, and ONO-4538), pembrolizumab (Merck; also known as KEYTRUDA®, lambrolizumab, and MK-3475; see WO2008/156712), PDR001 (Novartis; see WO 2015/112900), MEDI-0680 (AstraZeneca; also known as AMP-514; see WO 2012/145493), cemiplimab (Regeneron; also known as REGN-2810; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (Jiangsu Hengrui Medicine; also known as SHR-1210; see WO 2015/085847; Si-Yang Liu et al., *J. Hematol. Oncol.* 10:136 (2017)), TSR-042 (Tesaro Biopharmaceutical; also known as ANB011; see WO2014/179664), GLS-010 (Wuxi/Harbin Gloria Pharmaceuticals; also known as WBP3055; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGA012 (Macrogenics, see WO 2017/19846), and IBI308 (Innovent; see WO 2017/024465, WO 2017/025016, WO 2017/132825, and WO 2017/133540). Each of the above references are herein incorporated by reference.

In embodiments, the anti-PD-1 antibody is a bispecific antibody. In embodiments, the anti-PD-1 antibody is a bispecific antibody that binds both PD-1 and LAG-3.

Because anti-PD-1 antibodies and anti-PD-L1 antibodies target the same signaling pathway and have been shown in clinical trials to exhibit similar levels of efficacy in a variety of cancers, an anti-PD-L1 antibody or antigen binding fragment thereof can be substituted for an anti-PD-1 antibody or antigen binding fragment thereof in any of the therapeutic methods or compositions disclosed herein.

Anti-human-PD-L1 antibodies (or VH and/or VL domains derived therefrom) suitable for use in the invention can be generated using methods well known in the art. Alternatively, art recognized anti-PD-L1 antibodies can be used. For example, human anti-PD-L1 antibodies disclosed in U.S. Pat. No. 7,943,743, the contents of which are hereby incorporated by reference, can be used. Such anti-PD-L1 antibodies include 3G10, 12A4 (also referred to as BMS-936559), 10A5, 5F8, 10H10, 1B12, 7H1, 11E6, 12B7, and 13G4. Other art recognized anti-PD-L1 antibodies which can be used include those described in, for example, U.S. Pat. Nos. 7,635,757 and 8,217,149, U.S. Publication No. 2009/0317368, and PCT Publication Nos. WO 2011/066389 and WO 2012/145493, each of which are herein incorporated by reference. Other examples of an anti-PD-L1 antibody include atezolizumab (TECENTRIQ; RG7446), or durvalumab (IMFINZI; MEDI4736). Antibodies or antigen binding fragments thereof that compete with any of these art-recognized antibodies or inhibitors for binding to PD-L1 also can be used.

Examples of anti-PD-L1 antibodies useful in the methods of the present disclosure include the antibodies disclosed in U.S. Pat. No. 9,580,507, which is herein incorporated by reference. Anti-PD-L1 human monoclonal antibodies disclosed in U.S. Pat. No. 9,580,507 have been demonstrated to exhibit one or more of the following characteristics: (a) bind to human PD-L1 with a KD of $1\times10^{-7}$ M or less, as determined by surface plasmon resonance using a Biacore biosensor system; (b) increase T-cell proliferation in a Mixed Lymphocyte Reaction (MLR) assay; (c) increase interferon-γ production in an MLR assay; (d) increase IL-2 secretion in an MLR assay; (e) stimulate antibody responses; and (f) reverse the effect of T regulatory cells on T cell effector cells and/or dendritic cells. Anti-PD-L1 antibodies usable in the present invention include monoclonal antibodies that bind specifically to human PD-L1 and exhibit at least one, in some embodiments, at least five, of the preceding characteristics.

In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446 and atezolizumab) (see, e.g., Herbst et al. 2013 *J Clin Oncol* 31(suppl):3000; U.S. Pat. No. 8,217,149), MEDI4736 (Khleif, 2013, In: Proceedings from the European Cancer Congress 2013; Sep. 27-Oct. 1, 2013; Amsterdam, The Netherlands. Abstract 802), or MSB0010718C (also called Avelumab; see US 2014/0341917). In certain embodiments, antibodies that cross-compete for binding to human PD-L1 with, or bind to the same epitope region of human PD-L1 as the above-references PD-L1 antibodies are mAbs. For administration to human subjects, these cross-competing antibodies can be chimeric antibodies, or can be humanized or human antibodies. Such chimeric, humanized or human mAbs can be prepared and isolated by methods well known in the art. In certain embodiments, the anti-PD-L1 antibody is selected from the group consisting of BMS- 936559 (also known as 12A4, MDX-1105; see, e.g., U.S. Pat. No. 7,943,743 and WO 2013/173223), atezolizumab (Roche; also known as TECENTRIQ®; MPDL3280A, RG7446; see U.S. Pat. No. 8,217,149; see, also, Herbst et al. (2013) J Clin Oncol 31(suppl):3000), durvalumab (AstraZeneca; also known as IMFINZI™, MEDI-4736; see, e.g., WO 2011/066389), avelumab (Pfizer; also known as BAVENCIO®, MSB-0010718C; see, e.g., WO 2013/079174), STI-1014 (Sorrento; see, e.g., WO2013/181634), CX-072 (Cytomx; see, e.g., WO2016/149201), KN035 (3D Med/Alphamab; see Zhang et al., Cell Discov. 7:3 (March 2017), LY3300054 (Eli Lilly Co.; see, e.g., WO 2017/034916), and CK-301 (Checkpoint Therapeutics; see Gorelik et al., AACR:Abstract 4606 (April 2016)). The above references are herein incorporated by reference.

In certain embodiments, the PD-L1 antibody is atezolizumab (TECENTRIQ®). Atezolizumab is a fully humanized IgG1 monoclonal anti-PD-L1 antibody.

In certain embodiments, the PD-L1 antibody is durvalumab (IMFINZI™). Durvalumab is a human IgG1 kappa monoclonal anti-PD-L1 antibody.

In certain embodiments, the PD-L1 antibody is avelumab (BAVENCIO®). Avelumab is a human IgG1 lambda monoclonal anti-PD-L1 antibody.

In other embodiments, the anti-PD-L1 monoclonal antibody is selected from the group consisting of 28-8, 28-1, 28-12, 29-8, 5H1, and any combination thereof.

Anti-PD-L1 antibodies usable in the disclosed methods also include isolated antibodies that bind specifically to human PD-L1 and cross-compete for binding to human PD-L1 with any anti-PD-L1 antibody disclosed herein, e.g., atezolizumab, durvalumab, and/or avelumab. In some embodiments, the anti-PD-L1 antibody binds the same epitope as any of the anti-PD-L1 antibodies described herein, e.g., atezolizumab, durvalumab, and/or avelumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., atezolizumab and/or avelumab, by virtue of their binding to the same epitope region of PD-L1. Cross-competing antibodies can be readily identified based on their ability to cross-compete with atezolizumab and/or avelumab in standard PD-L1 binding assays such as Biacore analysis, ELISA assays or flow cytometry (see, e.g., WO 2013/173223).

In certain embodiments, the antibodies that cross-compete for binding to human PD-L1 with, or bind to the same epitope region of human PD-L1 antibody as, atezolizumab, durvalumab, and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies usable in the methods of the disclosed invention also include antigen-binding portions of the above antibodies. It has been amply demonstrated that the antigen-binding function of an antibody can be performed by fragments of a full-length antibody.

Anti-PD-L1 antibodies suitable for use in the disclosed methods or compositions are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and up-regulating the immune system. In certain embodiments, the anti-PD-L1 antibody or antigen-binding portion thereof cross-competes with atezolizumab, durvalumab, and/or avelumab for binding to human PD-L1.

TABLE 2

| PD-1 and anti-PD-1 | antibody sequences |
|---|---|
| Heavy Chain Amino Acid Sequence; Anti-PD-1 mAb (BMS936558) (SEQ ID NO: 17) | QVQLVESGGGVVQPGRSLRLDCKASGITFS NSGMHWVRQAPGKGLEWVAVIWYDGSKR YYADSVKGRFTISRDNSKNTLFLQMNSLRA EDTAVYYCATNDDYWGQGTLVTVSSASTK GPSVFPLAPCSRSTSESTAALGCLVKDYFPEP VTVSWNSGALTSGVHTFPAVLQSSGLYSLSS VVTVPSSSLGTKTYTCNVDHKPSNTKVDKR VESKYGPPCPPCPAPEFLGGPSVFLFPPKPKD TLMISRTPEVTCVVVDVSQEDPEVQFNWYV DGVEVHNAKTKPREEQFNSTYRVVSVLTVL HQDWLNGKEYKCKVSNKGLPSSIEKTISKA KGQPREPQVYTLPPSQEEMTKNQVSLTCLV KGFYPSDIAVEWESNGQPENNYKTTPPVLD SDGSFFLYSRLTVDKSRWQEGNVFSCSVMH EALHNHYTQKSLSLSLGK |
| Light Chain Amino Acid Sequence; Anti-PD-1 mAb (BMS936558) (SEQ ID NO: 18) | EIVLTQSPATLSLSPGERATLSCRASQSVSSY LAWYQQKPGQAPRLLIYDASNRATGIPARF SGSGSGTDFTLTISSLEPEDFAVYYCQQSSN WPRTFGQGTKVEIKRTVAAPSVFIFPPSDEQ LKSGTASVVCLLNNFYPREAKVQWKVDNA LQSGNSQESVTEQDSKDSTYSLSSTLLSKAD YEKHKVYACEVTHQGLSSPVTKSFNRGEC |
| Heavy Chain Variable Region (VH) Amino Acid Sequence; Anti-PD-1 mAb (BMS936558) (SEQ ID NO: 19) | QVQLVESGGGVVQPGRSLRLDCKASGITFS NSGMHWVRQAPGKGLEWVAVIWYDGSKR YYADSVKGRFTISRDNSKNTLFLQMNSLRA EDTAVYYCATNDDYWGQGTLVTVSS |

TABLE 2-continued

| PD-1 and anti-PD-1 | antibody sequences |
|---|---|
| Heavy Chain Variable Region (VH) Nucleotide Sequence; Anti-PD-1 mAb (BMS936558) (SEQ ID NO: 20) | Caggtgcagctggtggagtctgggggaggcgtggtccagcctggg aggtccctgagactcgactgtaaagcgtctggaatcaccttcagtaac tctggcatgcactgggtccgccaggctccaggcaagggctggagt gggtggcagttatttggtatgatggaagtaaaagatactatgcagact ccgtgaagggccgattcaccatctccagagacaattccaagaacac gctgtttctgcaaatgaacagcctgagagccgaggacacggctgtgt attactgtgcgacaaacgacgactactggggccagggaaccctggt caccgtctcctca |
| Light Chain Variable Region (VL) Amino Acid Sequence; Anti-PD-1 mAb (BMS936558) (SEQ ID NO: 21) | EIVLTQSPATLSLSPGERATLSCRASQSVSSY LAWYQQKPGQAPRLLIYDASNRATGIPARF SGSGSGTDFTLTISSLEPEDFAVYYCQQSSN WPRTFGQGTKVEIK |
| Synthetic: Light Chain Variable Region (VL) Nucleotide Sequence; Anti-PD-1 mAb (BMS936558) (SEQ ID NO: 22) | gaaattgtgttgacacagtctccagccaccctgtctttgtctccaggg aaagagccaccctctcctgcagggccagtcagagtgttagtagttact tagcctggtaccaacagaaacctggccaggctcccaggctcctcatc tatgatgcatccaacagggccactggcatcccagccaggttcagtgg cagtgggtctgggacagacttcactctcaccatcagcagcctagagc ctgaagattttgcagtttattactgtcagcagagtagcaactggcctcg gacgttcggccaagggaccaaggtggaaatcaaa |
| Heavy Chain CDR1 Amino Acid Sequence; Anti-PD-1 mAb (BMS936558) (SEQ ID NO: 23) | NSGMH |
| Heavy Chain CDR2 Amino Acid Sequence; Anti-PD-1 mAb (BMS936558) (SEQ ID NO: 24) | VIWYDGSKRYYADSVKG |
| Heavy Chain CDR3 Amino Acid Sequence; Anti-PD-1 mAb (BMS936558) (SEQ ID NO: 25) | NDDY |
| Light Chain CDR1 Amino Acid Sequence; Anti-PD-1 mAb (BMS936558) (SEQ ID NO: 26) | RASQSVSSYLA |
| Light Chain CDR2 Amino Acid Sequence; Anti-PD-1 mAb (BMS936558) (SEQ ID NO: 27) | DASNRAT |
| Light Chain CDR3 Amino Acid Sequence; Anti-PD-1 mAb (BMS936558) (SEQ ID NO: 28) | QQSSNWPRT |
| Complete PD-1 sequence (SEQ ID NO: 29) | agtttcccttccgctcacctccgcctgagcagtggagaaggcggcac tctggtggggctgctccaggcatgcagatcccacaggcgccctggc cagtcgtctgggcggtgctacaactgggctggcggccaggatggtt cttagactccccagacaggccctggaaccccccaccttcttcccag ccctgctcgtggtgaccaaggggacaacgccaccttcacctgcag cttctccaacacatcggagagcttcgtgctaaactggtaccgcatgag ccccagcaaccagacggacaagctggccgcgccttccccgaggaccg cagccagcccggccaggactgccgcttccgtgtcacacaactgccc aacgggcgtgacttccacatgagcgtggtcagggcccggcgcaat gacagcggcacctacctctgtggggccatctccctggccccccaagg cgcagatcaaagagagcctgcgggcagagctcagggtgacgag agaagggcagaagtgcccacagcccaccccagcccctcacccag gccagccggccagttccaaaccctggtggttggtgtcgtgggcggc ctgctgggcagcctggtgctgctagtctgggtcctggccgtcatctgc tcccgggccgcacgaggacaataggagccaggcgcaccggcca gcccctgaaggaggaccccctcagccgtgcctgtgttctctgtggact atggggagctggatttccagtggcgagagaagacccccggagcccc ccgtgccctgtgtccctgagcagacggagtatgccaccattgtctttc ctagcggaatgggcacctcatcccccgcccgcaggggctcagccg acgccctcggagtgcccagccactgaggcctgaggatggacact gctcttggcccctctgaccggcttccttggccaccagtgttctgcaga ccctccaccatgagcccgggtcagcgcatttcctcaggagaagcag gcagggtgcaggccattgcaggccgtccaggggctgagctgcctg ggggcgaccggggctccagcctgcacctgcaccaggcacagccc caccacaggactcatgtctcaatgcccacagtgagcccaggcagca ggtgtcaccgtcccctacagggagggccagatgcagtcactgcttca ggtcctgccagcacagagctgcctgcgtccagctccctgaatctctg ctgctgctgctgctgctgctgctgcctgcggccccggggctgaag gcgccgtgccctgcctgacgccccggagcctcctgcctgaacttg ggggctggttggagatggccttggagcagccaaggtgcccctggc agtggcatcccgaaacgccctggacgcagggcccaagactgggca caggagtgggaggtacatgggctggggactccccaggagttatct |

TABLE 2-continued

| PD-1 and anti-PD-1 | antibody sequences |
|---|---|
| | gctccctgcaggcctagagaagtttcagggaaggtcagaagagctc<br>ctggctgtggtgggcagggcaggaaaccccctcccacctttacacatg<br>cccaggcagcacctcaggccctttgtggggcagggaagctgaggc<br>agtaagcgggcaggcagagctggaggcctttcaggccagccagca<br>ctctggcctcctgccgccgcattccaccccagccctcacaccactc<br>gggagagggacatcctacggtcccaaggtcaggagggcagggct<br>ggggttgactcaggcccctcccagctgtggccacctgggtgttggg<br>agggcagaagtgcaggcacctagggcccccatgtgcccaccctg<br>ggagctctccttggaacccattcctgaaattatttaaaggggttggccg<br>ggctcccaccagggcctgggtgggaaggtacaggcgttcccccgg<br>ggcctagtaccccccgcgtggcctatccactcctcacatccacacact<br>gcaccccactcctggggcagggccaccagcatccaggcggcca<br>gcaggcacctgagtggctgggacaagggatccccccttccctgtggtt<br>ctattatattataattataattaaatatgagagcatgct |

In some embodiments, the anti-LAG-3 antibody or antigen binding fragment thereof is combined with an anti-PD-1 antibody, anti-PD-L1 antibody, or antigen binding fragment thereof. In some embodiments, the anti-LAG-3 antibody is BMS-986016 and the anti-PD-1 antibody is nivolumab, the anti-LAG-3 antibody is MK-4280 and the anti-PD-1 antibody is pembrolizumab, the anti-LAG-3 antibody is REGN3767 and the anti-PD-1 antibody is REGN2810, the anti-LAG-3 antibody is LAG525 and the anti-PD-1 is REGN2810, or the anti-LAG-3 antibody is LAG525 and the anti-PD-1 antibody is PDR001.

Formulations, Pharmaceutical Compositions, and Dosages

Some embodiments of the present invention are directed to a pharmaceutical composition comprising (i) from about 5 mM to about 50 mM of a buffering agent; (ii) from about 50 mM to about 300 mM of a stabilizing agent or bulking agent; and (iii) from about 0.001% to about 1% (w/v) of a surfactant. Other embodiments of the present invention are directed to a pharmaceutical composition comprising (i) from about 5 mM to about 50 mM of a buffering agent; (ii) from about 50 mM to about 300 mM of a stabilizing agent; (iii) from about 5 μM to about 1 mM of a chelating agent; and (iv) from about 0.001% to about 1% (w/v) of a surfactant. In some embodiments, such compositions are for use in antibody formulation.

In some embodiments of these compositions, the buffering agent is histidine, Tris-Cl, citrate (e.g., sodium citrate), Tris-citrate, phosphate (e.g., sodium phosphate), or any combination thereof. In some embodiments, the composition contains about 10 mM or about 20 mM of the buffering agent. In other embodiments, the stabilizing agent is sucrose, trehalose, raffinose, arginine, or any combination thereof. In other embodiments, the bulking agent is sodium chloride, mannitol, glycine, alanine, or any combination thereof. In other embodiments, the composition comprises about 150 mM or about 250 mM of the stabilizing agent or bulking agent. In other embodiments, the surfactant is polysorbate 80 (PS80), polysorbate 20 (PS20), poloxamer 188 (PX188), or any combination thereof. In other embodiments, the composition comprises about 0.05% to about 1% of the surfactant. In other embodiments, the composition further comprises from about 5 μM to about 1 mM of a chelating agent. In other embodiments, the chelating agent is diethylenetriaminepentaacetic acid (DTPA), ethylenediaminetetraacetic acid (EDTA), nitrilotriacetic acid, or any combination thereof. In other embodiments, the composition comprises about 20 μM of the chelating agent.

In other embodiments, the composition comprises (i) from about 5 mM to about 50 mM of citrate; (ii) from about 50 mM to about 300 mM of sodium chloride; and (iii) from about 0.001% to about 1% (w/v) of polysorbate or poloxamer. In other embodiments, the composition comprises (i) about 10 mM of citrate and about 10 mM of phosphate; (ii) about 150 mM of sodium chloride; and (iii) about 0.05% (w/v) of polysorbate 80. In other embodiments, the composition comprises (i) about 10 mM of sodium citrate and about 10 mM of sodium phosphate; (ii) about 150 mM of sodium chloride; and (iii) about 0.05% (w/v) of polysorbate 80. In other embodiments, the composition comprises (i) about 20 mM of histidine; (ii) about 250 mM of sucrose; and (iii) about 0.05% (w/v) of polysorbate 80. In other embodiments, the composition comprises (i) from about 5 mM to about 50 mM of histidine; (ii) from about 50 mM to about 300 mM of sucrose; (iii) from about 5 μM to about 1 mM of one or more chelating agents; and (iv) from about 0.001% to about 1% (w/v) of polysorbate or poloxamer. In other embodiments, the composition comprises (i) about 20 mM of histidine; (ii) about 250 mM of sucrose; (iii) about 20 μM to about 50 μM of DTPA or EDTA; and (iv) about 0.05% (w/v) of polysorbate 80. In other embodiments, the composition comprises (i) 10 mM of citrate and 10 mM phosphate; (ii) 150 mM of sodium chloride; and (iii) 0.05% (w/v) of polysorbate 80. In other embodiments, the composition comprises (i) 10 mM of sodium citrate and 10 mM sodium phosphate; (ii) 150 mM of sodium chloride; and (iii) 0.05% (w/v) of polysorbate 80. In other embodiments, the composition comprises (i) 20 mM of histidine; (ii) 250 mM of sucrose; and (iii) 0.05% (w/v) of polysorbate 80. In other embodiments, the composition comprises (i) 20 mM of histidine; (ii) 250 mM of sucrose; (iii) from 20 μM to 50 μM of DTPA or EDTA; and (iv) 0.05% (w/v) of polysorbate 80. In other embodiments, the composition further comprises an antibody or antigen binding fragment thereof.

Other formulations of the present invention comprise an anti-LAG-3 antibody or antigen binding fragment thereof, or an anti-LAG-3 antibody or antigen binding fragment thereof and an anti-PD-1 antibody, anti-PD-L1 antibody, or antigen binding fragment thereof. In some formulations of the present invention, an anti-LAG-3 antibody or antigen binding fragment thereof is formulated in a single composition, e.g., a pharmaceutical composition containing the anti-LAG-3 antibody or antigen binding fragment thereof and a pharmaceutically acceptable carrier. In other formulations of the present invention, an anti-LAG-3 antibody is formulated with an anti-PD-1 antibody, anti-PD-L1 antibody, or antigen binding fragment thereof in a single composition, e.g., a pharmaceutical composition containing the anti-LAG-3 antibody, the anti-PD1 antibody, or antigen binding fragment thereof, and a pharmaceutically acceptable carrier. An anti-PD-L1 antibody or antigen binding fragment thereof can be used in place of an anti-PD-1 antibody or antigen binding fragment thereof in any formulation, composition, or method described herein.

As used herein, a "pharmaceutically acceptable carrier" includes any and all solvents, dispersion media, coatings, antibacterial and antifungal agents, isotonic and absorption delaying agents, and the like that are physiologically compatible. In certain embodiments, the carrier for a composition containing an antibody is suitable for intravenous, intramuscular, subcutaneous, parenteral, spinal or epidermal administration (e.g., by injection or infusion). A pharmaceutical composition of the invention can include one or more pharmaceutically acceptable salts, anti-oxidant, aqueous and non-aqueous carriers, and/or adjuvants such as preservatives, wetting agents, emulsifying agents and dispersing agents.

In one embodiment, the composition comprising the anti-LAG-3 antibody or antigen binding fragment thereof, or a combination of an anti-LAG-3 antibody or antigen binding fragment thereof and an anti-PD-1 antibody, or anti-PD-L1 antibody, or antigen binding fragments thereof is provided in a single-use vial. In another embodiment, the composition comprising the anti-LAG-3 antibody or antigen binding fragment thereof, or a combination of an anti-LAG-3 antibody or antigen binding fragment thereof and an anti-PD-1 antibody, or anti-PD-L1 antibody, or antigen binding fragment thereof is provided in a multi-use vial.

In some embodiments, the combination of an anti-LAG-3 antibody or antigen binding fragment thereof and an anti-PD-1 antibody, or anti-PD-L1 antibody, or antigen binding fragments thereof is present in the composition at a fixed dose (i.e., a fixed ratio). In other embodiments, the fixed dose is between at least about 1:200 to at least about 200:1, at least about 1:150 to at least about 150:1, at least about 1:100 to at least about 100:1, at least about 1:75 to at least about 75:1, at least about 1:50 to at least about 50:1, at least about 1:25 to at least about 25:1, at least about 1:10 to at least about 10:1, at least about 1:5 to at least about 5:1, at least about 1:4 to at least about 4:1, at least about 1:3 to at least about 3:1, at least about 1:2 to at least about 2:1 mg anti-LAG-3 antibody or antigen binding fragment thereof to mg anti-PD-1 antibody, anti-PD-L1 antibody, or antigen binding fragment thereof. In some embodiments, the fixed dose is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, or about 1:200 anti-LAG-3 antibody or antigen binding fragment thereof to anti-PD-1 antibody, anti-PD-L1 antibody, or antigen binding fragment thereof. In some embodiments, the fixed dose is at least about 1:1, about 2:1, about 3:2, about 3:1, about 4:1, about 5:1, about 6:1, about 7:1, about 8:1, about 9:1, about 10:1, about 15:1, about 20:1, about 30:1, about 40:1, about 50:1, about 60:1, about 70:1, about 80:1, about 80:3, about 90:1, about 100:1, about 120:1, about 140:1, about 160:1, about 180:1, or about 200:1 mg anti-LAG-3 antibody or antigen binding fragment thereof to mg anti-PD-1 antibody, anti-PD-L1 antibody, or antigen binding fragment thereof.

Combinations of an anti-LAG-3 antibody or antigen binding fragment thereof and an anti-PD-1 antibody, anti-PD-L1 antibody, or antigen binding fragment thereof are also described in, for example, Int'l Pub. No. WO2016/1686716, the contents of which are incorporated by reference herein.

In other embodiments, the composition comprises an anti-LAG-3 antibody or antigen binding fragment thereof, and an anti-PD-1 antibody, anti-PD-L1 antibody, or antigen binding fragment thereof at a ratio (e.g., from 200:1 to 1:200, 100:1 to 1:100, 20-1:1 to 1:1-20, or any ratio disclosed herein), wherein the composition has one or more characteristics selected from the group consisting of: (i) the aggregation in the composition is comparable to the aggregation in a reference composition (i.e., a composition comprising either the anti-PD-1 antibody, anti-PD-L1 antibody, or antigen binding fragment thereof, or the anti-LAG-3 antibody or antigen binding fragment thereof) after 6-months storage at 2° C. to 8° C.; (ii) the fragmentation in the composition is comparable to the aggregation in a reference composition (i.e., a composition comprising either the anti-PD-1 antibody, anti-PD-L1 antibody, or antigen binding fragment thereof, or the anti-LAG-3 antibody or antigen binding fragment thereof) after 6-months storage at 2° C. to 8° C.; (iii) the deamidation of the anti-PD-1 antibody, anti-PD-L1 antibody, or antigen binding fragment thereof, or the anti-LAG-3 antibody or antigen binding fragment thereof in the composition is comparable to the deamidation of the antibody in a reference composition (i.e., a composition comprising either the anti-PD-1 antibody, anti-PD-L1 antibody, or antigen binding fragment thereof or the anti-LAG-3 antibody or antigen binding fragment thereof) after 6-months storage at 2° C. to 8° C.; (iv) the level of particulate matter in the composition is comparable to the level of particulate matter in a reference composition (i.e., a composition comprising either the anti-PD-1 antibody, anti-PD-L1 antibody, or antigen binding fragment thereof or the anti-LAG-3 antibody or antigen binding fragment thereof) after 6-months storage at 2° C. to 8° C.; and (v) any combination thereof. In other embodiments, a composition of the invention that comprises an anti-LAG-3 antibody or antigen binding fragment thereof has one or more of the same characteristics.

In yet other embodiments, the composition comprises an anti-LAG-3 antibody or antigen binding fragment thereof, and an anti-PD-1 antibody, anti-PD-L1 antibody, or antigen binding fragment thereof at a ratio (e.g., from 200:1 to 1:200, 100:1 to 1:100, 20-1:1 to 1:1-20, or any ratio disclosed herein, wherein the composition has one or more characteristics selected from the group consisting of: (i) the aggregation in the composition is comparable to the aggregation in a reference composition (i.e., a composition comprising either the anti-PD-1 antibody, anti-PD-L1 antibody, or antigen binding fragment thereof, or the anti-LAG-3 antibody or antigen binding fragment thereof) after 6-months storage at 25° C.; (ii) the fragmentation in the composition is comparable to the aggregation in a reference composition (i.e., a composition comprising the anti-PD-1 antibody, anti-PD-L1 antibody, or antigen binding fragment thereof, or the anti-LAG-3 antibody or antigen binding fragment thereof) after 6-months storage at 25° C.; (iii) the deamidation of the anti-PD-1 antibody, anti-PD-L1 antibody, or antigen binding fragment thereof, or the anti-LAG-3 antibody or antigen binding fragment thereof in the composition is comparable to the deamidation of the antibody in a reference composition (i.e., a composition comprising either the anti-PD-1 antibody, anti-PD-L1 antibody, or antigen binding fragment thereof, or the anti-LAG-3 antibody or antigen binding fragment thereof) after 6-months storage at 25° C.; (iv) the level of particulate matter in the composition is comparable to the level of particular matter in a reference composition (i.e., a composition comprising either the anti-PD-1 antibody, anti-PD-L1 antibody, or antigen binding fragment thereof, or the anti-LAG-3 antibody or antigen binding fragment thereof) after 6-months storage at 25° C.; and (v) any combination thereof. In other embodiments, a composition of the invention that comprises an anti-LAG-3 antibody or antigen binding fragment thereof has one or more of the same characteristics.

In some embodiments, the aggregation of a composition of the invention is measured by a level of high molecular weight (HMW) species in the composition, which can be detected by size exclusion high-performance liquid chromatography (SE-HPLC). In some embodiments, the fragmentation of a composition of the invention is measured by a level of low molecular weight (LMW) species in the composition, which is detected by SE-HPLC. In some embodiments, the deamidation of a composition of the invention is measured by a level of acidic charge variants in the composition, which is detected by cation exchange chromatography (CEX) or imaged capillary isoelectric focusing (iCIEF).

In some embodiments, the amount of the anti-LAG-3 antibody or antigen binding fragment thereof in the composition is at least about 60 mg, about 80 mg, about 100 mg, about 120 mg, about 140 mg, about 160 mg, about 180 mg, about 200 mg, about 220 mg, about 240 mg, about 260 mg, about 280 mg, or about 300 mg. In some embodiments, the amount of the anti-LAG-3 antibody or antigen binding fragment thereof in the composition is from about 60 mg to about 300 mg, from about 60 mg to about 240 mg, from about 60 mg to about 160 mg, from about 60 mg to about 80 mg, from about 80 mg to about 300 mg, from about 80 mg to about 240 mg, from about 80 mg to about 160 mg, from about 160 mg to about 300 mg, or from about 160 mg to about 240 mg. In some embodiments, the amount of the anti-LAG-3 antibody or antigen binding fragment thereof in the composition is about 80 mg, about 160 mg, about 200 mg, or about 240 mg.

In some embodiments, the amount of the anti-LAG-3 antibody or antigen binding fragment thereof is at least about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 20 mg/ml, about 25 mg/ml, or about 30 mg/ml. In some embodiments, the amount of the anti-LAG-3 antibody or antigen binding fragment thereof is from about 1 mg/ml to about 30 mg/ml, from about 1 mg/ml to about 15 mg/ml, from about 2 mg/ml to about 15 mg/ml, from about 4 mg/ml to about 15 mg/ml, from about 10 mg/ml to about 15 mg/ml, from about 4 mg/ml to about 15 mg/ml, from about 4 mg/ml to about 12 mg/ml, from about 4 mg/ml to about 10 mg/ml, from about 4 mg/ml to about 8 mg/ml, from about 8 mg/ml to about 15 mg/ml, from about 8 mg/ml to about 12 mg/ml, or from about 8 mg/ml to about 10 mg/ml.

In some embodiments, the amount of the anti-LAG-3 antibody or antigen binding fragment thereof in the composition is a least about 0.5 mg/kg, at least about 1 mg/kg, at least about 2 mg/kg, at least about 3 mg/kg or at least about 5 mg/kg. In some embodiments, the amount of anti-LAG-3 antibody or antigen binding fragment thereof in the composition is between about 0.5 mg/kg and about 5 mg/kg, between about 0.5 mg/kg and about 5 mg/kg, between about 0.5 mg/kg and about 3 mg/kg or between about 0.5 mg/kg and about 2 mg/kg. In some embodiments, the amount of the anti-LAG-3 antibody or antigen binding fragment thereof in the composition is at least about 1 mg/kg.

In some embodiments, the amount of the anti-PD-1 antibody, or anti-PD-L1 antibody, or antigen binding fragments thereof in the composition is at least about 60 mg, about 80 mg, about 100 mg, about 120 mg, about 14 mg, about 160 mg, about 180 mg, about 200 mg, about 220 mg, about 240 mg, about 260 mg, about 280 mg, or about 300 mg. In some embodiments, the amount of the anti-PD-1 antibody, or anti-PD-L1 antibody, or antigen binding fragments thereof in the composition is at least about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg. In some embodiments, the amount of the anti-PD-1 antibody, or anti-PD-L1 antibody, or antigen binding fragments thereof in the composition is from about 60 mg to about 300 mg, from about 60 mg to about 240 mg, from about 80 mg to about 240 mg, from about 100 mg to about 240 mg, from about 160 mg to about 240 mg, from about 160 mg to about 300 mg, or from about 240 mg to about 300 mg. In some embodiments, the amount of the anti-PD-1 antibody, or anti-PD-L1 antibody, or antigen binding fragments thereof in the composition is about 80 mg, about 160 mg, or about 240 mg.

In some embodiments, the amount of the anti-PD-1 antibody, or anti-PD-L1 antibody, or antigen binding fragments thereof is at least about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 20 mg/ml, about 25 mg/ml, or about 30 mg/ml. In some embodiments, the amount of the anti-PD-1 antibody, or anti-PD-L1 antibody, or antigen binding fragments thereof is from about 1 mg/ml to about 30 mg/ml, from about 1 mg/ml to about 15 mg/ml, from about 2 mg/ml to about 15 mg/ml, from about 4 mg/ml to about 15 mg/ml, from about 4 mg/ml to about 12 mg/ml, from about 4 mg/ml to about 8 mg/ml, or from about 8 mg/ml to about 12 mg/ml.

In some embodiments, the amount of the anti-PD-1 antibody, or anti-PD-L1 antibody, or antigen binding fragments thereof in the composition is a least about 0.5 mg/kg, at least about 1 mg/kg, at least about 2 mg/kg, at least about 3 mg/kg or at least about 5 mg/kg. In some embodiments, the amount of anti-PD-1 antibody, or anti-PD-L1 antibody, or antigen binding fragments thereof in the composition is between about 0.5 mg/kg and about 5 mg/kg, between about 0.5 mg/kg and about 5 mg/kg, between about 0.5 mg/kg and about 3 mg/kg or between about 0.5 mg/kg and about 2 mg/kg. In some embodiments, the amount of the anti-PD-1 antibody, or anti-PD-L1 antibody, or antigen binding fragments thereof in the composition is at least about 1 mg/kg.

In some embodiments, the anti-LAG-3 antibody or antigen binding fragment thereof and the anti-PD-1 antibody, or anti-PD-L1 antibody, or antigen binding fragments thereof are combined using the current formulations of the two antibodies (for example, 2 ml of an anti-PD-1 antibody, or anti-PD-L1 antibody, or antigen binding fragments thereof in a citrate-based buffer are combined with 2 ml of an anti-LAG-3 antibody or antigen binding fragment thereof in a histidine-based buffer with no buffer exchange).

In some embodiments, the compositions of the invention contain a buffering agent. In some embodiments, the buffering agent is citrate (e.g., a citrate buffer, sodium citrate), a Tris buffer, a Tris-Cl buffer, histidine (e.g., a histidine buffer), phosphate (e.g., a phosphate buffer, sodium phosphate), a TAE buffer, a HEPES buffer, a TBE buffer, a sodium phosphate buffer, a MES buffer, an ammonium sulfate buffer, a potassium phosphate buffer, a potassium thiocyanate buffer, a succinate buffer, a tartrate buffer, a DIPSO buffer, a HEPPSO buffer, a POPSO buffer, a PIPES buffer, a PBS buffer, a MOPS buffer, an acetate buffer, a cacodylate buffer, a glycine buffer, a sulfate buffer, an imidazole buffer, a guanidine hydrochloride buffer, a phosphate-citrate buffer, a borate buffer, a malonate buffer, a 3-picoline buffer, a 2-picoline buffer, a 4-picoline buffer, a 3,5-lutidine buffer, a 3,4-lutidine buffer, a 2,4-lutidine buffer, a Aces, a diethylmalonate buffer, a N-methylimidazole buffer, a 1,2-dimethylimidazole buffer, a TAPS buffer, a bis-Tris buffer, a L-arginine buffer, a lactate buffer, a glycolate buffer, or any combination thereof.

In some embodiments, the anti-LAG-3 antibody or antigen binding fragment thereof and the PD-1 antibody, or anti-PD-L1 antibody, or antigen binding fragments thereof are formulated in a buffer that is based on the buffer conditions of one of the two individual antibody formulations. In some embodiments, the buffer conditions used are those of the anti-LAG-3 antibody or antigen binding fragment thereof. In other embodiments, the buffer conditions used are those of the anti-PD-1 antibody, or anti-PD-L1 antibody, or antigen binding fragments thereof.

In some embodiments, the anti-LAG-3 antibody or antigen binding fragment thereof and the PD-1 antibody, or anti-PD-L1 antibody, or antigen binding fragments thereof are formulated in buffer conditions that are different from the buffer conditions of either of the two antibodies on its own.

In some embodiments, the buffer used is a Tris-based buffer. In some embodiments, the Tris buffer is a Tris-Cl buffer. In some embodiments, the concentration of Tris-Cl in the buffer is at least about 5 mM, about 10 mM, about 15 mM, about 20 mM, about 25 mM, about 30 mM, about 35 mM, about 40 mM, or about 50 mM. In some embodiments, the concentration of Tris-Cl is from about 5 mM to about 50 mM, from about 10 mM to about 50 mM, from about 10 mM to about 40 mM, from about 10 mM to about 30 mM, or from about 15 mM to about 25 mM. In some embodiments, the concentration of Tris-Cl is about 20 mM.

In some embodiments, the buffer used is a histidine-based buffer. In some embodiments, the concentration of histidine is at least about 5 mM, about 10 mM, about 15 mM, about 20 mM, about 25 mM, about 30 mM, about 35 mM, about 40 mM, or about 50 mM. In some embodiments, the concentration of histidine is from about 5 mM to about 50 mM, from about 5 mM to about 40 mM, from about 5 mM to about 30 mM, from about 5 mM to about 25 mM, or from about 10 mM to about 15 mM. In some embodiments, the concentration of histidine is about 20 mM.

In some embodiments, the buffer used is a Tris-citrate buffer. In some embodiments, the concentration of Tris-Cl is at least about 5 mM, about 10 mM, about 15 mM, about 20 mM, about 25 mM, about 30 mM, about 35 mM, about 40 mM, or about 50 mM and the concentration of citrate is at least about 2 mM, about 5 mM, about 10 mM, about 15 mM, about 20 mM, about 25 mM, about 30 mM, about 35 mM, about 40 mM, or about 50 mM. In some embodiments, the concentration of Tris-Cl is from about 5 mM to about 20 mM, from about 5 mM to about 15 mM, or from about 10 mM to about 15 mM and the concentration of citrate is from about 1 mM to about 15 mM, from about 1 mM to about 10 mM, or from about 5 mM to about 10 mM. In some embodiments, the concentration of Tris-Cl is about 13.3 mM and the concentration of citrate is about 6.7 mM.

In some embodiments, the pH of the composition is at least about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In some embodiments, the pH of the composition is from about 4.5 to about 8.0, from about 5.0 to about 8.0, from about 5.0 to about 7.0, from about 5.0 to about 6.5, from about 5.3 to about 6.3, from about 5.0 to about 6.0, from about 5.5 to about 6.0, or from about 5.5 to about 6.5. In some embodiments, the pH is about 6.5, about 6.4, about 6.3, about 6.2, about 6.1, about 6.0, about 5.5, about 5.4, about 5.3, about 5.2, about 5.1, or about 5.0. In some embodiments, the pH is determined using a pH meter.

In some embodiments, the composition of the invention further comprises a bulking agent. In some embodiments, the bulking agent can be selected from the group consisting of NaCl, mannitol, glycine, alanine, and any combination thereof. In some embodiments, the bulking agent is present in the composition in an amount of from about 50 mM to about 300 mM, from about 50 mM to about 200 mM, from about 50 mM to about 150 mM, from about 100 mM to about 200 mM, or from about 150 mM to about 200 mM. In some embodiments, the bulking agent is sodium chloride present in an amount from about 50 mM to about 300 mM, or about 150 mM.

In other embodiments, the composition of the invention comprises a stabilizing agent. In some embodiments, the stabilizing agent can be selected from the group consisting of sucrose, trehalose, raffinose, arginine, and any combination thereof. In some embodiments, the stabilizing agent is present in the composition in an amount of from about 50 mM to about 300 mM, from about 50 mM to about 250 mM, from about 100 mM to about 250 mM, from about 150 mM to about 250 mM, or from about 200 mM to about 250 mM. In some embodiments, the stabilizing agent is sucrose present in an amount from about 50 mM to about 300 mM, or about 250 mM.

In other embodiments, the composition of the invention comprises a surfactant. In some embodiments, the surfactant is polysorbate, poloxamer, or any combination thereof. In other embodiments, the surfactant can be selected from the group consisting of polysorbate 80 (PS80), polysorbate 20 (PS20), poloxamer 188 (PX188), and any combination thereof. In some embodiments, the surfactant is present in the composition in an amount of from about 0.001% to about 1% (w/v), from about 0.01% to about 1% (w/v), from about 0.01% to about 0.5% (w/v), from about 0.05% to about 1% (w/v), or from about 0.05% to about 0.5% (w/v). In some embodiments, the surfactant is PS80 or PS20 present in an amount of from about 0.001% to about 1% (w/v), or about 0.05% (w/v). In other embodiments, the surfactant is poloxamer (e.g., PX188) present in an amount of from about 0.001% to about 1% (w/v) or an amount of about 0.5% (w/v) or about 1% (w/v).

In some embodiments, the composition comprises polysorbate 80, NF (PS80) (% w/v) at a concentration of at least about 0.005%, at least about 0.01%, at least about 0.015%, at least about 0.02%, at least about 0.03%, at least about 0.04%, at least about 0.05%, at least about 0.06%, at least about 0.07%, at least about 0.08%, at least about 0.09%, or at least about 0.1%. In other embodiments, the composition comprises from about 0.005% to about 0.1% PS80, from about 0.005% to about 0.02% PS80, from about 0.005% to about 0.05% PS80, from about 0.01% to about 0.02% PS80, from about 0.02% to about 0.1% PS80, or from about 0.01% to about 0.03% PS80. In a particular embodiment, the composition comprises PS80 at a concentration of about 0.05%.

In other embodiments, the composition of the invention comprises a chelating agent. In some embodiments, the chelating agent can be selected from the group consisting of diethylenetriaminepentaacetic acid (DTPA), ethylenediaminetetraacetic acid (EDTA), nitrilotriacetic acid, and any combination thereof. In some embodiments, the chelating agent is present in the composition in an amount of from about 5 µM to about 1 mM, from about 5 µM to about 50 µM, from about 10 µM to about 50 µM, or from about 20 µM to about 50 µM. In some embodiments, the chelating agent is DTPA or EDTA present in an amount of from about 5 µM to about 1 mM, from about 20 µM to about 50 µM, about 20 µM, or about 50 µM.

In other embodiments, the composition comprises diethylenetriaminepentaacetic acid (DTPA), USP at a concentration of at least about 5 µM, at least about 10 µM, at least about 15 µM, at least about 20 µM, at least about 25 µM, at least about 30 µM, at least about 40 µM, at least about 50 µM, at least about 60 µM, at least about 70 µM, at least about 75 µM, at least about 80 µM, at least about 90 µM, at least about 100 µM, at least about 110 µM, at least about 120 µM, at least about 130 µM, at least about 140 µM, at least about 150 at least about 175 or at least about 200 µM. In some embodiments, the composition comprises from about 10 µM to about 200 µM DTPA, from about 10 µM to about 150 µM DTPA, from about 10 µM to about 100 µM DTPA, from about 10 µM to about 30 µM DTPA, from about 50 µM to about 100 µM DTPA, or from about 75 µM to about 125 µM DTPA. In certain embodiments, the composition comprises DTPA or EDTA at about 20 µM.

In other embodiments, the composition comprises a third antibody. In some embodiments, the third antibody is any antibody disclosed herein.

Some embodiments of the invention are directed to compositions comprising an anti-LAG-3 antibody or antigen binding fragment thereof, a buffering agent, a stabilizing agent or a bulking agent, and a surfactant. In some embodiments, the composition comprises (i) from about 1 mg/ml to about 100 mg/ml of an anti-LAG-3 antibody or antigen binding fragment thereof; (ii) from about 5 mM to about 50 mM of a buffering agent; (iii) from about 50 mM to about 300 mM of a stabilizing agent; and (iv) from about 0.001% to about 1% (w/v) of a surfactant. In other embodiments, the composition comprises (i) from about 1 mg/ml to about 100 mg/ml of an anti-LAG-3 antibody or antigen binding fragment thereof; (ii) from about 5 mM to about 50 mM of citrate; (iii) from about 50 mM to about 300 mM of sodium chloride; and (iv) from about 0.001% to about 1% (w/v) of polysorbate or poloxamer. In other embodiments, the composition comprises (i) about 11 mg/ml of an anti-LAG-3 antibody or antigen binding fragment thereof; (ii) about 10 mM of citrate and about 10 mM phosphate; (iii) about 150 mM of sodium chloride; and (iv) about 0.05% (w/v) of polysorbate 80. In other embodiments, the composition comprises (i) about 11 mg/ml of an anti-LAG-3 antibody or antigen binding fragment thereof; (ii) about 10 mM of sodium citrate and about 10 mM sodium phosphate; (iii) about 150 mM of sodium chloride; and (iv) about 0.05% (w/v) of polysorbate 80. In other embodiments, the composition comprises (i) from about 1 mg/ml to about 100 mg/ml of an anti-LAG-3 antibody or antigen binding fragment thereof; (ii) from about 5 mM to about 50 mM of histidine; (iii) from about 50 mM to about 300 mM of sucrose; and (iv) from about 0.001% to about 1% (w/v) of polysorbate or poloxamer. In other embodiments, the composition comprises (i) about 10 mg/ml of an anti-LAG-3 antibody or antigen binding fragment thereof; (ii) about 20 mM of histidine; (iii) about 250 mM of sucrose; and (iv) about 0.05% (w/v) of polysorbate 80. In other embodiments, the composition comprises (i) from about 1 mg/ml to about 100 mg/ml of an anti-LAG-3 antibody or antigen binding fragment thereof; (ii) from about 5 mM to about 50 mM of histidine; (iii) from about 50 mM to about 300 mM of sucrose; (iv) from about 5 µM to about 1 mM of one or more chelating agents; and (v) from about 0.001% to about 1% (w/v) of polysorbate or poloxamer.

In other embodiments, the composition comprises (i) about 10 mg/ml of an anti-LAG-3 antibody or antigen binding fragment thereof; (ii) about 20 mM of histidine; (iii) about 250 mM of sucrose; (iv) about 20 µM to about 50 µM of DTPA or EDTA; and (v) about 0.05% (w/v) of polysorbate 80. In other embodiments, the composition comprises (i) 11 mg/ml of an anti-LAG-3 antibody or antigen binding fragment thereof; (ii) 10 mM of citrate and 10 mM phosphate; (iii) 150 mM of sodium chloride; and (iv) 0.05% (w/v) of polysorbate 80. In other embodiments, the composition comprises (i) 11 mg/ml of an anti-LAG-3 antibody or antigen binding fragment thereof; (ii) 10 mM of sodium citrate and 10 mM sodium phosphate; (iii) 150 mM of sodium chloride; and (iv) 0.05% (w/v) of polysorbate 80. In other embodiments, the composition comprises (i) 110 mg of an anti-LAG-3 antibody or antigen binding fragment thereof; (ii) 10 mM of citrate; (iii) 150 mM of sodium chloride; and (iv) 0.05% (w/v) of polysorbate 80. In other embodiments, the composition comprises (i) 10 mg/ml of an anti-LAG-3 antibody or antigen binding fragment thereof; (ii) 20 mM of histidine; (iii) 250 mM of sucrose; and (iv) 0.05% (w/v) of polysorbate 80. In other embodiments, the composition comprises (i) 100 mg of an anti-LAG-3 antibody or antigen binding fragment thereof; (ii) 20 mM of histidine; (iii) 250 mM of sucrose; and (iv) 0.05% (w/v) of polysorbate 80. In other embodiments, the composition comprises (i) 10 mg/ml of an anti-LAG-3 antibody or antigen binding fragment thereof; (ii) 20 mM of histidine; (iii) 250 mM of sucrose; (iv) from 20 µM to 50 µM of DTPA or EDTA; and (v) 0.05% (w/v) of polysorbate 80. In other embodiments, the composition comprises (i) 100 mg of an anti-LAG-3 antibody or antigen binding fragment thereof; (ii) 20 mM of histidine; (iii) 250 mM of sucrose; (iv) from 20 µM to 50 µM of DTPA or EDTA; and (v) 0.05% (w/v) of polysorbate 80. In other embodiments, the composition comprises (i) 50 mg/ml of an anti-LAG-3 antibody or antigen binding fragment thereof, (ii) 20 mM of histidine, (iii) 250 mM of sucrose, and (iv) 0.05% (w/v) PS80, and has a pH of 5.5.

In still other embodiments, compositions of the invention comprise an anti-LAG-3 antibody or antigen binding fragment thereof, an anti-PD-1 antibody, or anti-PD-L1 antibody, or antigen binding fragments thereof, a buffering agent, a stabilizing agent, and a surfactant. In some embodiments, the composition comprises (i) from about 1 mg/ml to about 100 mg/ml of an anti-LAG-3 antibody or antigen binding fragment thereof; (ii) from about 1 mg/ml to about 100 mg/ml of an anti-PD-1 antibody, or anti-PD-L1 antibody, or antigen binding fragments thereof; (iii) from about 5 mM to about 50 mM of a buffering agent; (iv) from about 50 mM to about 300 mM of a stabilizing agent; (v) from about 5 µM to about 1 mM of a chelating agent; and (vi) from about 0.001% to about 1% (w/v) of a surfactant. In some embodiments, the composition comprises (i) from about 1 mg/ml to about 100 mg/ml of an anti-LAG-3 antibody or antigen binding fragment thereof; (ii) from about 1 mg/ml to about 100 mg/ml of an anti-PD-1 antibody, or anti-PD-L1 antibody, or antigen binding fragments thereof; (iii) from about 5 mM to about 50 mM of histidine; (iv) from about 50 mM to about 300 mM of sucrose; (v) from about 5 µM to about 1 mM of DTPA or EDTA; and (vi) from about 0.001% to about 1% (w/v) of polysorbate or poloxamer. In other embodiments, the composition comprises (i) from about 80 mg to about 240 mg of an anti-LAG-3 antibody or antigen binding fragment thereof; (ii) from about 60 mg to about 300 mg of an anti-PD-1 antibody, or anti-PD-L1 antibody, or antigen binding fragments thereof; (iii) from about 5 mM to about 50 mM of histidine; (iv) from about 50 mM to about 300 mM of sucrose; (v) from about 5 µM to about 1 mM of DTPA or EDTA; and (vi) from about 0.001% to about 1% (w/v) of polysorbate or poloxamer.

In other embodiments, the composition comprises (i) about 4 mg/ml, about 8 mg/ml, about 10 mg/ml, or about 12 mg/ml of an anti-LAG-3 antibody or antigen binding fragment thereof; (ii) about 12 mg/ml of an anti-PD-1 antibody, or anti-PD-L1 antibody, or antigen binding fragments thereof; (iii) about 20 mM of histidine; (iv) about 250 mM of sucrose; (v) from about 20 µM to about 50 µM of DTPA or EDTA; and (vi) about 0.05% (w/v) of polysorbate 80. In other embodiments, the composition comprises (i) about 80 mg, about 160 mg, about 200 mg, or about 240 mg of an anti-LAG-3 antibody or antigen binding fragment thereof; (ii) about 240 mg of an anti-PD-1 antibody, or anti-PD-L1 antibody, or antigen binding fragments thereof; (iii) about 20 mM of histidine; (iv) about 250 mM of sucrose; (v) from about 20 µM to about 50 µM of DTPA or EDTA; and (vi) about 0.05% (w/v) of polysorbate 80. In other embodiments, the composition comprises (i) 4 mg/ml, 8 mg/ml, 10 mg/ml, or 12 mg/ml of an anti-LAG-3 antibody or antigen binding fragment thereof; (ii) 12 mg/ml of an anti-PD-1 antibody, or anti-PD-L1 antibody, or antigen binding fragments thereof; (iii) 20 mM of histidine; (iv) 250 mM of sucrose; (v) from 20 µM to 50 µM of DTPA or EDTA; and (vi) 0.05% (w/v) of polysorbate 80. In other embodiments, the composition comprises (i) 80 mg, 160 mg, 200 mg, or 240 mg of an anti-LAG-3 antibody or antigen binding fragment thereof; (ii) 240 mg of an anti-PD-1 antibody, anti-PD-L1 antibody, or antigen binding fragment thereof; (iii) 20 mM of histidine; (iv) 250 mM of sucrose; (v) from 20 µM to 50 µM of DTPA or EDTA; and (vi) 0.05% (w/v) of polysorbate 80. In other embodiments, the composition comprises (i) 80 mg of an anti-LAG-3 antibody or antigen binding fragment thereof, (ii) 240 mg of an anti-PD-1 antibody (e.g., nivolumab), or anti-PD-L1 antibody, or antigen binding fragments thereof, (iii) 20 mM histidine, (iv) 250 mM sucrose, (v) 50 µM of EDTA, and (vi) 0.05% (w/v) PS80, and has a pH of 5.8. In other embodiments, the composition comprises (i) 4 mg/ml of an anti-LAG-3 antibody or antigen binding fragment thereof, (ii) 12 mg/ml of an anti-PD-1 antibody (e.g., nivolumab), or anti-PD-L1 antibody, or antigen binding fragment thereof, (iii) 20 mM histidine, (iv) 250 mM sucrose, (v) 50 µM of EDTA, and (vi) 0.05% (w/v) PS80, and has a pH of 5.8.

In embodiments, the invention relates to a pharmaceutical composition comprising: (i) from about 1 mg/ml to about 100 mg/ml of an anti-LAG-3 antibody or antigen binding fragment thereof; (ii) from about 1 mg/ml to about 100 mg/ml of an anti-PD-1 antibody, or an anti-PD-L1 antibody, or antigen binding fragments thereof; (iii) from about 5 mM to about 50 mM of a buffering agent; (iv) from about 50 mM to about 300 mM of a stabilizing agent; (v) from about 5 µM to about 1 mM of a chelating agent; and (vi) from about 0.001% to about 1% (w/v) of a surfactant, wherein the composition is present in a vial at a fill volume of about 10 ml, about 15 ml, or about 20 ml. In some embodiments, the fill volume is about 20 ml. In certain embodiments, the anti-LAG-3 antibody or antigen binding fragment thereof comprises heavy and light chains comprising the sequences set forth in SEQ ID NOs:1 and 2, respectively. In one embodiment, the pharmaceutical composition comprises from about 60 mg to about 300 mg of the anti-PD-1 antibody, anti-PD-L1 antibody, or antigen binding fragment thereof. In an embodiment, the anti-PD-1 antibody, anti-PD-L1 antibody, or antigen binding fragment thereof of the pharmaceutical composition comprises CDR1, CDR2, and CDR3 domains of the heavy chain variable region having the sequence set forth in SEQ ID NO:19, and CDR1, CDR2, and CDR3 domains of the light chain variable region having the sequence set forth in SEQ ID NO:21. In certain embodiments, the anti-PD-1 antibody, anti-PD-L1 antibody, or antigen binding fragment thereof comprises (a) a heavy chain variable region CDR1 comprising the sequence set forth in SEQ ID NO:23; (b) a heavy chain variable region CDR2 comprising the sequence set forth in SEQ ID NO:24; (c) a heavy chain variable region CDR3 comprising the sequence set forth in SEQ ID NO:25; (d) a light chain variable region CDR1 comprising the sequence set forth in SEQ ID NO:26; (e) a light chain variable region CDR2 comprising the sequence set forth in SEQ ID NO:27; and (f) a light chain variable region CDR3 comprising the sequence set forth in SEQ ID NO:28. In an embodiment, the anti-PD-1 antibody, anti-PD-L1 antibody, or antigen binding fragment thereof comprises heavy and light chain variable regions comprising the sequences set forth in SEQ ID NOs:19 and 21, respectively. In a particular embodiment, the anti-PD-1 antibody, anti-PD-L1 antibody, or antigen binding fragment thereof comprises heavy and light chains comprising the sequences as set forth in SEQ ID NOs:17 and 18, respectively. In one embodiment, the anti-PD-1 antibody is pembrolizumab (KEYTRUDA; MK-3475), pidilizumab (CT-011), or nivolumab (OPDIVO; BMS-936558). In embodiments, the anti-PD-L1 antibody is atezolizumab (TECENTRIQ; RG7446), durvalumab (IMFINZI; MEDI4736), or BMS-936559. In some embodiments, the anti-LAG-3 antibody is BMS-986016 and the anti-PD-1 antibody is nivolumab, the anti-LAG-3 antibody is MK-4280 and the anti-PD-1 antibody is pembrolizumab, the anti-LAG-3 antibody is REGN3767 and the anti-PD-1 antibody is REGN2810, the anti-LAG-3 antibody is LAG525 and the anti-PD-1 is REGN2810, or the anti-LAG-3 antibody is LAG525 and the anti-PD-1 antibody is PDR001. In one embodiment, the ratio of the amount of the anti-LAG-3 antibody or antigen binding fragment thereof to the anti-PD-1 antibody, anti-PD-L1 antibody, or antigen binding fragment thereof to the amount of is about 1:3, about 1:2, about 1:1, or about 2:3.

Stability of the Compositions

In one embodiment, a composition disclosed herein is stable at about −60° C., 0° C., about 5° C., about 10° C., about 15° C., about 20° C., about 25° C., about 30° C., about 35° C., about 40° C., about 45° C., about 50° C., or about 55° C. for at least about 1 week, at least about 2 weeks, at least about 1 month, at least about 2 months, at least about 3 months, at least about 6 months, at least about 9 months, at least about 1 year, at least about 2 years, at least about 3 years, at least about 4 years, or at least about 5 years.

In another embodiment, the composition exhibits a change of the acidic peak (e.g., deamidation) that is less than about 15%, about 14%, about 13%, about 12%, about 11%, about 10%, about 9%, about 8%, about 7%, about 6%, about 5%, about 4%, about 3%, about 2%, or about 1% after being stored for about 1 month, about 2 months, about 3 months, about 4 months, about 6 months, about 1 year, about 2 years, about 3 years, about 4 years, or about 5 years at about 5° C. In other embodiments, the composition exhibits a change of the acidic peak that is less than about 15%, about 14%, about 13%, about 12%, about 11%, about 10%, about 9%, about 8%, about 7%, about 6%, about 5%, about 4%, about 3%, about 2%, or about 1% after being stored for about 1 month, about 2 months, about 3 months, about 4 months, about 6 months, about 1 year, about 2 years, about 3 years, about 4 years, or about 5 years at about 25° C. In some embodiments, the composition exhibits a change of the acidic peak that is less than about 15%, about 14%, about 13%, about 12%, about 11%, about 10%, about 9%, about 8%, about 7%, about 6%, about 5%, about 4%, about 3%, about 2%, or about 1% after being stored for about 1 month, about 2 months, about 3 months, about 4 months, about 6 months, about 1 year, about 2 years, about 3 years, about 4 years, or about 5 years at about 40° C. In some embodiments, the acidic peak is measured using an Imaged Capillary Isoelectric Focusing assay (cIEF).

In some embodiments, the deamidation of a composition of the present invention is comparable to the deamidation of a reference composition (e.g., a composition comprising anti-LAG-3 antibody or anti-PD-1 antibody) if the composition exhibits a change of the acidic peak (e.g., deamidation) that is less than about 15%, about 14%, about 13%, about 12%, about 11%, about 10%, about 9%, about 8%, about 7%, about 6%, about 5%, about 4%, about 3%, about 2%, or about 1% compared to the acidic peak of the reference composition.

In certain embodiments, the composition exhibits a change of the high molecular weight (HMW) peak (e.g., aggregation) that is less than about 15%, about 14%, about 13%, about 12%, about 11%, about 10%, about 9%, about 8%, about 7%, about 6%, about 5%, about 4%, about 3%, about 2%, or about 1% after being stored for about 1 month, about 2 months, about 3 months, about 4 months, about 6 months, about 1 year, about 2 years, about 3 years, about 4 years, or about 5 years at about 5° C. In some embodiments, the composition exhibits a change of the HMW peak that is less than about 15%, about 14%, about 13%, about 12%, about 11%, about 10%, about 9%, about 8%, about 7%, about 6%, about 5%, about 4%, about 3%, about 2%, or about 1% after being stored for about 1 month, about 2 months, about 3 months, about 4 months, about 6 months, about 1 year, about 2 years, about 3 years, about 4 years, or about 5 years at about 25° C. In some embodiments, the composition exhibits a change of the HMW peak that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, about 1 year, about 2 years, about 3 years, about 4 years, or about 5 years at about 40° C. In some embodiments, the composition exhibits a change of the HMW peak that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, about 0.1%, or less than about 0.1%. In certain embodiments, the composition exhibits a HMW peak that is about 15%, about 14%, about 13%, about 12%, about 11%, about 10%, about 9%, about 8%, about 7%, about 6%, about 5%, about 4%, about 3%, about 2.5%, about 2%, about 1.5%, about 1%, about 0.9%, about 0.8%, about 0.7%, about 0.6%, about 0.5%, about 0.4%, about 0.3%, about 0.2% or about 0.1% after being stored for about 1 month, about 2 months, about 3 months, about 4 months, about 6 months, about 1 year, about 2 years, about 3 years, about 4 years, or about 5 years at about 5° C., at about 25° C., or at about 40° C. In some embodiments, the high molecular weight peak is measured using chromatography. In some embodiments, the chromatography is size exclusion chromatography.

In some embodiments, the aggregation (e.g., a level of HMW species) of a composition of the present invention is comparable to the aggregation of a reference composition (a composition comprising either anti-LAG-3 antibody or anti-PD-1 antibody), if the composition exhibits a change of the BMW species peak that is less than about 15%, about 14%, about 13%, about 12%, about 11%, about 10%, about 9%, about 8%, about 7%, about 6%, about 5%, about 4%, about 3%, about 2%, or about 1% compared to the BMW species peak of the reference composition.

In some embodiments, the composition exhibits a change of the main peak that is less than about 15%, about 14%, about 13%, about 12%, about 11%, about 10%, about 9%, about 8%, about 7%, about 6%, about 5%, about 4%, about 3%, about 2%, or about 1% after being stored for about 1 month, about 2 months, about 3 months, about 4 months, about 6 months, about 1 year, about 2 years, about 3 years, about 4 years, or about 5 years at about 5° C. In some embodiments, the composition exhibits a change of the main peak that is less than about 15%, about 14%, about 13%, about 12%, about 11%, about 10%, about 9%, about 8%, about 7%, about 6%, about 5%, about 4%, about 3%, about 2%, or about 1% after being stored for about 1 month, about 2 months, about 3 months, about 4 months, about 6 months, about 1 year, about 2 years, about 3 years, about 4 years, or about 5 years at about 25° C. In some embodiments, the composition exhibits a change of the main peak that is less than about 15%, about 14%, about 13%, about 12%, about 11%, about 10%, about 9%, about 8%, about 7%, about 6%, about 5%, about 4%, about 3%, about 2%, or about 1% after being stored for about 1 month, about 2 months, about 3 months, about 4 months, about 6 months, about 1 year, about 2 years, about 3 years, about 4 years, or about 5 years at about 40° C. In some embodiments, the composition exhibits a change of the main peak that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1%. In some embodiments, the main peak is measured using an Imaged Capillary Isoelectric Focusing assay (cIEF).

In some embodiments, the composition exhibits a change of the low molecular weight (LMW) peak (e.g., fragmentation) that is less than about 15%, about 14%, about 13%, about 12%, about 11%, about 10%, about 9%, about 8%, about 7%, about 6%, about 5%, about 4%, about 3%, about 2%, or about 1% after being stored for about 1 month, about 2 months, about 3 months, about 4 months, about 6 months, about 1 year, about 2 years, about 3 years, about 4 years, or about 5 years at about 5° C. In some embodiments, the composition exhibits a change of the LMW peak that is less than about 15%, about 14%, about 13%, about 12%, about 11%, about 10%, about 9%, about 8%, about 7%, about 6%, about 5%, about 4%, about 3%, about 2%, or about 1% after being stored for about 1 month, about 2 months, about 3 months, about 4 months, about 6 months, or about 1 year at about 25° C. In some embodiments, the composition exhibits a change of the LMW peak that is less than about 15%, about 14%, about 13%, about 12%, about 11%, about 10%, about 9%, about 8%, about 7%, about 6%, about 5%, about 4%, about 3%, about 2%, or about 1% after being stored for about 1 month, about 2 months, about 3 months, about 4 months, about 6 months, about 1 year, about 2 years, about 3 years, about 4 years, or about 5 years at about 40° C. In some embodiments, the composition exhibits a change of the LMW peak that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1%. In certain embodiments, the composition exhibits a LMW peak that is about 15%, about 14%, about 13%, about 12%, about 11%, about 10%, about 9%, about 8%, about 7%, about 6%, about 5%, about 4%, about 3%, about 2.5%, about 2%, about 1.5%, about 1%, about 0.9%, about 0.8%, about 0.7%, about 0.6%, about 0.5%, about 0.4%, about 0.3%, about 0.2%, or about 0.1% after being stored for about 1 month, about 2 months, about 3 months, about 4 months, about 6 months, about 1 year, about 2 years, about 3 years, about 4 years, or about 5 years at about 5° C., at about 25° C., or at about 40° C. In some embodiments, the low molecular weight peak is measured using chromatography. In some embodiments, the chromatography is size exclusion chromatography.

In some embodiments, the fragmentation (e.g., a level of LMW species) of a composition of the present invention is comparable to the fragmentation of a reference composition (e.g., a composition comprising either anti-LAG-3 antibody or anti-PD-1 antibody), if the composition comprising the first and second antibodies exhibits a change of the LMW species peak that is less than about 15%, about 14%, about 13%, about 12%, about 11%, about 10%, about 9%, about 8%, about 7%, about 6%, about 5%, about 4%, about 3%, about 2%, or about 1% compared to the LMW species peak of the reference composition.

Method of Making the Compositions Disclosed Herein

In one embodiment, the invention is directed to a method of making any composition disclosed herein. In another embodiment, the formulation comprising an anti-LAG-3 antibody drug product is mixed with a formulation comprising an anti-PD-1 antibody or anti-PD-L1 antibody drug product to obtain the desired ratio in a final drug product with no buffer changes. In some embodiments, a formulation comprising an anti-LAG-3 antibody drug substance and a formulation comprising an anti-PD-1 antibody drug substance are subject to buffer exchanges and/or concentration before being mixed to obtain the desired ratio in a final drug product.

In other embodiments, the composition is diluted prior to use. In certain embodiments, the composition is diluted with 0.9% Sodium Chloride Injection, USP or 5% Dextrose Injection, USP prior to use. In other embodiments, the composition is diluted to obtain an infusion with a desired total concentration of antibody. In yet other embodiments, the final total antibody concentration is from about 1 mg/ml to about 500 mg/ml, about 1 mg/ml to about 450 mg/ml, about 1 mg/ml to about 400 mg/ml, about 1 mg/ml to about 350 mg/ml, about 1 mg/ml to about 300 mg/ml, about 1 mg/ml to about 250 mg/ml, about 1 mg/ml to about 200 mg/ml, about 1 mg/ml to about 150 mg/ml, about 1 mg/ml to about 100 mg/ml, about 1 mg/ml to about 90 mg/ml, about 1 mg/ml to about 80 mg/ml, about 1 mg/ml to about 70 mg/ml, about 1 mg/ml to about 60 mg/ml, about 1 mg/ml to about 50 mg/ml, about 1 mg/ml to about 40 mg/ml, about 1 mg/ml to about 30 mg/ml, about 1 mg/ml to about 20 mg/ml, about 1 mg/ml to about 15 mg/ml, about 1 mg/ml to about 10 mg/ml, about 1 mg/ml to about 9 mg/ml, about 1 mg/ml to about 8 mg/ml, about 1 mg/ml to about 7 mg/ml, about 1 mg/ml to about 6 mg/ml, about 1 mg/ml to about 5 mg/ml, about 1 mg/ml to about 4 mg/ml, about 1 mg/ml to about 3 mg/ml, about 1 mg/ml to about 2 mg/ml, about 0.5 mg/ml to about 3 mg/ml, about 50 mg/ml to about 400 mg/ml, or about 100 mg/ml to about 300 mg/ml. In other embodiments, the final total antibody concentration is from about 1 mg/ml to about 30 mg/ml, from about 1 mg/ml to about 15 mg/ml, from about 2 mg/ml to about 15 mg/ml, from about 4 mg/ml to about 15 mg/ml, from about 10 mg/ml to about 15 mg/ml, from about 4 mg/ml to about 15 mg/ml, from about 4 mg/ml to about 12 mg/ml, from about 4 mg/ml to about 10 mg/ml, from about 4 mg/ml to about 8 mg/ml, from about 8 mg/ml to about 15 mg/ml, from about 8 mg/ml to about 12 mg/ml, or from about 8 mg/ml to about 10 mg/ml. In some embodiments a 20 ml vial containing a composition of the invention is diluted to about 60 ml with saline.

In certain embodiments, the diluted infusion is stored for no more than about 10, about 9, about 8, about 7, about 6, about 5, about 4, about 3, about 2, or about 1 hours at room temperature after dilution. In some embodiments, the diluted infusion is stored under refrigeration (about 2° C. to about 8° C.) for no more than about 1 week, about 6 days, about 5 days, about 4 days, about 3 days, about 2 days, about 1 day or about 12 hours after dilution.

Methods of the Invention

This disclosure provides a method of treating a subject afflicted with a disease or condition with any composition disclosed herein. In one embodiment, the method is directed to administering a pharmaceutical composition comprising an anti-LAG-3 antibody or antigen binding fragment thereof, or a pharmaceutical composition comprising an anti-LAG-3 or antigen binding fragment thereof, and an anti-PD-1 antibody, or anti-PD-L1 antibody, or antigen binding fragments thereof.

In some embodiments, the disease or condition is an infectious disease. In other embodiments, the disease or condition is cancer. In still other embodiments, the cancer is melanoma cancer, renal cancer, prostate cancer, breast cancer, colon cancer, oral cancer, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, or any combinations thereof. In yet other embodiments, the cancer is lung cancer, metastatic melanoma, glioblastoma, or renal cell carcinoma.

In certain embodiments, the cancer is squamous cell carcinoma, small cell lung cancer, non-small cell lung cancer, squamous non-small cell lung cancer (NSCLC), non-squamous NSCLC, glioma, gastrointestinal cancer, renal cancer (e.g., clear cell carcinoma), ovarian cancer, liver cancer, colorectal cancer, endometrial cancer, kidney cancer (e.g., renal cell carcinoma (RCC)), prostate cancer (e.g., hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (M0), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein can also be used for treatment of metastatic cancers.

In other embodiments, the cancer is refractory to treatment. In some embodiments, the cancer is refractory to treatment with an anti-PD1 antibody, or an anti-PD-L1 antibody, and/or an immune-oncology agent.

In certain embodiments, the composition is administered with any additional therapeutic agent. In some embodiments, the additional therapeutic agent is an anti-cancer agent or an immune-oncology agent. In other embodiments, the anti-cancer agent or immune-oncology agent is any anti-cancer agent or immune-oncology agent that is known in the art. In yet other embodiments, the anti-cancer agent or immune-oncology agent is a therapeutic antibody. In some embodiments, the therapeutic antibody is any antibody disclosed herein.

In other embodiments, the composition is administered intravenously. In some embodiments, the composition is reconstituted prior to administration. In yet other embodiments, the composition is diluted prior to administration. In a particular embodiment, the composition is administered at a flat dose. In other embodiments, the composition is administered at a weight-based dose.

In some embodiments, the composition is administered at least about weekly, at least about twice weekly, at least about every two weeks, at least about every three weeks, or at least about monthly. In some embodiments, the treatment lasts for at least about 4 weeks, at least about 8 weeks, at least about 12 weeks, at least about 3 months, at least about 6 months, at least about 9 months, at least about 1 year, at least about 18 months, at least about 2 years, or greater than 2 years. In some embodiments, an anti-LAG-3 antibody composition is administered biweekly at a dose up to 800 mg. In other embodiments, an anti-LAG-3 antibody composition (e.g., 80 mg, 160 mg or 240 mg) is administered biweekly and sequentially with an anti-PD-1 or anti-PD-L1 antibody composition (e.g., 240 mg). In some embodiments, the anti-LAG-3 antibody composition is administered before the anti-PD-1 or anti-PD-L1 antibody composition. In other embodiments, the anti-LAG-3 antibody composition is administered after the anti-PD-1 antibody composition. In other embodiments, the anti-LAG-3 antibody composition and the anti-PD-1 or anti-PD-L1 antibody composition are co-administered. In other embodiments, an infusion is administered over about 30 minutes.

In some embodiments, a pharmaceutical composition comprising an anti-LAG-3 antibody or antigen binding fragment thereof and a pharmaceutical composition comprising an anti-PD-1 antibody, or anti-PD-L1 antibody, or antigen binding fragments thereof are co-administered. In other embodiments, a pharmaceutical composition comprising an anti-LAG-3 antibody or antigen binding fragment thereof and a pharmaceutical composition comprising an anti-PD-1 antibody, or anti-PD-L1 antibody, or antigen binding fragments thereof are sequentially administered. In some embodiments, a pharmaceutical composition comprising an anti-LAG-3 antibody or antigen binding fragment thereof is administered prior to a pharmaceutical composition comprising an anti-PD-1 antibody, or anti-PD-L1 antibody, or antigen binding fragments thereof. In other embodiments, the anti-LAG-3 antibody or antigen-binding fragment thereof and the anti-PD-1 antibody, or anti-PD-L1 antibody, or antigen binding fragments thereof are administered as a first line of treatment. In other embodiments, the anti-LAG-3 antibody or antigen-binding fragment thereof and the anti-PD-1 antibody, or anti-PD-L1 antibody, or antigen binding fragments thereof are administered as a second line of treatment.

In some embodiments, the invention is directed to a method of modulating the immune response comprising administering any composition disclosed herein.

In certain embodiments, the composition of the present invention effectively increases the duration of survival of the subject. For example, the duration of survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 1 year or more when compared to another subject treated with only either another therapy (e.g., the standard of care), or (in the case of anti-LAG-3 antibody and anti-PD-1 antibody combination therapy) only one of the two members of the composition alone (e.g., an anti-PD-1 antibody alone). In some embodiments, the duration of survival is increased by at least about 2 months. In certain embodiments, the therapy of the present invention effectively increases the duration of progression-free survival of the subject. For example, the progression free survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 1 year when compared to an untreated subject or a subject treated only with another therapy (e.g., standard of care treatment) or (in the case of anti-LAG-3 antibody and anti-PD-1 or anti-PD-L1 antibody combination therapy) only one of the two members of the composition alone (e.g., an anti-PD-1 or anti-PD-L1 antibody alone). In some embodiments, the progression-free survival is increased by at least about 2 months. In certain embodiments, the therapy of the present invention effectively increases the response rate in a group of subjects. For example, the response rate in a group of subjects is increased by at least about 2%, at least about 3%, at least about 4%, at least about 5%, at least about 10%, at least about 15%, at least about 20%, at least about 25%, at least about 30%, at last about 35%, at least about 40%, at least about 45%, at least about 50%, at least about 55%, at least about 60%, at least about 70%, at least about 75%, at least about 80%, at least about 85%, at least about 90%, at least about 95%, at least about 99% or at least about 100% when compared to another group of subjects treated with only either another therapy (e.g., the standard of care) or (in the case of anti-LAG-3 antibody and anti-PD-1 or anti-PD-L1 antibody combination therapy) only one of the two members of the composition alone (e.g., an anti-PD-1 antibody or anti-PD-L1 antibody alone), i.e., monotherapy.

Dosages of Compositions Disclosed Herein

In some embodiments, the composition is administered at a flat dose regardless of the weight of the patient. For example, the anti-LAG-3 antibody or antigen binding fragment thereof or combination of anti-LAG-3 antibody or antigen binding fragment thereof, and anti-PD-1 antibody, or anti-PD-L1 antibody, or antigen binding fragments thereof can be administered at a flat dose of 0.1, 0.5, 1, 2, 3, 4, 5, 10, 15, 20, 50, 75, 80, 200, 240, 300, 360, 400, 480, 500, 750 or 1,500 mg of antibody or any other dose disclosed herein, without regard to the patient's weight. In some embodiments the composition is administered at a weight-based dose at any dose disclosed herein.

In certain embodiments of the methods of the invention, the therapeutically effective dosage of the anti-LAG-3 antibody or antigen binding fragment thereof is about 60 mg, about 80 mg, about 100 mg, about 120 mg, about 140 mg, about 160 mg, about 180 mg, about 200 mg, about 220 mg, about 240 mg, about 260 mg, about 280 mg, or about 300 mg. In other embodiments, the therapeutically effective dosage of the anti-LAG-3 antibody or antigen binding fragment thereof is from about 60 mg to about 300 mg, from about 60 mg to about 240 mg, from about 60 mg to about 160 mg, from about 60 mg to about 80 mg, from about 80 mg to about 300 mg, from about 80 mg to about 240 mg, from about 80 mg to about 160 mg, from about 160 mg to about 300 mg, or from about 160 mg to about 240 mg. In other embodiments, the therapeutically effective dosage of the anti-LAG-3 antibody or antigen binding fragment thereof is about 80 mg, about 160 mg, about 200 mg, or about 240 mg. In other embodiments, the therapeutically effective dosage of the anti-LAG-3 antibody or antigen binding fragment thereof is a least about 0.5 mg/kg, at least about 1 mg/kg, at least about 2 mg/kg, at least about 3 mg/kg or at least about 5 mg/kg. In other embodiments, the therapeutically effective dosage of anti-LAG-3 antibody or antigen binding fragment thereof is from about 0.5 mg/kg to about 5 mg/kg, from about 0.5 mg/kg to about 5 mg/kg, from about 0.5 mg/kg to about 3 mg/kg, or from about 0.5 mg/kg to about 2 mg/kg. In some embodiments, the therapeutically effective dosage of the anti-LAG-3 antibody or antigen binding fragment thereof is at least about 1 mg/kg.

In certain embodiments of the methods of the invention, the therapeutically effective dosage of the anti-PD-1 antibody, or anti-PD-L1 antibody, or antigen binding fragments thereof is about 60 mg, about 80 mg, about 100 mg, about 120 mg, about 140 mg, about 160 mg, about 180 mg, about 200 mg, about 220 mg, about 240 mg, about 260 mg, about 280 mg, or about 300 mg. In other embodiments, the therapeutically effective dosage of the anti-PD-1 antibody, or anti-PD-L1 antibody, or antigen binding fragments thereof is about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg. In other embodiments, the therapeutically effective dosage of the anti-PD-1 antibody, anti-PD-L1 antibody, or antigen binding fragment thereof is between about 60 mg and about 300 mg, between about 60 mg and about 240 mg, between about 100 mg and about 240 mg, or between about 200 mg and about 300 mg. In other embodiments, the therapeutically effective dosage of the anti-PD-1 antibody, or anti-PD-L1 antibody, or antigen binding fragments thereof is at least about 80 mg, about 160 mg, or about 240 mg. In other embodiments, the therapeutically effective dosage of the anti-PD-1 antibody, or anti-PD-L1 antibody, or antigen binding fragments thereof is a least about 0.5 mg/kg, at least about 1 mg/kg, at least about 2 mg/kg, at least about 3 mg/kg or at least about 5 mg/kg. In other embodiments, the therapeutically effective dosage of anti-PD-1 antibody, or anti-PD-L1 antibody, or antigen binding fragments thereof is from about 0.5 mg/kg to about 5 mg/kg, from about 0.5 mg/kg to about 5 mg/kg, from about 0.5 mg/kg to about 3 mg/kg, or from about 0.5 mg/kg to about 2 mg/kg. In some embodiments, the therapeutically effective dosage of the anti-PD-1 antibody, or anti-PD-L1 antibody, or antigen binding fragments thereof is a least about 1 mg/kg.

In some embodiments, the composition is administered by intravenous infusion once about per week, once about every 2 weeks, once about every 3 weeks, or once about a month (i.e., about every 4 weeks). In some embodiments, the infusion occurs over at least about 10 minutes, about 20 minutes, about 30 minutes, about 45 minutes, about 60 minutes, about 90 minutes, about 2 hours, about 3 hours, about 4 hours, or about 5 hours. An infusion solution of the invention can be prepared in an empty intravenous infusion bag by adding an amount of saline to a bag before or after an anti-LAG-3 antibody drug product is added to the bag. Another infusion solution of the invention can be prepared in an empty intravenous infusion bag by adding an amount of saline to a bag before or after an anti-LAG-3 antibody drug product and anti-PD-1 antibody is added to the bag.

In certain embodiments, the dosage for treating solid tumors is 20 mg of anti-LAG-3 antibody or antigen binding fragment thereof and 80 mg of anti-PD-1 antibody, anti-PD-L1 antibody, or antigen binding fragment thereof. In certain other embodiments, the dosage for treating solid tumors (e.g., lung) is 20 mg of anti-LAG-3 antibody or antigen binding fragment thereof and 240 mg of anti-PD-1 antibody, anti-PD-L1 antibody, or antigen binding fragment thereof. In certain other embodiments, the dosage for treating solid tumors (e.g., melanoma, RCC, NSCLC, HCC, SCCHN) is 80 mg of anti-LAG-3 antibody or antigen binding fragment thereof and 240 mg of anti-PD-1 antibody, anti-PD-L1 antibody, or antigen binding fragment thereof. In certain other embodiments, the dosage for treating solid tumors is 240 mg of anti-LAG-3 antibody or antigen binding fragment thereof and 240 mg of anti-PD-1 antibody, anti-PD-L1 antibody, or antigen binding fragment thereof. In certain other embodiments, the dosage for treating solid tumors (e.g., melanoma, RCC, NSCLC, gastric, HCC, SCCHN) is 160 mg of anti-LAG-3 antibody or antigen binding fragment thereof and 240 mg of anti-PD-1 antibody, anti-PD-L1 antibody, or antigen binding fragment thereof.

In certain other embodiments, the dosage for treating hematological malignancies is 80 mg of anti-LAG-3 antibody or antigen binding fragment thereof and 240 mg of anti-PD-1 antibody, anti-PD-L1 antibody, or antigen binding fragment thereof. In certain other embodiments, the dosage for treating hematological malignancies (e.g., Hodgkin's lymphoma, DLBCL) is 160 mg of anti-LAG-3 antibody or antigen binding fragment thereof and 240 mg of anti-PD-1 antibody, anti-PD-L1 antibody, or antigen binding fragment thereof. In certain other embodiments, the dosage for treating hematological malignancies (e.g., Hodgkin's lymphoma, DLBCL) is 240 mg of anti-LAG-3 antibody or antigen binding fragment thereof and 240 mg of anti-PD-1 antibody, anti-PD-L1 antibody, or antigen binding fragment thereof.

In certain other embodiments, the anti-LAG-3 antibody is BMS-986016 and the anti-PD-1 antibody is nivolumab, the anti-LAG-3 antibody is MK-4280 and the anti-PD-1 antibody is pembrolizumab, the anti-LAG-3 antibody is REGN3767 and the anti-PD-1 antibody is REGN2810, the anti-LAG-3 antibody is LAG525 and the anti-PD-1 is REGN2810, or the anti-LAG-3 antibody is LAG525 and the anti-PD-1 antibody is PDR001.

Actual dosage levels of the active ingredients in the pharmaceutical compositions of the present invention can be flat or varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

Instruments, Devices, and Kits

Also within the scope of the present invention are medical instruments or devices that comprise a composition of the invention (e.g., comprising an anti-LAG-3 antibody or antigen binding fragment thereof or an anti-LAG-3 antibody or antigen binding fragment thereof and an anti-PD-1 antibody, or anti-PD-L1 antibody, or antigen binding fragments thereof). Such instruments or devices include, for example, syringes and intravenous bags. Such syringes can be single chamber (e.g., containing a composition comprising an anti-LAG-3 antibody or antigen binding fragment thereof, or an anti-LAG-3 antibody or antigen binding fragment thereof and an anti-PD-1 antibody, or anti-PD-L1 antibody, or antigen binding fragments thereof) or dual chamber (e.g., containing a composition comprising an anti-LAG-3 antibody or antigen binding fragment thereof in one chamber and a composition comprising an anti-PD-1 antibody, or anti-PD-L1 antibody, or antigen binding fragments thereof in another chamber).

Also within the scope of the present invention are kits comprising a composition of the invention (e.g., comprising an anti-LAG-3 antibody or antigen binding fragment thereof or an anti-LAG-3 antibody or antigen binding fragment thereof and an anti-PD-1 antibody, or anti-PD-L1 antibody, or antigen binding fragments thereof). Kits of the invention can include instructions for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit comprising: (a) an appropriate dosage of the composition disclosed herein and (b) instructions for using the composition in any of the methods disclosed herein.

The present invention is further illustrated by the following examples which should not be construed as further limiting.

EXAMPLES

Several feasibility studies were performed to prepare compositions of the invention and evaluate their stability.

Example 1

Drug Substance Formulation

Compositions of the invention were prepared using an anti-LAG-3 (BMS-986016) drug substance (DS). The BMS-986016 DS formulation contains approximately 50 mg/mL (45-60 mg/mL) of anti-LAG-3 antibody in 20 mM histidine buffer, 250 mM sucrose, 0.05% polysorbate 80 (PS80) at pH 5.5. This DS formulation can be applied to both drug products (PD) for anti-LAG-3 monotherapy and anti-LAG-3 and anti-PD-1/anti-PD-L1 combination therapy of the invention.

In order to prepare fixed dose ratio combinations (FDRCs) of BMS-986016 with nivolumab (Nivo) DS for anti-LAG-3/anti-PD-1 combination therapy, studies to select a DS formulation of BMS-986016 were conducted. A citrate-based BMS-986016 DS formulation was also used. This DS contains approximately 50 mg of BMS-986016, 20 mM citrate, 150 mM NaCl and 0.05% PS80.

For two drug substances, citrate-based and histidine-based, used for FDRCs, particulate formation was observed for citrate-based DS in freeze/thaw stability study. No particulate stability issues were observed for histidine-based DS. There was some increase of oxidation level at 25° C. and 40° C. (9% and 29% respectively) for histidine-based DS after 3-month exposure. However, there was essentially no increase at 5° C. after 3 months. Therefore, significant oxidation of DS did not occur when stored at low temperature.

Monotherapy Drug Product Formulation

The anti-LAG-3 monotherapy drug product (DP) formulation contains 10 mg/mL anti-LAG-3 antibody in 20 mM histidine buffer, 250 mM sucrose, and 0.05% PS80 at pH 5.5 with or without a chelator of 20 μM DTPA or 50 μM EDTA. The DP was manufactured by dilution of BMS-986016 DS formulated in 20 mM histidine buffer, 250 mM sucrose, 0.05% PS80 at pH 5.5. A chelator (DTPA or EDTA) can also be added to reach 20 μM DTPA or 50 μM EDTA.

The pH of the DP solution was similar to that of the DS at pH 5.5. This value provides an excellent and optimal pH-stability profile for controlling possible degradation of the drug. Addition of a chelator effectively increases the stability of the formulation for a much longer product shelf life (e.g., at least about 5 years) and significantly enhanced ruggedness of the drug product, particularly when metal ions are presented in any components of formulation, packaging, and/or released from a metal material during manufacture. Therefore, the monotherapy DP showed excellent stability and all properties acceptable for monotherapy and/or co-infusion with nivolumab DP.

Fixed Dose Ratio Combination (FDRC) Drug Product Formulation

The FDRC drug product (DP) formulation contains 4-12 mg/mL of anti-LAG-3 antibody and 12 mg/mL of nivolumab in 20 mM histidine buffer, 250 mM sucrose, and 0.05% PS80 at pH 5.8 with a chelator of 20 μM DTPA or 50 μM EDTA.

The DP was manufactured by combining and diluting BMS-986016 DS formulated in 20 mM histidine buffer, 250 mM sucrose, 0.05% PS80 at pH 5.5 and BMS-936558 DS formulated in 20 mM histidine buffer, 250 mM sucrose, 0.05% PS80 at pH 6.0. A chelator (DTPA or EDTA) can also be added to reach 20 μM DTPA or 50 μM EDTA.

The pH of drug product solution (pH 5.8) was a result of two drug substances combined. This value provides an excellent and optimal pH-stability profile for controlling any potentially possible degradation of the drugs. As supported in the following Examples, addition of a chelator effectively increased the stability of the formulation for a much longer product shelf life (e.g., at least about 5 years) and significantly enhanced ruggedness of the drug product, particularly when metal ions are presented in any components of formulation and/or released from a metal material during manufacture. Therefore, the FDRC DP formulation showed excellent stability and all properties acceptable for a drug product used for combination therapies with nivolumab DP.

Example 2

A feasibility study was performed to evaluate a composition of the invention containing an anti-LAG-3 antibody.

Materials

Drug Substances

BMS-986016 drug substance (DS) was used. The protein concentration of the DS was about 50 mg/mL.

Drug Product Formulation Buffer and Excipients

Buffer and excipients were obtained from BMS, New Brunswick.

Primary Packaging Materials for the Drug Product

The drug product (DP) stability samples were packed in 10cc Type I clear flint glass tubing vials with FluroTec® coated stoppers. Vials were sealed with 20 mm aluminum seals.

Methods

Sample Analysis

At each time point, sample vials were analyzed by visual appearance, pH at room temperature, HIAC, size exclusion chromatography, and imaged capillary isoelectric focusing (cIEF). HIAC (Royco) is a light obscuration based particle counting technique instrument.

Size exclusion chromatography (SEC) was performed by analytical size exclusion HPLC (SE-HPLC) using a TSK-GEL® G3000SW$_{XL}$ with a TSKGEL® Guard SW$_{XL}$ guard column on a WATERS® 2695 ALLIANCE® HPLC with a 2497 dual wavelength UV detector using EMPOWER™ 2 Software. The system was equilibrated with 0.1 M NaH$_2$PO$_4$, 0.1 M Na$_2$SO$_4$, and 15% acetonitrile (ACN), at pH 6.8 (mobile phase). Samples were analyzed neat unless the concentration was greater than 125 mg/mL. If the sample concentration was greater than 125 mg/mL, the sample was diluted to 50 mg/mL with the corresponding buffer. Samples were transferred to an HPLC vial prior to analysis and stored in the analytical HPLC system at a temperature of 5° C.±3° C. A total of 100 μg of sample were injected for analysis and were run isocratically with a column temperature of 22° C.

using the mobile phase. The flow rate was 1.0 mL/min with a run time per sample of 20 min and a detection wavelength of 280 nm.

Imaged capillary isoelectric focusing (cIEF) was performed using a Protein SIMPLE™ iCE3 instrument with an Alcott sampler. Samples were analyzed at a concentration of 25 mg/mL with 2 M urea and 0.35% methyl cellulose (MC). A 50 mm capillary with a 100 μm internal diameter was used to perform separation. The electrolyte solution was 80 mM $H_3PO_4$ in 0.1% MC, and the catholyte solution was 100 mM NaOH in 0.1% MC. The carrier ampholytes were 1% PHARMALYTE® 5-8 and 3% PHARMALYTE® 8-10.5. Focusing time was 13 minutes with focusing voltage starting at 1.5 kV (300 V/cm) for the first minute followed by 3 kV (600 V/cm) for the remaining 12 minutes. Detection was performed at 280 nm.

BMS-986016 Drug Product Formulations and Comparator without DTPA

Formulation Buffer Preparation

Formulation buffer (20 mM histidine, 250 mM sucrose, and 0.05% polysorbate 80 (PS80), pH 5.5) was prepared by adding the following excipients in Table 3, dissolving, mixing and q.s. with Milli-Q water in 1-L volumetric flask.

TABLE 3

Composition of Formulation Buffer

| Buffer ingredient | Conc. |
|---|---|
| Histidine | 20 mM |
| Sucrose | 8.56% |
| PS80 | 0.05% |

5 mM Diethylenetriaminepentaacetic Acid (DTPA) Solution

A 5 mM DTPA solution was prepared with Milli-Q water, and filtered using a 0.22 μm Millipore Stericup® Filter Unit. The solution was prepared by weighing 0.098 g of DTPA (MW393.35), adding 50 mL of water and stirring for 1 hour to obtain a clear solution.

Drug Product Formulation Solutions and Comparator without DTPA

A total of eight formulation bulk solutions were prepared as listed in Table 4. The formulation F5.5N did not contain DTPA and was used as a comparator in the study.

TABLE 4

Formulation solutions with pH variables

| Formulation# | pH | Drug conc. (mg/mL) | Histidine conc. (mM) | Sucrose conc. (mM) | PS80 conc. (w/v %) | DTPA conc. (uM) |
|---|---|---|---|---|---|---|
| F4.8 | 4.80 | 10 | 20 | 250 | 0.05 | 20 |
| F5.0 | 5.00 | 10 | 20 | 250 | 0.05 | 20 |
| F5.25 | 5.25 | 10 | 20 | 250 | 0.05 | 20 |
| F5.5 | 5.50 | 10 | 20 | 250 | 0.05 | 20 |
| F5.5N | 5.50 | 10 | 20 | 250 | 0.05 | 0 |
| F5.75 | 5.75 | 10 | 20 | 250 | 0.05 | 20 |
| F6.0 | 6.00 | 10 | 20 | 250 | 0.05 | 20 |
| F6.25 | 6.25 | 10 | 20 | 250 | 0.05 | 20 |

BMS-986016 DP Vial Filling

The following steps were taken to fill bulk solutions into 10cc glass vials:

(1) Confirm the pH and A280 concentration of the final formulations and sterile filter using 0.22 μm Millipore Stericup® Filter Unit;

(2) Fill the formulation into 10cc Schott vials. The fill volumes are per Table 5 except for F5.5 that will be filled with 10.5 mL per vial. Fill a total of 60 vials per formulation. For F5.5, fill additional 8 vials for RT/RL condition; and (3) Seal and label the vials appropriately and store at the temperatures as listed in Table 6.

TABLE 5

Vial fill volumes and analytical tests

| Test | Amount Required/ available |
|---|---|
| Vial 1 | |
| HIAC | 6 mL |
| Vial 2 | |
| MFI | 2 mL |
| Vial 3 | |
| Visual, pH, $A_{280}$, SEC, iCiEF, CE-SDS | 6 mL |
| Vial 4 | |
| Reservation | 2 mL |

TABLE 6

Stability temperatures and time points

| Storage Temp. | Initial | Sampling Interval |  |  |  |  |  |  |  |
|---|---|---|---|---|---|---|---|---|---|
|  |  | 2W | 1M | 3M | 6M | 12M | 18M | 24M | Retains |
| 5° C. | 4 vials |  |  |  | 4 vials | 4 vials | 4 vials | 4 vials | 4 vials |
| 25° C. |  |  | 4 vials | 4 vials | 4 vials | 4 vials |  |  |  |
| 40° C. |  |  | 4 vials | 4 vials |  |  |  |  |  |
| −60° C. |  |  | 4 vials |  | 4 vials |  |  |  | 4 vials |
| RT/RL* |  | 4 vials | 4 vials |  |  |  |  |  |  |

*Room temperature (23 ± 3° C.) and room light (1000 ± 200 lux) and only for formulation F5.5.

Stability Test Methods

The test methods for stability samples are listed in Table. These methods were either routine laboratory methods such as pH measurement or the development methods used by BMS analytical group.

TABLE 7

Stability Sample Test Methods

| Test Group | Test Name | Method |
|---|---|---|
| a | Appearance | Visual observation |
|  | pH | pH meter |
|  | Protein Conc. (A$_{280}$) | Trinean microfluidic chip based UV/Vis method |
| b | Particulate Matter | HIAC |
| c | iCIEF | Development method |
|  | CE-SDS (Non-Reduced) | Development method |
| d | SEC | Development method |

Results

Up to three months of stability data were available for this study. The results are summarized in following sections.

pH and Protein Concentration

The stability samples were monitored for up to three months. For all samples tested, the solution appearance in glass vial was clear and no visible particulates were observed. For samples without DTPA (formulation #F5.5N), slightly increased yellow color was observed at 40° C.

The pH value of aLAG-3 drug product is one of critical quality attributes (CQA) as it can affect the drug product stability. The pH data of stability samples are provided in Table 8. The results show that there was essentially no change of pH for all samples at various storage conditions of 3 months, indicating that 20 mM buffer strength had sufficient buffer capacity to control solution pH.

TABLE 8 pH of Formulation Samples

| Formulation# | Storage Temperature, ° C. | Target pH | T0 | 2-weeks | 1-month | 3-months |
|---|---|---|---|---|---|---|
| F4.8 | 25 | 4.80 | 4.93 |  | 4.89 | 4.98 |
|  | 40 |  |  |  | 4.89 | 4.98 |
|  | −60 |  |  |  | 4.89 | — |
| F5.0 | 25 | 5.00 | 5.05 |  | 5.04 | 5.11 |
|  | 40 |  |  |  | 5.04 | 5.09 |
|  | −60 |  |  |  | 5.04 | — |
| F5.25 | 25 | 5.25 | 5.22 |  | 5.26 | 5.19 |
|  | 40 |  |  |  | 5.26 | 5.17 |
|  | −60 |  |  |  | 5.26 | — |
| F5.5 | 25 | 5.50 | 5.44 |  | 5.48 | 5.42 |
|  | 40 |  |  |  | 5.48 | 5.44 |
|  | −60 |  |  |  | 5.48 | — |
|  | RT/RL |  |  | 5.48 | 5.48 | — |
| F5.5N | 25 | 5.50 | 5.41 |  | 5.47 | 5.39 |
|  | 40 |  |  |  | 5.47 | 5.37 |
|  | −60 |  |  |  | 5.47 | — |
| F5.75 | 25 | 5.75 | 5.64 |  | 5.77 | 5.63 |
|  | 40 |  |  |  | 5.77 | 5.61 |
|  | −60 |  |  |  | 5.77 | — |
| F6.0 | 25 | 6.00 | 5.88 |  | 6.01 | 5.92 |
|  | 40 |  |  |  | 6.01 | 5.83 |
|  | −60 |  |  |  | 6.01 | — |
| F6.25 | 25 | 6.25 | 6.11 |  | 6.26 | 6.08 |
|  | 40 |  |  |  | 6.26 | 6.12 |
|  | −60 |  |  |  | 6.26 | — |

The results of protein concentration are showed in Table 9. The data also showed no significant change from initial for all samples of different pH values with or without DTPA from −60° C. to 40° C., indicating no loss of protein mass even under either highly stressed temperature of 40° C. or by freeze/thaw between −60° C. and room temperature.

TABLE 9

Protein Concentration (mg/mL)

| Formulation # | Storage Temperature, ° C. | T0 | 2-weeks | 1-month | 3-months |
|---|---|---|---|---|---|
| F4.8 | 25 | 10.8 |  | 10.8 | 10.9 |
|  | 40 |  |  | 11.0 | 10.8 |
|  | −60 |  |  | 10.8 | — |
| F5.0 | 25 | 10.7 |  | 10.7 | 10.8 |
|  | 40 |  |  | 10.7 | 10.8 |
|  | −60 |  |  | 10.7 | — |
| F5.25 | 25 | 10.8 |  | 10.9 | 10.8 |
|  | 40 |  |  | 10.7 | 10.8 |
|  | −60 |  |  | 10.8 | — |
| F5.5 | 25 | 10.7 |  | 10.4 | 10.8 |
|  | 40 |  |  | 10.8 | 10.5 |
|  | −60 |  |  | 11.3 | — |
|  | RT/RL |  | 11.1 | 10.8 | — |
| F5.5N | 25 | 10.8 |  | 10.8 | 10.8 |
|  | 40 |  |  | 10.8 | 10.7 |
|  | −60 |  |  | 10.8 | — |
| F5.75 | 25 | 10.9 |  | 10.9 | 10.9 |
|  | 40 |  |  | 11.2 | 10.9 |
|  | −60 |  |  | 10.9 | — |
| F6.0 | 25 | 10.8 |  | 10.8 | 10.9 |
|  | 40 |  |  | 10.8 | 10.9 |
|  | −60 |  |  | 11.5 | — |
| F6.25 | 25 | 10.8 |  | 11.5 | 10.9 |
|  | 40 |  |  | 10.8 | 10.9 |
|  | −60 |  |  | 10.9 | — |

Particulates

The results for particulate matter count are shown in Table for ≥2, ≥10 and ≥25 μm size respectively. The data indicate the count numbers are within USP limits and relatively low. High numbers observed for ≥2 μm particulates in some samples at 40° C. storage condition, which is not unexpected as the samples exposed to such a high temperature for a period of months. Even with these numbers, the particulate count is still considered to be very low. The impact of pH on particulate count is also shown in the table, and overall there is no pH impact.

TABLE 10

Particulate Count (≥2 μm, ≥10 μm, ≥25 μm) by HIAC (#/mL)

| Formulation # | Storage Temperature, ° C. | T0 | 2-weeks | 1-month | 3-months |
|---|---|---|---|---|---|
| F4.8 | 25 | 76, 25, 19 |  | 94, 8, 3 | 263, 15, 0 |
|  | 40 |  |  | 136, 3, 0 | 1198, 5, 0 |
|  | −60 |  |  | 113, 10, 2 | — |
| F5.0 | 25 | 93, 10, 1 |  | 76, 1, 0 | 93, 5, 0 |
|  | 40 |  |  | 126, 3, 0 | 1810, 5, 0 |
|  | −60 |  |  | 53, 4, 3 | — |
| F5.25 | 25 | 63, 3, 0 |  | 214, 12, 8 | 198, 4, 0 |
|  | 40 |  |  | 137, 14, 10 | 4487, 6, 0 |
|  | −60 |  |  | 128, 5, 1 | — |
| F5.5 | 25 | 26, 3, 1 |  | 33, 1, 0 | 188, 6, 0 |
|  | 40 |  |  | 1194, 0, 0 | 5613, 10, 0 |
|  | −60 |  |  | 90, 2, 0 | — |
|  | RT/RL |  | 134, 2, 0 | 330, 10, 0 | — |
| F5.5N | 25 | 23, 5, 0 |  | 115, 8, 1 | 180, 6, 0 |
|  | 40 |  |  | 76, 3, 1 | 456, 17, 0 |
|  | −60 |  |  | 597, 2, 0 | — |
| F5.75 | 25 | 617, 5, 1 |  | 107, 10, 6 | 312, 15, 0 |
|  | 40 |  |  | 1989, 7, 1 | 5080, 3, 0 |
|  | −60 |  |  | 265, 19, 10 | — |

TABLE 10-continued

Particulate Count (≥2 μm, ≥10 μm, ≥25 μm) by HIAC (#/mL)

| Formulation # | Storage Temperature, ° C. | T0 | 2-weeks | 1-month | 3-months |
|---|---|---|---|---|---|
| F6.0 | 25 | 517, 10, 2 | | 64, 2, 1 | 73, 3, 0 |
| | 40 | | | 55, 1, 0 | 2898, 35, 3 |
| | −60 | | | 160, 8, 1 | — |
| F6.25 | 25 | 49, 8, 2 | | 102, 8, 0 | 207, 4, 0 |
| | 40 | | | 163, 8, 0 | 222, 8, 0 |
| | −60 | | | 105, 2, 1 | — |

Aggregates and Fragments

High molecular weight (HMW) and low molecular weight (LMW) species of antibody as well as antibody monomer were analyzed by SEC. Results are shown in Table. The data indicate no significant decrease of monomer (<0.2%) from the initial time point for the samples stored at 25° C. for up to 3 months or at RT/RL for up to 1 month. However, significant decrease was observed at 40° C. for up to 3 months or at 25° C. for 6 months due to increase of HMWs and LMWs. The increase of HMWs was more significant than that of LMWs. Table 11 also shows that the increase of HMWs and LMWs was affected by pH and both increases with decreasing pH values. Additionally, the impact of chelator DTPA is obvious in Table 11. The formulation without DTPA (F5.5N) shows ~3 fold more increase of HMWs at 40° C. after three month exposure than that of DTPA-containing formulations, indicating the stability enhancement was achieved by DTPA. It is clear that addition of DTPA will further extend the shelf life of the drug product to be within the specification of HMWs, monomer and LMWs at the intended drug product storage temperature of 2-8° C.

TABLE 11

Size Variant Distribution (% HMWs, Monomer, LMWs) in Formulations

| Formulation # | Storage temperature, ° C. | T0 | 2-weeks | 1-month | 3-months |
|---|---|---|---|---|---|
| F4.8 | 25 | 0.5, 98.7, 0.8 | | 0.5, 98.8, 0.7 | 0.6, 98.8, 0.6 |
| | 40 | | | 1.6, 97.4, 1.0 | 8.2, 88.6, 3.3 |
| | −60 | | | 0.5, 98.9, 0.6 | — |
| F5.0 | 25 | 0.6, 98.7, 0.8 | | 0.5, 98.7, 0.8 | 0.6, 98.8, 0.6 |
| | 40 | | | 1.3, 97.7, 1.0 | 6.6, 90.3, 3.1 |
| | −60 | | | 0.5, 98.9, 0.6 | — |
| F5.25 | 25 | 0.6, 98.6, 0.8 | | 0.5, 98.8, 0.8 | 0.6, 98.8, 0.6 |
| | 40 | | | 0.9, 98.1, 1.0 | 4.8, 92.7, 2.5 |
| | −60 | | | 0.5, 98.8, 0.6 | — |
| F5.5 | 25 | 0.6, 98.6, 0.8 | | 0.5, 98.7, 0.8 | 0.6, 99.8, 0.6 |
| | 40 | | | 0.7, 98.3, 1.0 | 3.3, 94.7, 2.0 |
| | −60 | | | 0.5, 98.8, 0.6 | — |
| | RT/RL | | 0.6, 98.8, 0.7 | 0.7, 98.7, 0.7 | — |
| F5.5N | 25 | 0.6, 98.6, 0.8 | | 0.6, 98.7, 0.8 | 0.8, 98.6, 0.6 |
| | 40 | | | 1.0, 98.1, 0.9 | 10.3, 86.6, 3.1 |
| | −60 | | | 0.5, 98.9, 0.6 | — |
| F5.75 | 25 | 0.6, 98.8, 0.7 | | 0.5, 98.7, 0.7 | 0.6, 98.8, 0.6 |
| | 40 | | | 0.5, 98.6, 0.9 | 2.7, 95.4, 1.9 |
| | −60 | | | 0.5, 98.8, 0.7 | — |
| F6.0 | 25 | 0.6, 98.7, 0.8 | | 0.5, 98.8, 0.7 | 0.6, 98.8, 0.6 |
| | 40 | | | 0.5, 98.7, 0.9 | 2.2, 96.0, 1.8 |
| | −60 | | | 0.6, 98.8, 0.7 | — |
| F6.25 | 25 | 0.6, 98.7, 0.8 | | 0.6, 98.7, 0.7 | 0.8, 98.7, 0.6 |
| | 40 | | | 0.5, 98.6, 0.8 | 1.8, 96.5, 1.7 |
| | −60 | | | 0.5, 98.8, 0.6 | — |

Purity

CE-SDS was used to monitor the purity of the formulation samples. The results of Reduced CE-SDS show essentially no purity change from initial for the samples at RT/RL, −60° C. and 2° C. (<0.5%) for up to 3 months (Table). Very slight decrease (<2%) was observed at 40° C. Non-Reduced CE-SDS analysis was also performed. The results are shown in Table. Slight change of up to −6% was observed at 40° C. for the samples in low pH region. With increasing pH, there was no significant change (<2%) even at 40° C. for 3 months. For all other samples, there was essentially no change (<1%) from initial. There was also no difference between formulations with and without DTPA, indicating CE-SDS purity did not affected by addition of DTPA. These purity data indicate that the drug product formulation should have no or very minimum purity change at intended storage conditions of 2-8° C., protected from light for a long-term shelf-life.

TABLE 12

Purity by Reduced CE-SDS

| Formulation # | Storage temperature, ° C. | T0 | 2-weeks | 1-month | 3-months |
|---|---|---|---|---|---|
| F4.8 | 25 | 99.7 | | 99.7 | 99.7 |
| | 40 | | | 99.2 | 98.1 |
| | −60 | | | 99.7 | — |
| F5.0 | 25 | 99.7 | | 99.5 | 99.8 |
| | 40 | | | 99.2 | 98.3 |
| | −60 | | | 99.7 | — |
| F5.25 | 25 | 99.7 | | 99.5 | 99.7 |
| | 40 | | | 99.3 | 98.6 |
| | −60 | | | 99.7 | — |
| F5.5 | 25 | 99.8 | | 99.5 | 99.7 |
| | 40 | | | 99.3 | 98.9 |
| | −60 | | | 99.8 | — |
| | RT/RL | | 99.8 | 99.7 | — |

TABLE 12-continued

Purity by Reduced CE-SDS

| Formulation # | Storage temperature, °C | T0 | 2-weeks | 1-month | 3-months |
|---|---|---|---|---|---|
| F5.5N | 25 | 99.7 | | 99.7 | 99.7 |
| | 40 | | | 99.5 | 98.6 |
| | −60 | | | 99.6 | — |
| F5.75 | 25 | 99.8 | | 99.5 | 99.8 |
| | 40 | | | 99.5 | 98.8 |
| | −60 | | | 99.8 | — |
| F6.0 | 25 | 99.7 | | 99.7 | 99.8 |
| | 40 | | | 99.6 | 98.9 |
| | −60 | | | 99.7 | — |
| F6.25 | 25 | 99.7 | | 99.6 | 99.8 |
| | 40 | | | 99.5 | 98.8 |
| | −60 | | | 99.7 | — |

TABLE 13

Purity by Non-Reduced CE-SDS

| Formulation # | Storage temperature, °C | T0 | 2-wks | 1-month | 3-months |
|---|---|---|---|---|---|
| F4.8 | 25 | 99.9 | | 99.7 | 99.3 |
| | 40 | | | 99.3 | 93.8 |
| | −60 | | | 99.8 | — |
| F5.0 | 25 | 99.9 | | 99.6 | 99.5 |
| | 40 | | | 99.3 | 94.2 |
| | −60 | | | 99.8 | — |
| F5.25 | 25 | 99.9 | | 99.8 | 99.6 |
| | 40 | | | 99.2 | 97.9 |
| | −60 | | | 99.8 | — |
| F5.5 | 25 | 99.9 | | 99.8 | 99.6 |
| | 40 | | | 99.1 | 97.8 |
| | −60 | | | 99.8 | — |
| | RT/RL | | 99.6 | 99.6 | — |
| F5.5N | 25 | 99.9 | | 99.8 | 99.5 |
| | 40 | | | 99.2 | 97.5 |
| | −60 | | | 99.8 | — |
| F5.75 | 25 | 99.9 | | 99.8 | 99.6 |
| | 40 | | | 99.2 | 97.4 |
| | −60 | | | 99.7 | — |
| F6.0 | 25 | 99.9 | | 99.8 | 99.6 |
| | 40 | | | 99.2 | 97.3 |
| | −60 | | | 99.6 | — |
| F6.25 | 25 | 99.9 | | 99.8 | 99.6 |
| | 40 | | | 99.2 | 97.2 |
| | −60 | | | 99.6 | — |

Charge Variants

The charge distribution change of formulation samples was monitored by iCIEF. It is expected that acidic peaks would increase and basic or main peaks would decrease with time if charge degradants forms. The iCIEF results ( Table, Table and Table) show no significant change (<5%) of charge distribution from initial for the samples exposed to −60° C. and 25° C. for up to 3 months or at RT/RL for 1 month. Significant change was observed at 40° C. after 3 months, which is not unexpected at such a highly stressed condition. As expected, the acidic peaks increased with increasing pH at 40° C., and the increased peak area was a result of peak area reduction of main peak and basic peaks. These results indicate that the all formulations were relatively stable for charge distribution at the intended storage condition of 2-8° C. for DP, but extended high temperature exposure could cause BMS-986016 degradation to form more acidic species, such as deamidated by-products.

Table 14 also shows significant difference (>5%) in acidic species between DTPA and non-DTPA samples at 40° C. for 3 months, indicating DTPA enhanced stability of charge distribution of the mAb. Therefore, further increase of shelf life at 2-8° C. can reasonably be expected with DTPA samples.

TABLE 14

% Peak Area of Acidic Variants

| Formulation # | Storage temperature, °C | T0 | 2-weeks | 1-month | 3-months |
|---|---|---|---|---|---|
| F4.8 | 25 | 12.6 | | 14.5 | 16.4 |
| | 40 | | | 21.0 | 37.7 |
| | −60 | | | 14.2 | — |
| F5.0 | 25 | 13.4 | | 14.8 | 16.2 |
| | 40 | | | 20.5 | 37.6 |
| | −60 | | | 13.8 | — |
| F5.25 | 25 | 13.0 | | 13.7 | 16.5 |
| | 40 | | | 21.2 | 39.0 |
| | −60 | | | 12.9 | — |
| F5.5 | 25 | 12.9 | | 13.2 | 16.7 |
| | 40 | | | 22.0 | 41.5 |
| | −60 | | | 13.0 | — |
| | RT/RL | | 12.9 | 15.3 | — |
| F5.5N | 25 | 13.2 | | 14.8 | 17.4 |
| | 40 | | | 22.4 | 47.9 |
| | −60 | | | 13.5 | — |
| F5.75 | 25 | 12.4 | | 13.9 | 16.8 |
| | 40 | | | 23.1 | 43.6 |
| | −60 | | | 12.4 | — |
| F6.0 | 25 | | | 14.4 | 18.5 |
| | 40 | 13.2 | | 23.5 | 46.0 |
| | −60 | | | 12.8 | — |
| F6.25 | 25 | 13.0 | | 15.6 | 18.0 |
| | 40 | | | 25.6 | 48.6 |
| | −60 | | | 13.0 | — |

TABLE 15

% Area of Main Peak

| Formulation # | Storage temperature, °C | T0 | 2-weeks | 1-month | 3-months |
|---|---|---|---|---|---|
| F4.8 | 25 | 53.1 | | 51.3 | 50.1 |
| | 40 | | | 44.7 | 32.5 |
| | −60 | | | 51.3 | — |
| F5.0 | 25 | 52.1 | | 50.8 | 49.7 |
| | 40 | | | 45.5 | 34.5 |
| | −60 | | | 52.0 | — |
| F5.25 | 25 | 52.6 | | 51.8 | 50.1 |
| | 40 | | | 45.2 | 35.8 |
| | −60 | | | 52.2 | — |
| F5.5 | 25 | 52.6 | | 52.9 | 50.1 |
| | 40 | | | 45.5 | 35.2 |
| | −60 | | | 52.5 | — |
| | RT/RL | | 52.3 | 51.5 | — |
| F5.5N | 25 | 52.5 | | 51.1 | 49.4 |
| | 40 | | | 45.1 | 31.1 |
| | −60 | | | 52.2 | — |
| F5.75 | 25 | 53.4 | | 52.3 | 50.6 |
| | 40 | | | 45.3 | 35.2 |
| | −60 | | | 52.7 | — |
| F6.0 | 25 | 52.7 | | 51.4 | 49.3 |
| | 40 | | | 46.3 | 34.5 |
| | −60 | | | 52.1 | — |
| F6.25 | 25 | 52.4 | | 51.1 | 18.0 |
| | 40 | | | 45.4 | 33.5 |
| | −60 | | | 52.5 | — |

TABLE 16

% Peak Area of Basic Variants

| Formulation # | Storage temperature, ° C. | T0 | 2-weeks | 1-month | 3-months |
|---|---|---|---|---|---|
| F4.8 | 25 | 34.3 | | 34.3 | 33.5 |
| | 40 | | | 34.2 | 29.8 |
| | −60 | | | 34.5 | — |
| F5.0 | 25 | 34.5 | | 34.4 | 34.1 |
| | 40 | | | 34.0 | 27.9 |
| | −60 | | | 34.2 | — |
| F5.25 | 25 | 34.4 | | 34.5 | 33.4 |
| | 40 | | | 33.6 | 25.3 |
| | −60 | | | 34.9 | — |
| F5.5 | 25 | | | 33.8 | 33.2 |
| | 40 | 34.5 | | 32.5 | 23.4 |
| | −60 | | | 34.4 | — |
| | RT/RL | | 34.8 | 33.2 | — |
| F5.5N | 25 | 34.3 | | 34.0 | 33.2 |
| | 40 | | | 32.5 | 20.5 |
| | −60 | | | 34.4 | — |
| F5.75 | 25 | 34.2 | | 33.8 | 32.6 |
| | 40 | | | 31.6 | 21.2 |
| | −60 | | | 34.9 | — |
| F6.0 | 25 | 34.2 | | 34.2 | 32.1 |
| | 40 | | | 30.2 | 19.4 |
| | −60 | | | 35.0 | — |
| F6.25 | 25 | 34.6 | | 33.3 | 31.8 |
| | 40 | | | 29.0 | 17.9 |
| | −60 | | | 34.5 | — |

Overall Stability Profile

There was not much change in appearance, pH, protein concentration, purity, charge and size variant distribution for the drug product between pH 4.80 to 6.25 during 3-month exposure at −60° C. and 25° C., indicating that the product is relatively stable under the current specification of pH 5.5±0.5 and at intended storage temperature of 2-8° C. High temperature exposure at 40° C. did not significantly change appearance, pH, protein concentration, and purity, but provided a strong signal of formation of size and charge-related degradants in the formulations at the stressed condition. The signal of size and charge-related change can be used to establish an overall pH stability profile and to select an optimal formulation pH value. FIG. 1 shows the percent degradants of these two major groups in the samples with different pH values at 40° C. From the figure, an X-shaped profile is identified with the curves intersecting at ~pH 5.5. The profile curves clearly show that the size-related degradants (HMWs and LMWs) increased with decreasing pH whereas charge-related degradants (iCIEF acidic species) increased with increasing pH. The pH value of ~5.5 is the cross point and will minimize the possibility for the drug product to be out of specifications established either by iCIEF or SEC.

Figure 2:
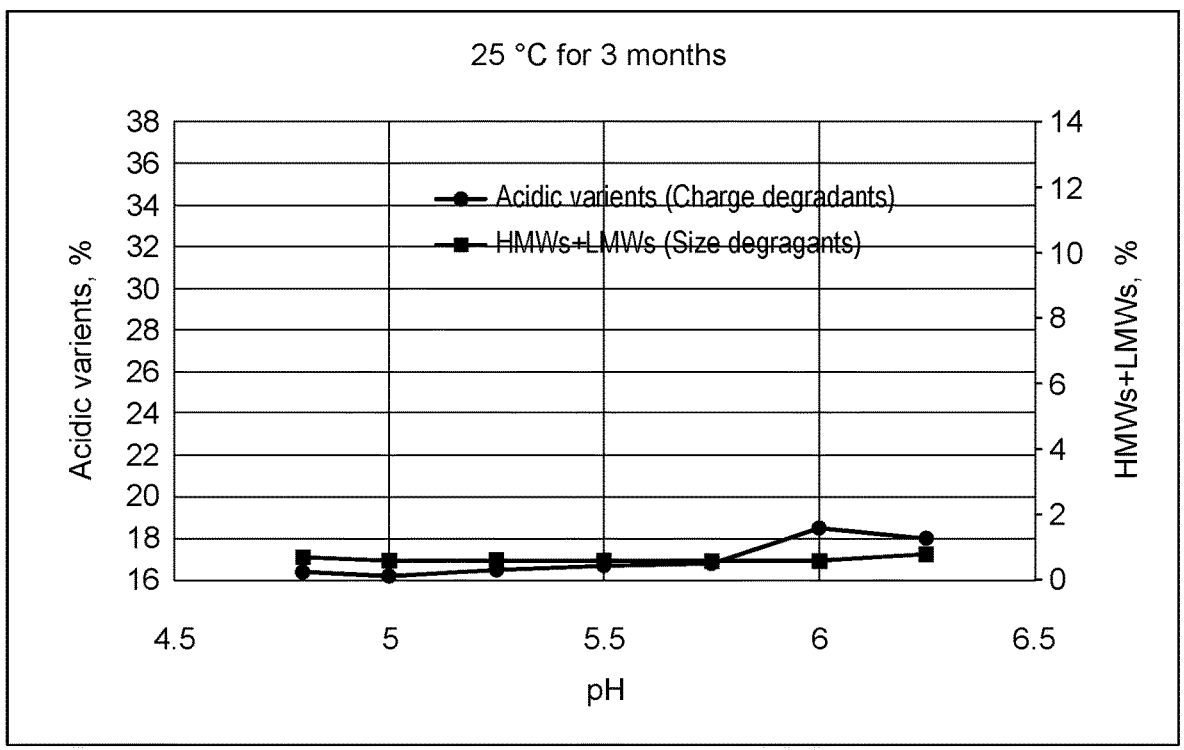
FIG. 2 shows the relationship of charge-related and size-related degradants with pH for an anti-LAG-3 antibody composition of the invention stored at 25° C. for 3 months.

At lower temperature of 25° C., the differences were not as strong between pH values for these two types of degradants although there appears a similar trend as that at 40° C. (FIG. 2). As no or very little degradation occurred over 3 months at 25° C., significantly longer period of exposure at 25° C. is likely required to show the similar pH-stability profile observed at 40° C.

Figure 3A:
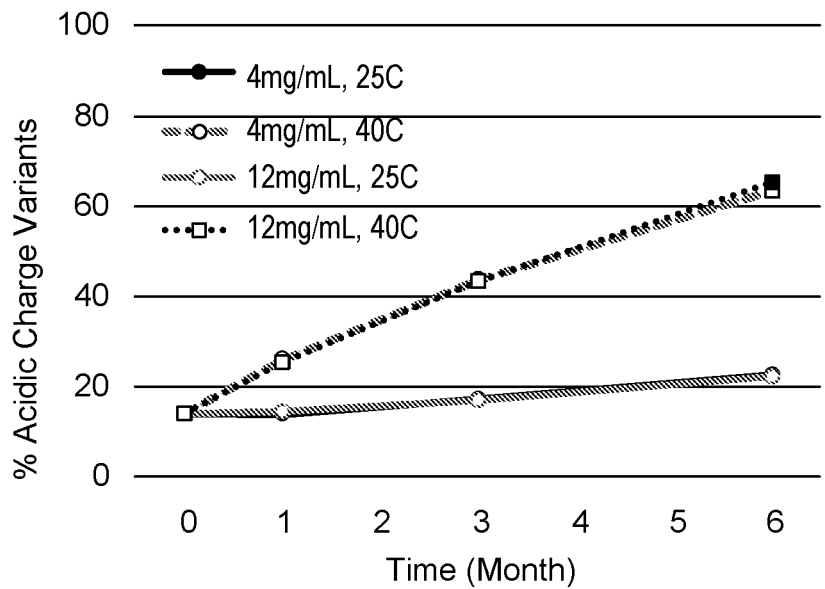
FIGS. 3A-3B show varying the concentration of anti-LAG-3 antibody in compositions of the invention did not affect the percentage of acidic charge variants during storage at 5° C., 25° C. or 40° C. for 1-6 months.
Figure 3B:
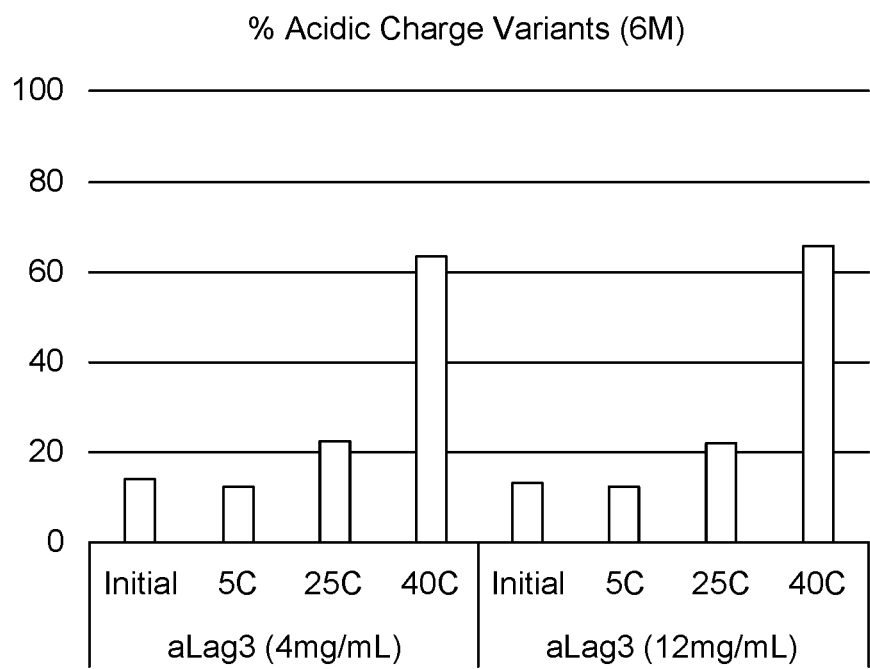

Furthermore, varying the concentration of anti-LAG-3 antibody (4 mg/ml versus 12 mg/ml) did not change the percentage of acidic charge variants during storage at 5° C., 25° C., or 40° C. for 1-6 months (FIGS. 3A and 3B).

Light Impact on Drug Product Stability

Figure 4:
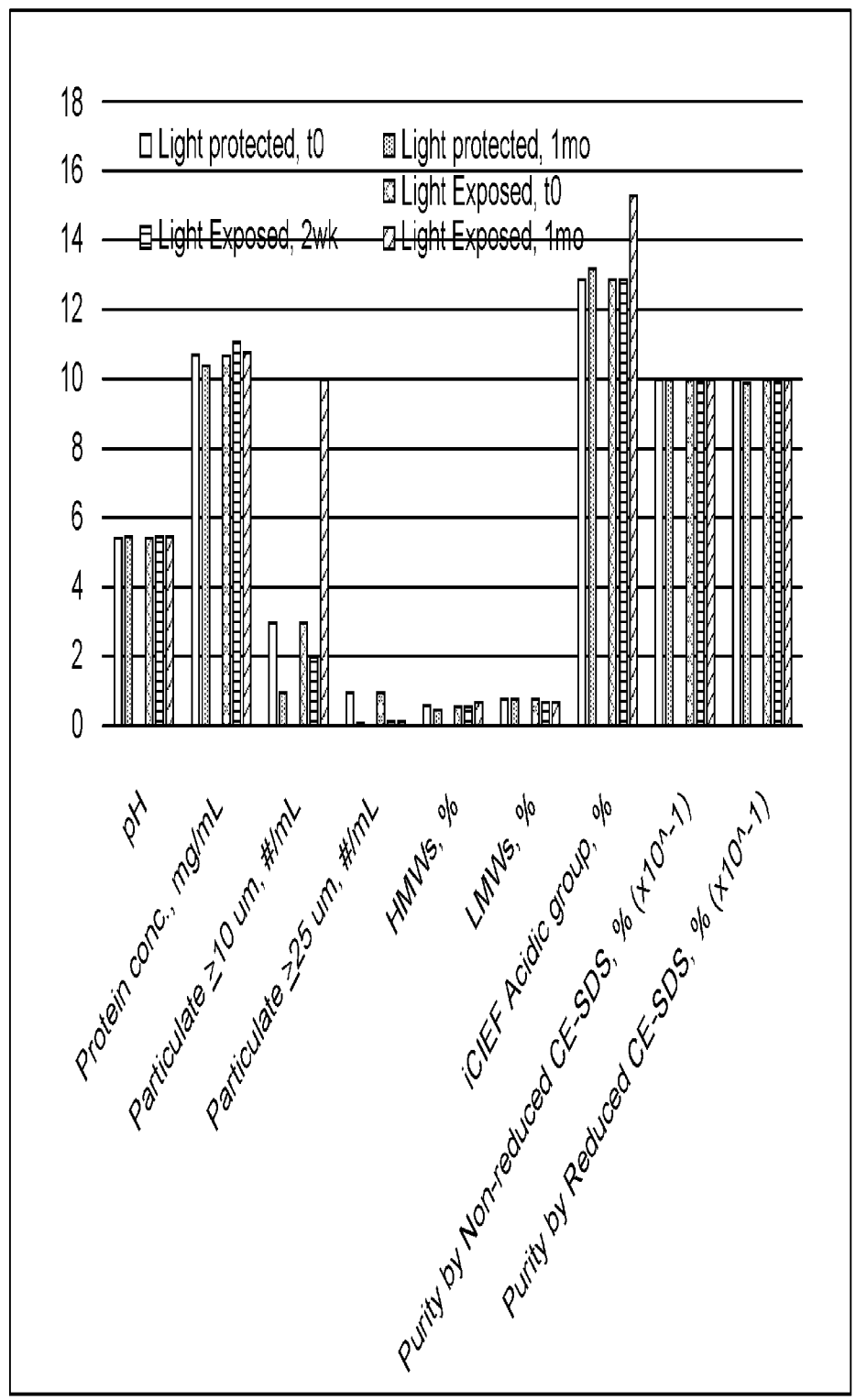
FIG. 4 shows the pH, particulate count, high molecular weight aggregates (HMWs), low molecular weight aggregates (LMWs), acidic peaks, and purity under light exposed and light protected conditions for an anti-LAG-3 antibody composition of the invention.

The effect of room temperature/room lighting (RT/RL) is shown in FIG. 4. There is essentially no difference between light-exposed and light-protected samples in appearance, pH, protein concentration, purity, HMWs and LMWs for the exposure period (up to 1 month). The particulate count for both samples is also very low and all within the limits established by USP. There is no increase of iCIEF acidic peak area after 2-week exposure to room light, and a very slight increase (~2%) is shown at 1-month time point. This increase could be due to either analytical method variation or a real trend of light-induced reaction. However, there should be no significant impact on the drug product quality as the change in acidic species is relatively minor (<3%). Based on the above comparison between light-exposed and light-protected samples, it is concluded that there will be sufficient stability for the drug product under room light for up to 4 weeks.

Impact of DTPA on Drug Product Stability

Figure 5:
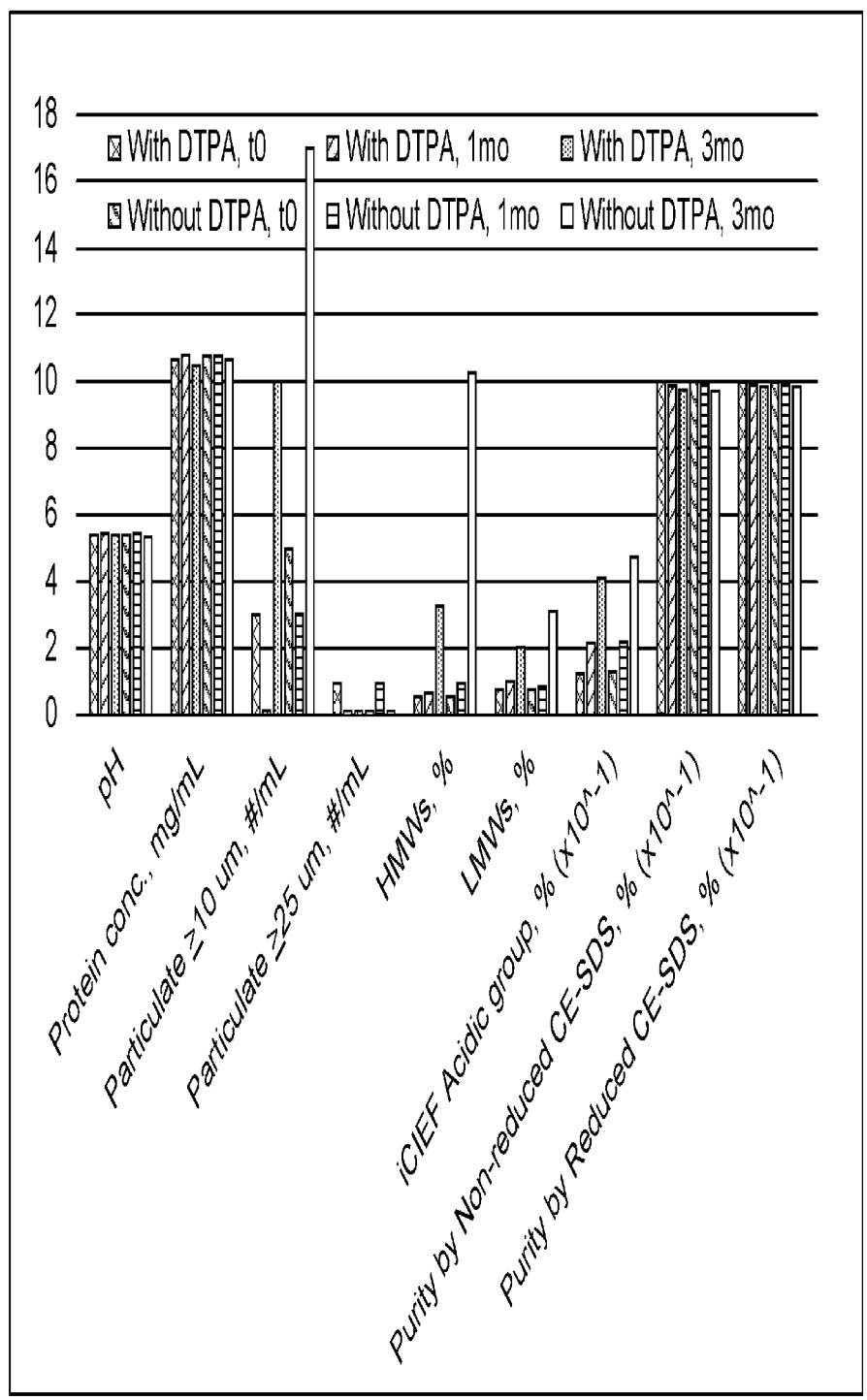
FIG. 5 shows the pH, particulate count, HMWs, LMWs, acidic peaks, and purity of anti-LAG-3 antibody compositions of the invention with DTPA and without DTPA stored at 40° C. for 1 or 3 months.
Figure 6:
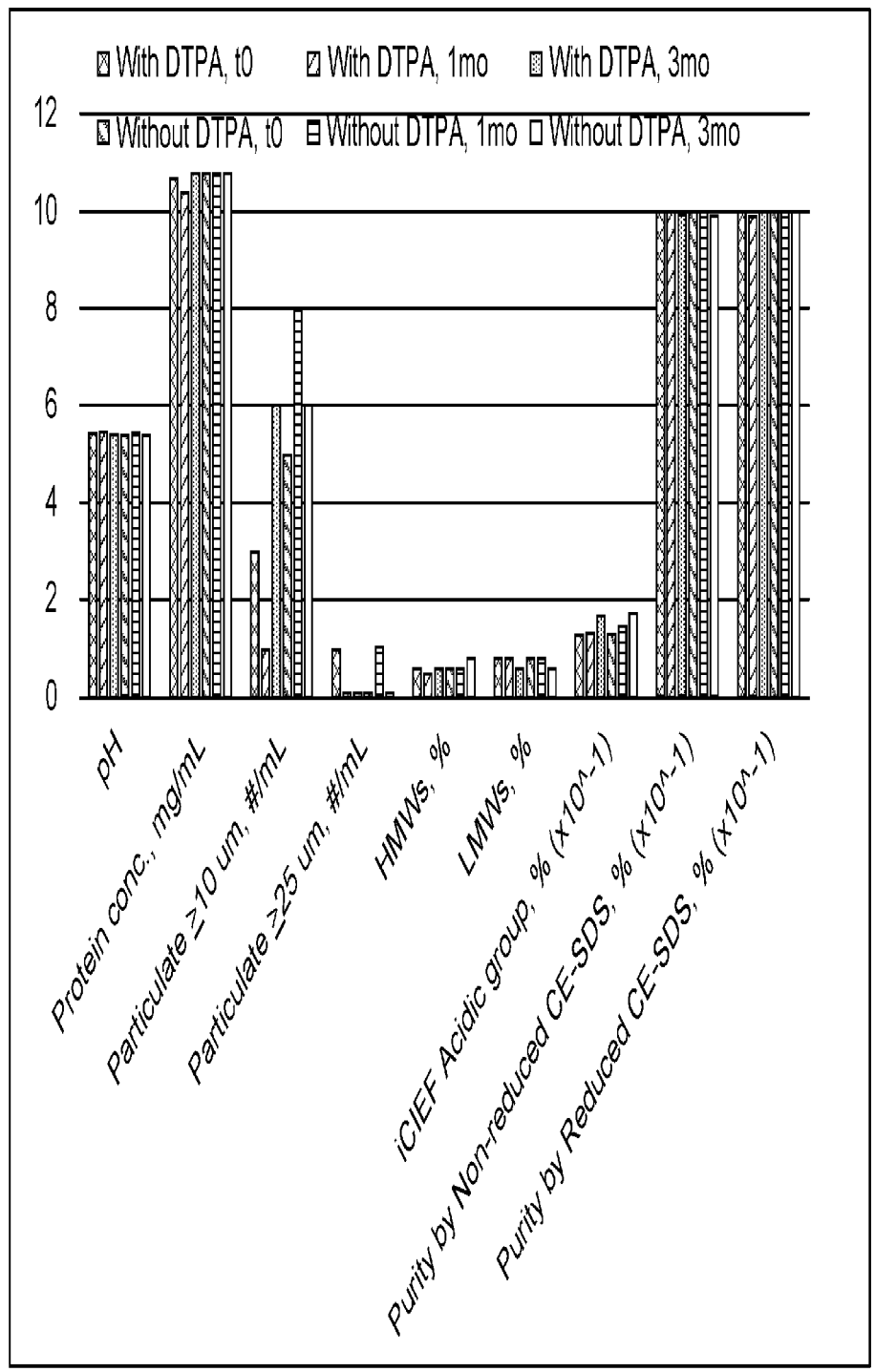
FIG. 6 shows the pH, particulate count, HMWs, LMWs, acidic peaks, and purity of an anti-LAG-3 antibody composition of the invention with DTPA and without DTPA stored at 25° C. for 1 or 3 months.

The effect of DTPA on the DP stability is shown in FIG. 5. The appearance, pH, protein concentration, and purity of samples containing DTPA were similar to samples without DTPA following storage for up to 3 months at 40° C. The particulate counts for all samples were also low and within USP limits. However, there was a more significant difference in BMW and LMW species levels between DTPA and non-DTPA samples with temperature stress. Although HMW and LMW species increased with time in all samples stored at 40° C., they increased at a slower rate in the samples containing DTPA. There was no difference in iCIEF acidic peak area after 1-month exposure at 40° C., but an approximately 6% difference was observed at the 3-month time point. Therefore, addition of DTPA reduced the formation of both size and charge-related degradants.

The comparison between DTPA and non-DTPA samples at 25° C. is shown in FIG. 5. No significant differences in appearance, pH, protein concentration, particulate count, HMWs, LMWs, acidic variants and purity were observed in any of the samples. Since no or minimal degradation was apparent at 25° C. at the 3-month timepoint, it is difficult to assess the impact of DTPA at this temperature. Much longer exposure times will likely be required to provide a clear understanding of the difference between DTPA and non-DTPA samples. The available stability data at 25° C. indicate that the drug product would be relatively stable at the intended storage temperature of 2-8° C. for long-term storage even without DTPA.

However, addition of DTPA into drug product formulation is expected to further increase stability and provide additional product ruggedness under potential temperature or light excursion conditions that may be encountered during manufacture, distribution and administration. A similar study with EDTA was also conducted and the results were similar (data not shown).

Conclusions

No significant stability issues were observed for pH, particulate count, protein concentration, purity, charge variants and aggregation at 25° C. for three months, indicating the drug product will be relatively stable for the intended long-term product storage condition at 2-8° C. within pH 5-6. It is found that pH is a major contributor to influence the stability at elevated temperature of 40° C. An X shaped pH-stability profile was observed when overlaying two major degradation product groups: charge (iCIEF acidic group) and size-related (HMWs and LMWs) variants. Charge variant formulation increased with increasing pH values, while size variants decreased with increasing pH values. The pH stability curves intersected at ~pH 5.5, indicating optimal stability at this pH.

In addition, no significant difference in stability was noted between light-exposed and light-protected samples for a period of one month, which supports manufacture, storage, distribution and administration of the drug product under short-term room light conditions.

Addition of DTPA increased the stability for the drug product based on the data obtained at 40° C. It is expected that DTPA or EDTA would further increase the shelf life of the drug product significantly when stored at 2-8° C.

Example 3

The effect of chelators on aggregation in compositions of the invention was tested further. Compositions containing anti-LAG-3 antibody alone (aLAG-3 Mono) or anti-LAG-3 antibody and anti-PD-1 antibody at a 1:1 fixed dose ratio combination (aLAG-3 FDRC) were prepared as described in the other Examples. The final 1:1 aLAG-3 FDRC composition contained 12 mg/ml anti-LAG-3 antibody, 12 mg/ml nivolumab, 20 mM histidine, 250 mM sucrose, and 0.05% (w/v) polysorbate 80 (PS80).

Compositions also contained 20 µM-100 µM DTPA or 20 µM-250 µM EDTA, and were spiked with 1-5 ppm metals to induce aggregation (total 1 ppm or 5 ppm with 200 ppb or 1,000 ppb of Fe, Ni, Cr, Cu and Zn, respectively). Compositions were stored at 40° C. or room temperature (RT/RL) for one month and HMW aggregates were measured as explained in Example 2.

Figure 7:
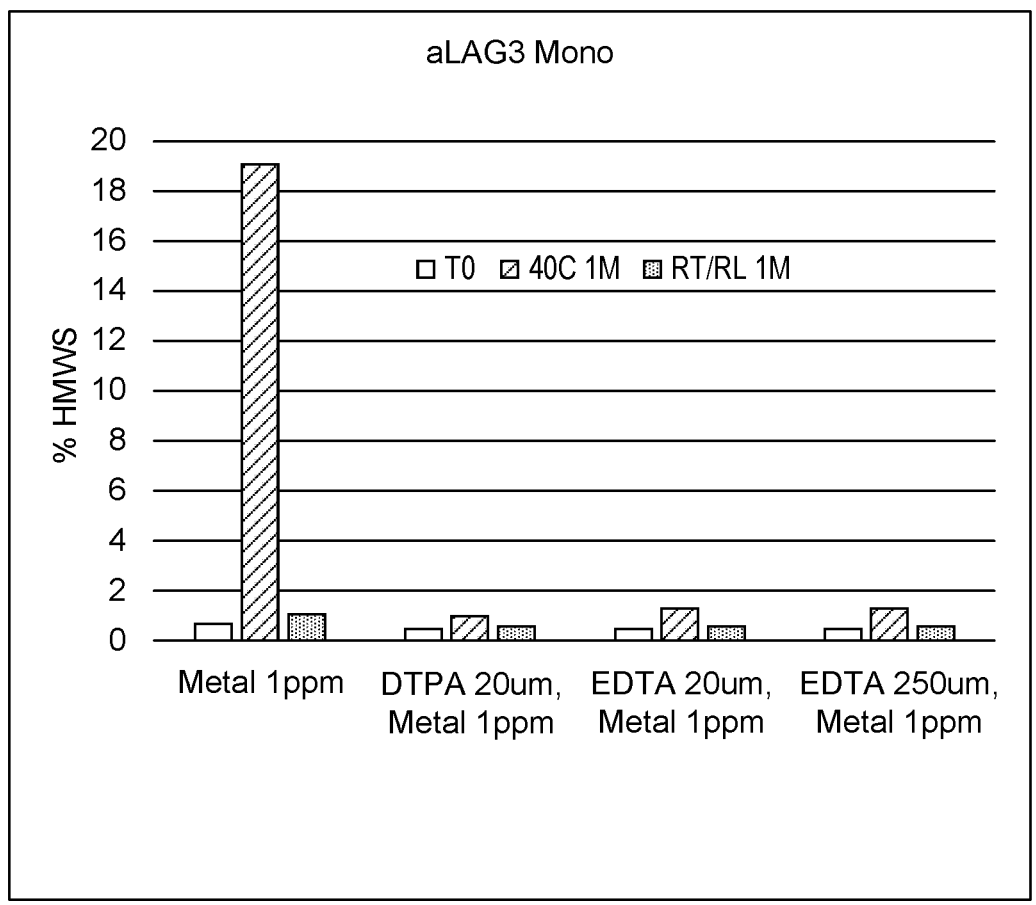
FIG. 7 shows the percentage of HMWs induced with metals in an anti-LAG-3 composition of the invention containing DTPA or EDTA which was stored at 40° C. or room temperature for 1 month.
Figure 8:
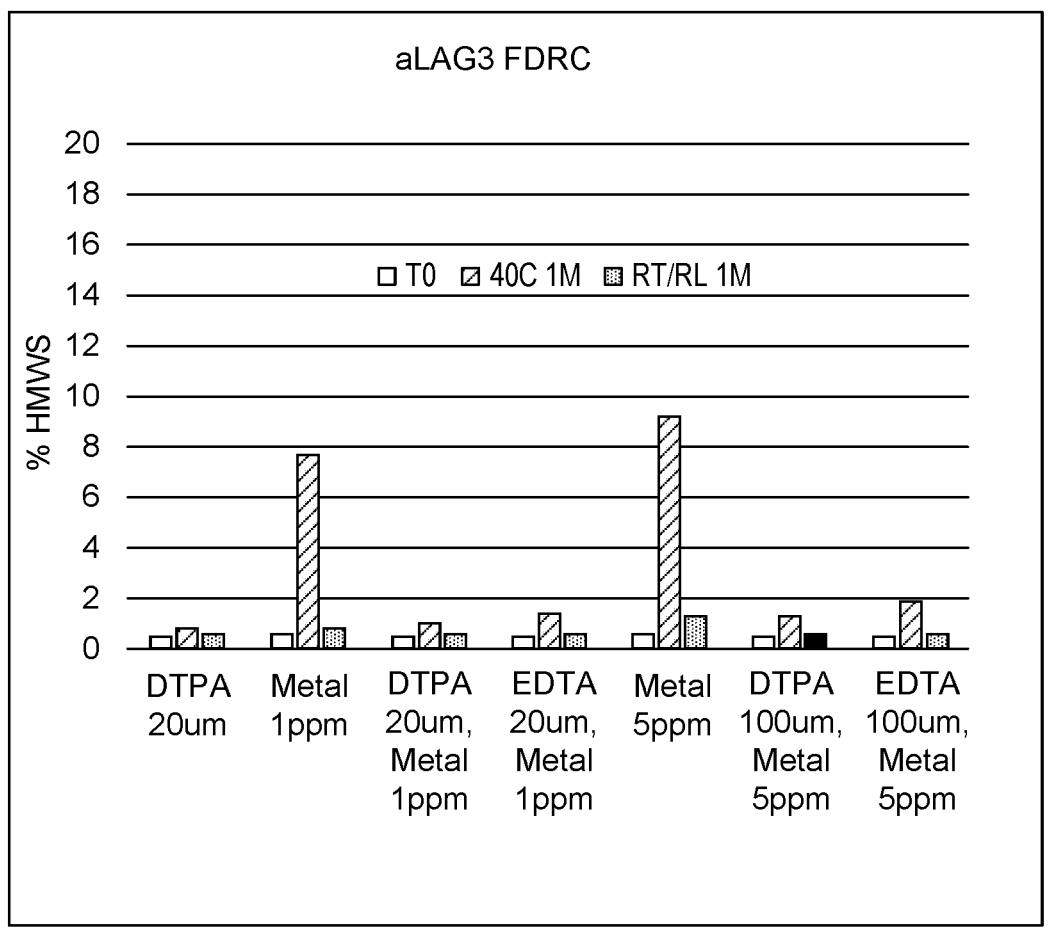
FIG. 8 shows the percentage of HMWs induced with metals in a 1:1 (anti-LAG-3 antibody:anti-PD-1 antibody) fixed dose ratio combination (FDRC) of the invention containing DTPA or EDTA which was stored at 40° C. or room temperature for 1 month.

The percentage of HMW aggregates for the aLAG-3 Mono and aLAG-3 FDRC compositions is shown in FIGS. 7 and 8, respectively. The presence of metals caused significant aggregation at 40° C. in the absence of chelator for both aLAG-3 Mono and FDRC but was more pronounced in the aLAG3 Mono composition. However, both DTPA and EDTA effectively reduced metal-induced aggregation at 40° C. or RT/RL.

Example 4

The stability performance of a 1:3 fixed dose ratio combination of the invention was tested. Compositions containing anti-LAG-3 antibody and anti-PD-1 antibody at a 1:3 fixed dose ratio combination (1:3 FDRC) and DTPA were prepared as described in the other Examples with the final composition containing 12 mg/ml of nivolumab (Nivo), 4 mg/ml of anti-LAG-3 antibody. Compositions containing anti-LAG-3 antibody without anti-PD-1 antibody and anti-PD-1 antibody without anti-LAG-3 antibody were also tested for comparison. Compositions were stored at −60° C., 5° C., 25° C., or 40° C. for 3 months and the charge distribution change of formulation samples was measured by iCIEF as explained in Example 2.

Figure 9A:
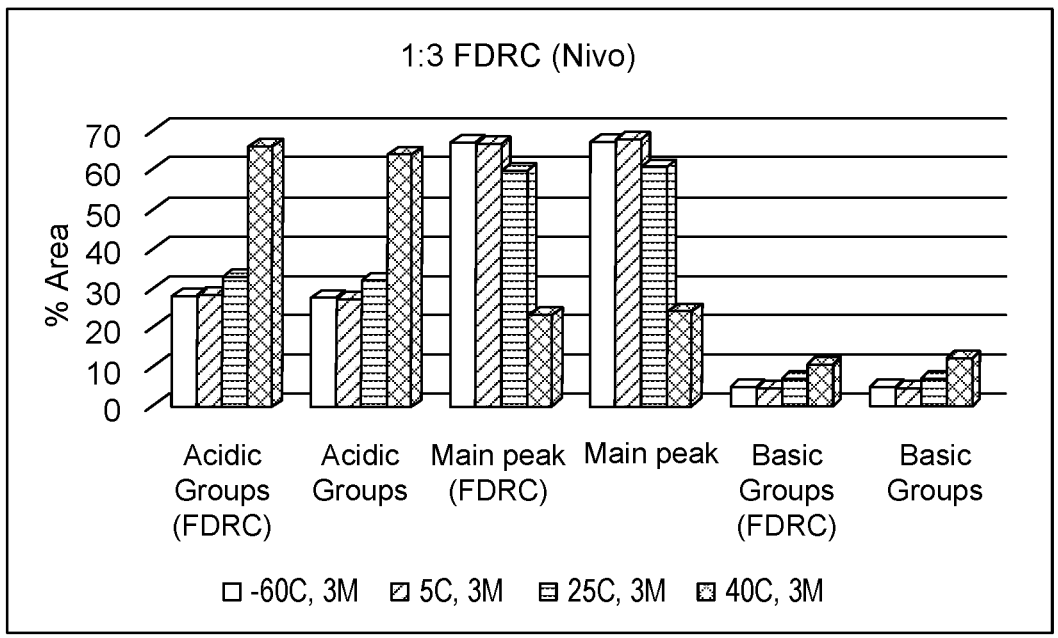
FIGS. 9A-9B show iCIEF stability patterns for anti-PD-1 (FIG. 9A) and anti-LAG-3 (FIG. 9B) in a 1:3 (anti-LAG-3 antibody:anti-PD-1 antibody) FDRC composition of the invention are similar to those for anti-PD-1 or anti-LAG-3 alone in the same buffer system.
Figure 9B:
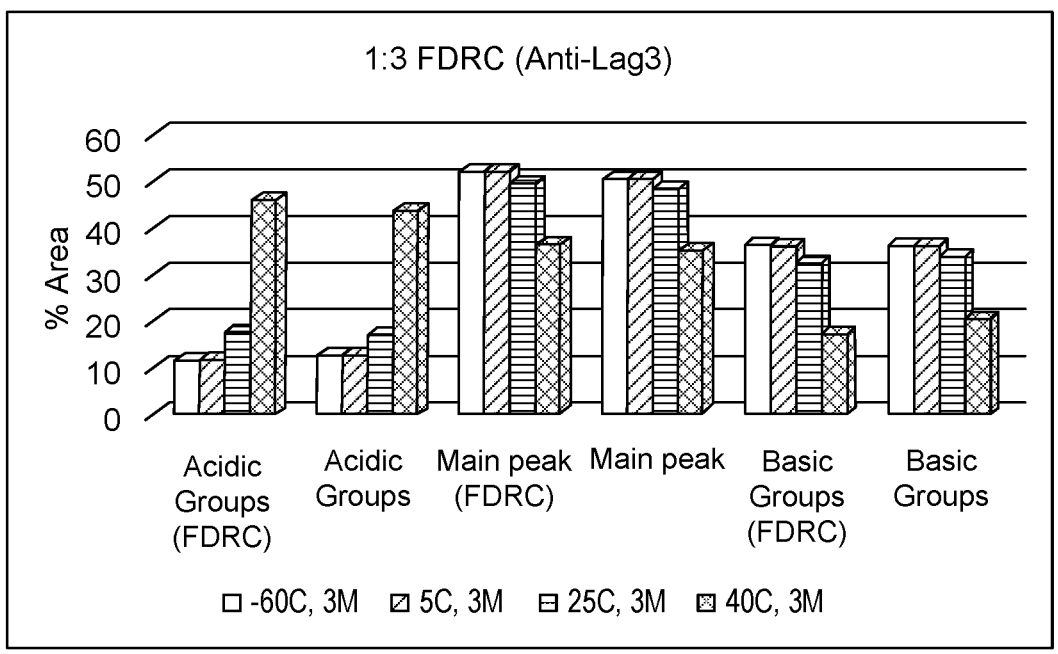

The iCIEF results for anti-PD-1 antibody (FIG. 9A) and anti-LAG-3 antibody (FIG. 9B) show stability patterns for both antibodies in 1:3 FDRC that are similar to those for anti-PD-1 antibody or anti-LAG-3 antibody alone in the same buffer system.

Example 5

The 12-month stability performance of fixed dose ratio combinations (FDRCs) of the invention was also tested. Compositions containing anti-PD-1 antibody and anti-LAG-3 antibody at 3:1 and 1:1 FDRC with DTPA were prepared as described in the other Examples. Compositions containing anti-LAG-3 antibody without anti-PD-1 antibody (nivolumab, Nivo) were also tested for comparison. Compositions were stored at 5° C. or 25° C. for 1, 3, 6 and 12 months and the percentage of HMWs was measured by SEC and the charge distribution change was measured by iCIEF as explained in Example 2.

Figure 10A:
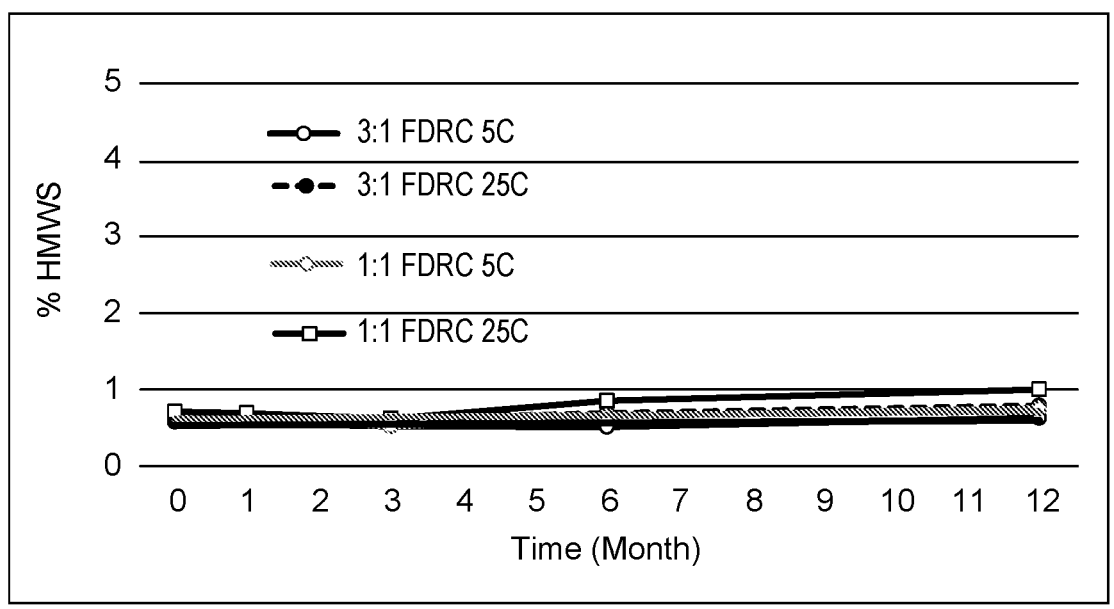
FIGS. 10A-10C show the 12-month stability performance of 3:1 and 1:1 (anti-PD-1 antibody:anti-LAG-3 antibody) FDRC compositions of the invention. No significant HWM aggregation was observed with the 3:1 or 1:1 (anti-PD-1 antibody:anti-LAG-3 antibody) FDRC compositions (FIG. 10A). Also, no significant charge change was observed for the 3:1 or 1:1 (anti-PD-1 antibody:anti-LAG-3 antibody) FDRC formulations at 5° C., and similar, or improved stability patterns were observed at 25° C.
Figure 10B:
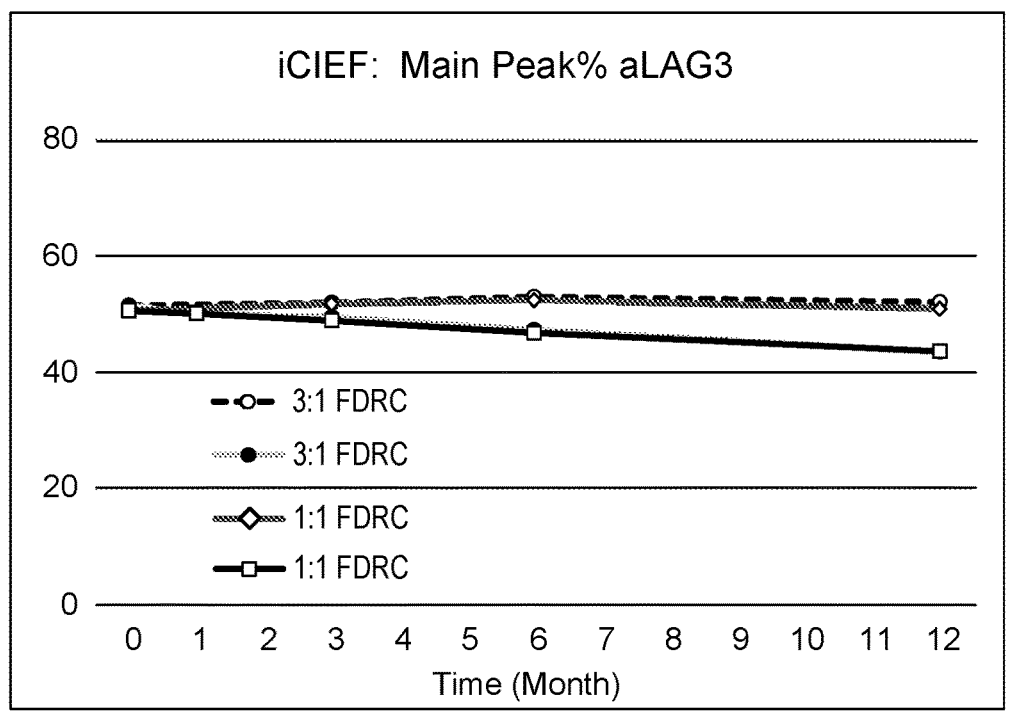
Figure 10C:
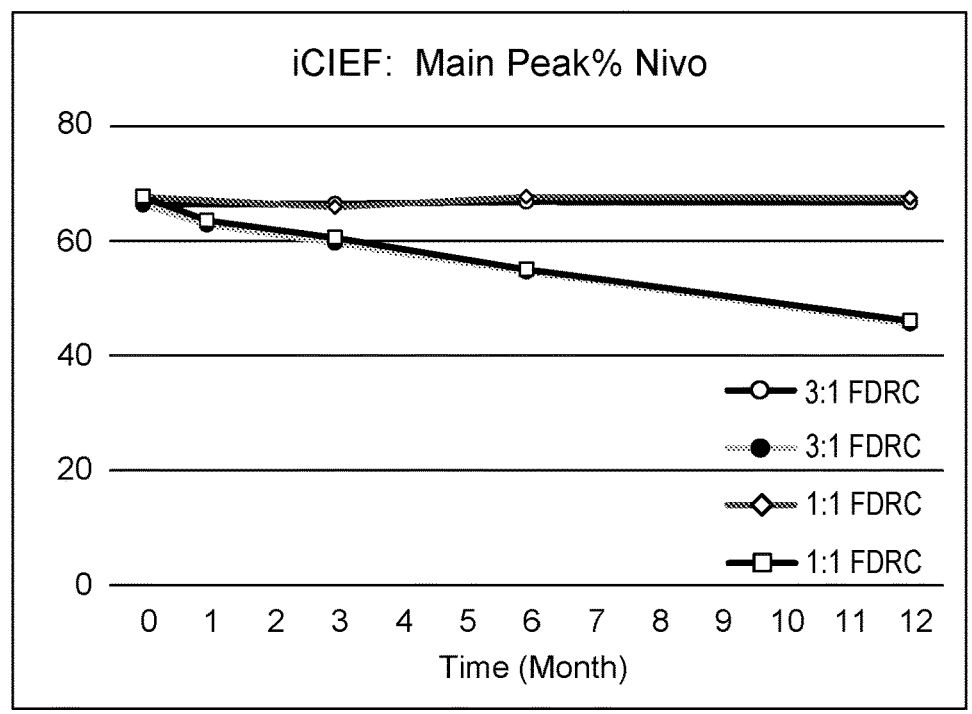

No significant aggregation was observed with either the 3:1 or 1:1 FDRC formulations (FIG. 10A). Also, no significant charge change was observed for the 3:1 or 1:1 FDRC formulations at 5° C., and similar, or improved stability patterns were observed at 25° C. (FIGS. 10B and 10C). Additional stability measurements are reported in Tables 17 and 18. In particular, Table 17 shows that 3:1 and 1:1 (anti-PD-1 antibody:anti-LAG-3 antibody) FDRC formulations exhibited essentially no change in total protein concentration or pH after 3 months under accelerated and/or stress temperature/lighting conditions.

TABLE 17

| Time | Storage Condition | 3:1 FDRC (240 N:80 aL3) | | 1:1 FDRC (240 N:240 aL3) | |
|---|---|---|---|---|---|
| | | pH | A280, mg/mL | pH | A280, mg/mL |
| Initial | | 5.83 | 15.1 | 5.83 | 22.3 |
| 1 Month | −60° C. | 5.84 | 15.9 | 5.81 | 23.4 |
| | 25° C. | 5.79 | 15.8 | 5.84 | 23.3 |
| | 40° C. | 5.79 | 15.7 | 5.79 | 23.6 |
| | RT/RL | 5.82 | 15.6 | 5.83 | 23.5 |
| 3 Months | −60° C. | 5.81 | 15.7 | 5.82 | 23.6 |
| | 5° C. | 5.81 | 15.9 | 5.80 | 23.5 |
| | 25° C. | 5.77 | 15.8 | 5.73 | 23.4 |
| | 40° C. | 5.83 | 16.0 | 5.83 | 24.0 |
| | RT/RL | 5.72 | 15.6 | 5.72 | 23.4 |

TABLE 18

| Test item | | | T0 | −60 C. | 5 C. | 25 C. | RT/ RL | 40 C. |
|---|---|---|---|---|---|---|---|---|
| Particulate (HIAC), #/mL | | ≥2 um | 18 | 66 | 86 | 90 | 291 | 673 |
| | | ≥10 um | 8 | 3 | 5 | 5 | 25 | 6 |
| | | ≥25 um | 0 | 0 | 0 | 0 | 1 | 0 |
| SEC | | HMWs, % | 0.6 | 0.5 | 0.5 | 0.6 | 1.8 | 2.0 |
| | | Monomer, % | 99.4 | 98.8 | 98.7 | 98.6 | 97.0 | 96.6 |
| | | LMWs, % | 0.1 | 0.7 | 0.7 | 0.8 | 1.2 | 0.8 |
| ICIEF | aLAG3 | Acidic, % | 13.8 | 11.6 | 11.9 | 17.8 | 28.3 | 46.0 |
| | | Main, % | 51.5 | 52.0 | 52.0 | 49.6 | 46.2 | 36.5 |
| | | Basic, % | 34.7 | 36.4 | 36.1 | 32.6 | 25.5 | 17.5 |
| | Nivo | Acidic, % | 28.3 | 28.0 | 28.3 | 32.9 | 36.8 | 65.9 |
| | | Main, % | 66.7 | 67.0 | 66.9 | 60.0 | 56.7 | 23.2 |
| | | Basic, % | 5.0 | 5.0 | 4.8 | 7.1 | 6.5 | 10.9 |
| CE-SDS, NR | | Purity, % | 99.4 | 99.7 | 99.7 | 99.5 | 99 | 95.3 |
| RP-HPLC | | Lag3/Nivo Ratio | 2.64 | 2.63 | 2.65 | 2.64 | 2.65 | 2.60 |

Example 6

Stability performance of FDRC compositions was also assessed by measuring oxidation and deamidation. Compositions containing anti-PD-1 antibody and anti-LAG-3 antibody at 1:3 and 1:1 (anti-LAG-3 antibody:anti-PD-1 antibody) FDRC were prepared as described in the other Examples. Compositions were stored at 40° C. for 3 months and a tryptic peptide mapping assay was performed to measure deamidation and oxidation. Specifically, samples were reduced, alkylated and digested with trypsin. The tryptic peptides were separated on a C-18 column and detected by a UV detector at 215 and 280 nm, followed by a mass spectrometer (LTQ-Orbitrap-Elite). Relative quantitation was achieved by comparing peak areas of the intact peptides as well as the modified peptides in selected ion chromatograms.

Figure 11A:
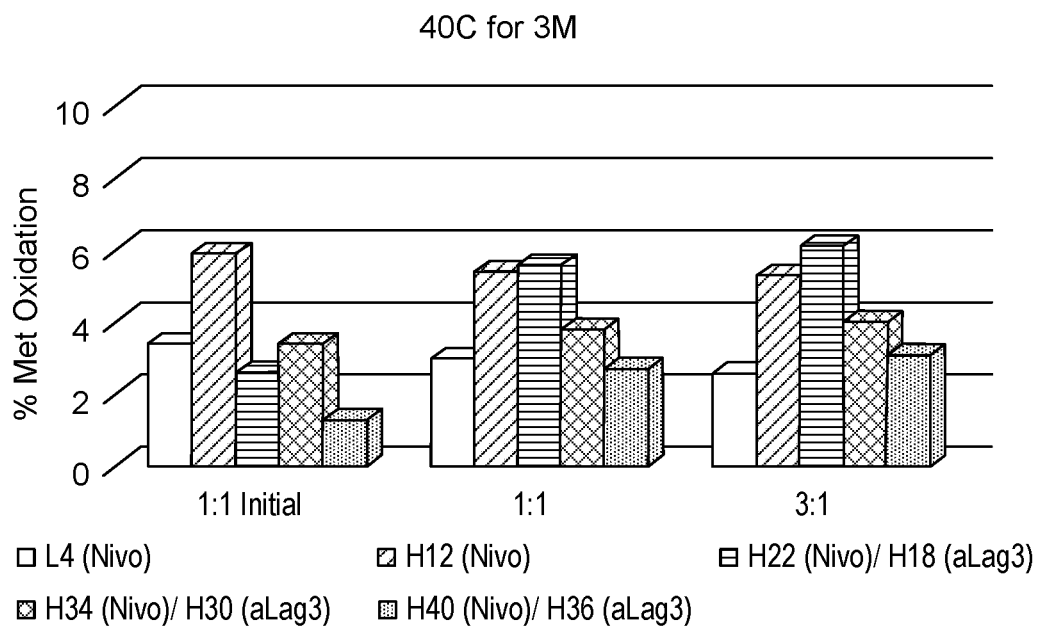
FIGS. 11A-11C show the stability performance of 1:3 and 1:1 (anti-LAG-3 antibody:anti-PD-1 antibody) FDRC compositions assessed by measuring protein oxidation and deamidation. No significant oxidation of methionine (Met) or tryptophan (Trp) oxidation was observed in the compositions (FIGS. 11A and 11B, respectively). In addition, only a relatively small increase in deamination was observed in the compositions (FIG. 11C).
Figure 11B:
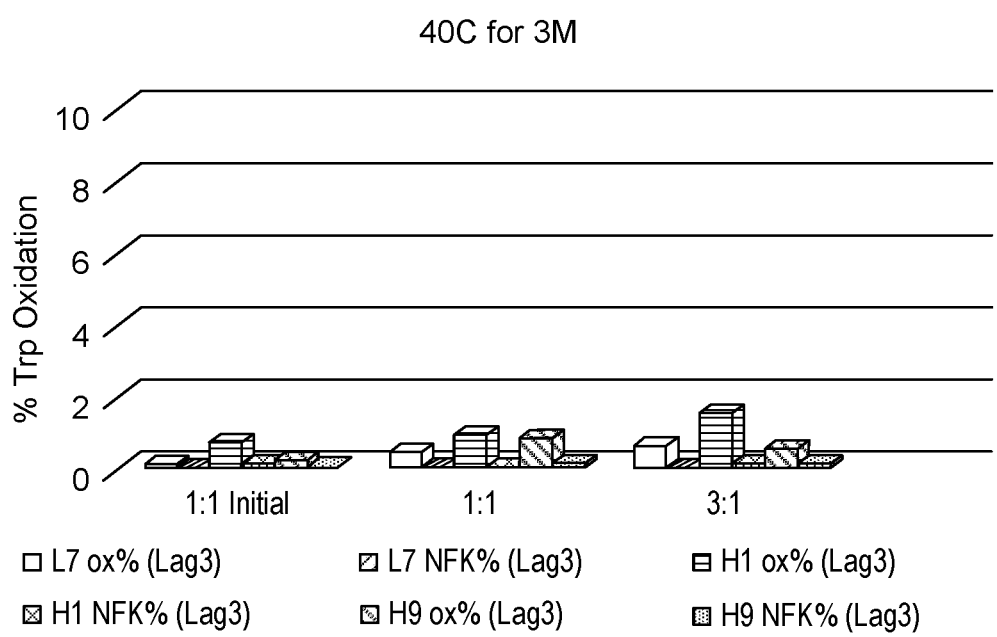
Figure 11C:
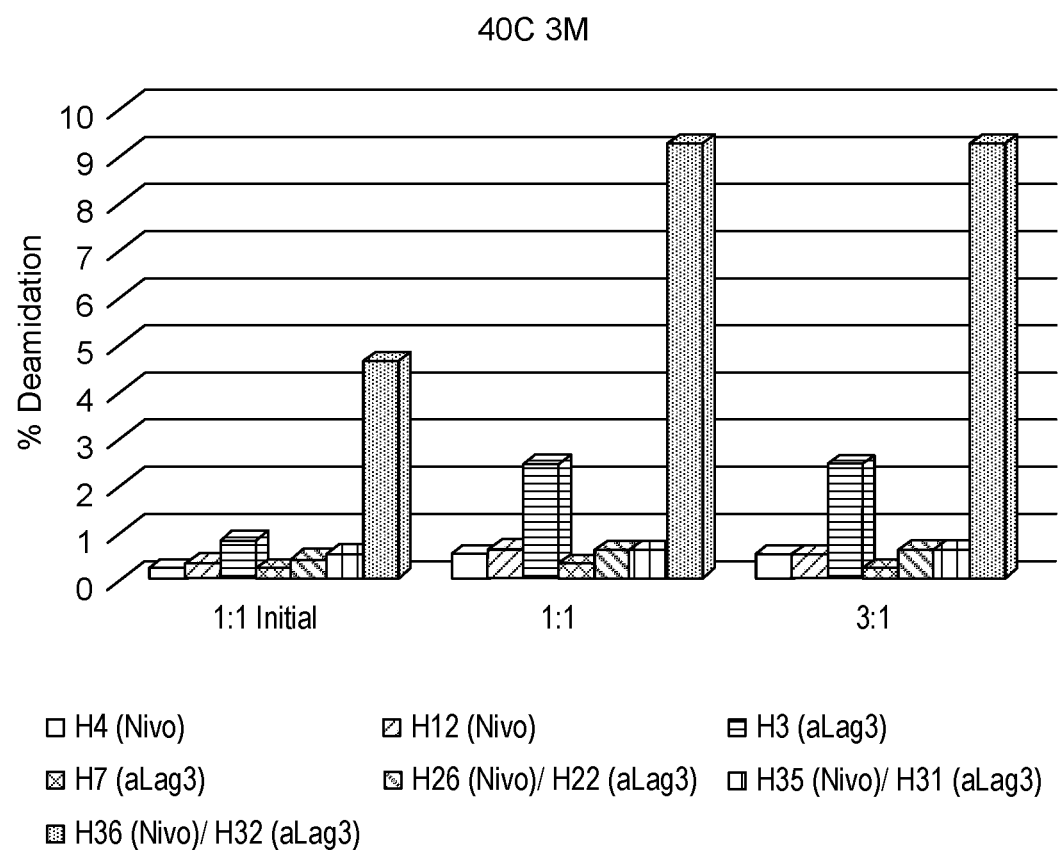

The results of the assay are shown in FIGS. 11A-11C. No significant oxidation of methionine (Met) or tryptophan (Trp) oxidation was observed in the formulations (FIGS. 11A and 11B, respectively). In addition, only a relatively small increase in deamidation was observed in the formulations (FIG. 11C).

Example 7

A nivolumab/Anti-LAG-3 antibody FDRC was prepared from nivolumab drug product and an anti-LAG-3 TEST drug product for FDRC feasibility at early drug development stage. Nivolumab drug product is an aqueous solution containing 10 mg/mL nivolumab in 20 mM sodium citrate, 50 mM sodium chloride, 3.0% (w/v) mannitol, 20 µM pentetic acid, 0.04% (w/v) polysorbate 80 at pH 6.0. Anti-LAG-3 TEST drug product is an aqueous solution containing 10 mg/mL anti-LAG-3 antibody in 10 mM sodium citrate, 10 mM sodium phosphate, 150 mM sodium chloride, 0.05% (w/v) polysorbate 80 at pH 5.5.

The Nivolumab/Anti-LAG-3 FDRC (1:1) drug product was formulated by combining the respective drug products at a ratio of 1 nivolumab molecule per 1 anti-LAG-3 molecule. Development stability data for up to 3 months shows the FDRC drug product was stable when stored at 2° C. to 8° C. The FDRC drug product has a total protein concentration of 10 mg/mL. The composition of the FDRC is provided in Table 19. Stability was assessed by visual appearance, SE-HPLC, iCIEF, and SDS-PAGE (NR/R) using methods described in the Examples.

TABLE 19

Formulation Composition of Nivolumab-Anti-LAG-3 1:1 FDRC DP

| Component | Function | FDRC | Unit |
|---|---|---|---|
| Nivolumab (BMS-936558) | Active ingredient | 5 | mg/mL |
| Anti-LAG-3 (BMS-986016) | Active ingredient | 5 | mg/mL |
| Sodium Phosphate Dibasic Heptahydrate | Buffering agent | 0.2 | mM |
| Sodium Phosphate Monobasic Monohydrate | Buffering agent | 4.8 | mM |
| Sodium Citrate, Dihydrate | Buffering agent | 15 | mM |
| Sodium Chloride | Tonicity modifier | 100 | mM |
| Mannitol | Tonicity modifier | 1.5 | % (w/v) |
| Pentetic Acid | Metal ion chelator | 10 | µM |
| Polysorbate 80 | Surfactant | 0.035 | % (w/v) |
| pH at 20° to 25° C. | pH adjustment | 5.75 | pH unit |

What is claimed is:

1. A pharmaceutical composition comprising:
(a) about 80 mg of an anti-LAG-3 antibody or antigen binding fragment thereof comprising CDR1, CDR2, and CDR3 domains of the heavy chain variable region having the sequence set forth in SEQ ID NO:3, and CDR1, CDR2, and CDR3 domains of the light chain variable region having the sequence set forth in SEQ ID NO:5;
(b) about 240 mg of an anti-PD-1 antibody or antigen binding fragment thereof comprising CDR1, CDR2, and CDR3 domains of the heavy chain variable region having the sequence set forth in SEQ ID NO:19, and CDR1, CDR2, and CDR3 domains of the light chain variable region having the sequence set forth in SEQ ID NO:21;
(c) about 20 mM of histidine buffer;
(d) about 250 mM of sucrose;
(e) about 20 µM of DTPA; and
(f) about 0.05% (w/v) of polysorbate 80;
wherein the pharmaceutical composition has a pH of about 5.8.

2. The pharmaceutical composition of claim 1, wherein the anti-LAG-3 antibody or antigen binding fragment thereof comprises heavy chain variable region CDR1, CDR2, and CDR3 domains comprising the sequences set forth in SEQ ID NOs:7, 8, and 9, respectively, and light chain variable region CDR1, CDR2, and CDR3 domains comprising the sequences set forth in SEQ ID NOs:10, 11, and 12, respectively.

3. The pharmaceutical composition of claim 1, wherein the anti-PD-1 antibody or antigen binding fragment thereof comprises heavy chain variable region CDR1, CDR2, and CDR3 domains comprising the sequences set forth in SEQ ID NOs:23, 24, and 25, respectively, and light chain variable region CDR1, CDR2, and CDR3 domains comprising the sequences set forth in SEQ ID NOs:26, 27, and 28, respectively.

4. The pharmaceutical composition of claim 1, wherein the anti-LAG-3 antibody or antigen binding fragment thereof comprises heavy chain variable region CDR1, CDR2, and CDR3 domains comprising the sequences set forth in SEQ ID NOs:7, 8, and 9, respectively, and light chain variable region CDR1, CDR2, and CDR3 domains comprising the sequences set forth in SEQ ID NOs:10, 11, and 12, respectively, and the anti-PD-1 antibody or antigen binding fragment thereof comprises heavy chain variable region CDR1, CDR2, and CDR3 domains comprising the sequences set forth in SEQ ID NOs:23, 24, and 25, respectively, and light chain variable region CDR1, CDR2, and CDR3 domains comprising the sequences set forth in SEQ ID NOs:26, 27, and 28, respectively.

5. The pharmaceutical composition of claim 1, wherein the anti-LAG-3 antibody or antigen binding fragment thereof comprises heavy and light chain variable regions comprising the sequences set forth in SEQ ID NOs:3 and 5, respectively.

6. The pharmaceutical composition of claim 1, wherein the anti-PD-1 antibody or antigen binding fragment thereof comprises heavy and light chain variable regions comprising the sequences set forth in SEQ ID NOs:19 and 21, respectively.

7. The pharmaceutical composition of claim 1, wherein the anti-LAG-3 antibody or antigen binding fragment thereof comprises heavy and light chain variable regions comprising the sequences set forth in SEQ ID NOs:3 and 5, respectively, and the anti-PD-1 antibody or antigen binding fragment thereof comprises heavy and light chain variable regions comprising the sequences set forth in SEQ ID NOs:19 and 21, respectively.

8. The pharmaceutical composition of claim 1, wherein the anti-LAG-3 antibody comprises heavy and light chains comprising the sequences set forth in SEQ ID NOs:1 and 2, respectively.

9. The pharmaceutical composition of claim 1, wherein the anti-PD-1 antibody comprises heavy and light chains comprising the sequences as set forth in SEQ ID NOs:17 and 18, respectively.

10. The pharmaceutical composition of claim 1, wherein the anti-LAG-3 antibody comprises heavy and light chains comprising the sequences set forth in SEQ ID NOs:1 and 2, respectively, and the anti-PD-1 antibody comprises heavy and light chains comprising the sequences as set forth in SEQ ID NOs:17 and 18, respectively.

11. The pharmaceutical composition of claim 1, wherein the concentrations of the anti-LAG-3 antibody or antigen binding fragment thereof and the anti-PD-1 antibody or antigen binding fragment thereof are 4 mg/mL and 12 mg/mL, respectively.

12. The pharmaceutical composition of claim 1, wherein the composition is for intravenous administration.

13. A vial comprising 20 mL of a pharmaceutical composition comprising:
(a) about 80 mg of an anti-LAG-3 antibody or antigen binding fragment thereof comprising CDR1, CDR2, and CDR3 domains of the heavy chain variable region having the sequence set forth in SEQ ID NO:3, and CDR1, CDR2, and CDR3 domains of the light chain variable region having the sequence set forth in SEQ ID NO:5;
(b) about 240 mg of an anti-PD-1 antibody or antigen binding fragment thereof comprising CDR1, CDR2, and CDR3 domains of the heavy chain variable region having the sequence set forth in SEQ ID NO:19, and CDR1, CDR2, and CDR3 domains of the light chain variable region having the sequence set forth in SEQ ID NO:21;
(c) about 20 mM of histidine buffer;
(d) about 250 mM of sucrose;
(e) about 20 µM of DTPA; and
(f) about 0.05% (w/v) of polysorbate 80;
wherein the pharmaceutical composition has a pH of about 5.8.

14. The vial of claim 13, wherein the anti-LAG-3 antibody or antigen binding fragment thereof comprises heavy chain variable region CDR1, CDR2, and CDR3 domains comprising the sequences set forth in SEQ ID NOs:7, 8, and 9, respectively, and light chain variable region CDR1, CDR2, and CDR3 domains comprising the sequences set forth in SEQ ID NOs:10, 11, and 12, respectively, and the anti-PD-1 antibody or antigen binding fragment thereof comprises heavy chain variable region CDR1, CDR2, and CDR3 domains comprising the sequences set forth in SEQ ID NOs:23, 24, and 25, respectively, and light chain variable region CDR1, CDR2, and CDR3 domains comprising the sequences set forth in SEQ ID NOs:26, 27, and 28, respectively.

15. The vial of claim 13, wherein the anti-LAG-3 antibody or antigen binding fragment thereof comprises heavy and light chain variable regions comprising the sequences set forth in SEQ ID NOs:3 and 5, respectively, and the anti-PD-1 antibody or antigen binding fragment thereof comprises heavy and light chain variable regions comprising the sequences set forth in SEQ ID NOs:19 and 21, respectively.

16. The vial of claim 13, wherein the anti-LAG-3 antibody comprises heavy and light chains comprising the sequences set forth in SEQ ID NOs:1 and 2, respectively, and the anti-PD-1 antibody comprises heavy and light chains comprising the sequences as set forth in SEQ ID NOs:17 and 18, respectively.

17. An infusion solution comprising:
(a) about 160 mg of an anti-LAG-3 antibody or antigen binding fragment thereof comprising CDR1, CDR2, and CDR3 domains of the heavy chain variable region having the sequence set forth in SEQ ID NO:3, and CDR1, CDR2, and CDR3 domains of the light chain variable region having the sequence set forth in SEQ ID NO:5;
(b) about 480 mg of an anti-PD-1 antibody or antigen binding fragment thereof comprising CDR1, CDR2, and CDR3 domains of the heavy chain variable region having the sequence set forth in SEQ ID NO:19, and CDR1, CDR2, and CDR3 domains of the light chain variable region having the sequence set forth in SEQ ID NO:21;
(c) about 20 mM of histidine buffer;
(d) about 250 mM of sucrose;
(e) about 20 µM of DTPA; and
(f) about 0.05% (w/v) of polysorbate 80;
wherein the infusion solution has a pH of about 5.8.

18. The infusion solution of claim 17, wherein the anti-LAG-3 antibody or antigen binding fragment thereof comprises heavy chain variable region CDR1, CDR2, and CDR3 domains comprising the sequences set forth in SEQ ID NOs:7, 8, and 9, respectively, and light chain variable region CDR1, CDR2, and CDR3 domains comprising the sequences set forth in SEQ ID NOs:10, 11, and 12, respectively, and the anti-PD-1 antibody or antigen binding fragment thereof comprises heavy chain variable region CDR1, CDR2, and CDR3 domains comprising the sequences set forth in SEQ ID NOs:23, 24, and 25, respectively, and light chain variable region CDR1, CDR2, and CDR3 domains comprising the sequences set forth in SEQ ID NOs:26, 27, and 28, respectively.

19. The infusion solution of claim 17, wherein the anti-LAG-3 antibody or antigen binding fragment thereof comprises heavy and light chain variable regions comprising the sequences set forth in SEQ ID NOs:3 and 5, respectively, and the anti-PD-1 antibody or antigen binding fragment thereof comprises heavy and light chain variable regions comprising the sequences set forth in SEQ ID NOs:19 and 21, respectively.

20. The infusion solution of claim 17, wherein the anti-LAG-3 antibody comprises heavy and light chains comprising the sequences set forth in SEQ ID NOs:1 and 2, respectively, and the anti-PD-1 antibody comprises heavy and light chains comprising the sequences as set forth in SEQ ID NOs:17 and 18, respectively.

21. An intravenous bag comprising the infusion solution of claim 17.

22. An intravenous bag comprising a dilution of the infusion solution of claim 17.

23. The intravenous bag of claim 22, wherein the diluent is 0.9% Sodium Chloride Injection, USP.

24. The intravenous bag of claim 22, wherein the diluent is 5% Dextrose Injection, USP.

* * * * *